US008956847B2

(12) United States Patent
Foster et al.

(10) Patent No.: US 8,956,847 B2
(45) Date of Patent: *Feb. 17, 2015

(54) FUSION PROTEINS

(71) Applicant: Syntaxin, Limited, Abingdon, Oxfordshire (GB)

(72) Inventors: Keith Alan Foster, Abingdon (GB); John Chaddock, Abingdon (GB); Philip Marks, Abingdon (GB); Patrick Stancombe, Abingdon (GB); Lyndsey Durose, Abingdon (GB)

(73) Assignee: Syntaxin Limited, Abingdon, Oxfordshire (GB)

( * ) Notice: Subject to any disclaimer, the term of this patent is extended or adjusted under 35 U.S.C. 154(b) by 65 days.

This patent is subject to a terminal disclaimer.

(21) Appl. No.: 13/738,235

(22) Filed: Jan. 10, 2013

(65) Prior Publication Data

US 2013/0115682 A1 May 9, 2013

Related U.S. Application Data

(63) Continuation of application No. 13/354,787, filed on Jan. 20, 2012, now Pat. No. 8,372,615, which is a continuation of application No. 11/792,076, filed as application No. PCT/GB2005/004606 on Dec. 1, 2005, now Pat. No. 8,124,074.

(30) Foreign Application Priority Data

Dec. 1, 2004 (GB) .................................. 0426397.6

(51) Int. Cl.
*C12N 9/50* (2006.01)
*C07K 14/33* (2006.01)
*C12N 15/62* (2006.01)
*A61K 38/00* (2006.01)

(52) U.S. Cl.
CPC . *C12N 9/50* (2013.01); *C07K 14/33* (2013.01); *C12N 15/62* (2013.01); *A61K 38/00* (2013.01); *C07K 2319/06* (2013.01); *C07K 2319/50* (2013.01)
USPC ......................... 435/219; 536/23.2; 435/320.1

(58) Field of Classification Search
CPC ......... A61K 38/00; C07K 14/33; C12N 15/62
See application file for complete search history.

(56) References Cited

U.S. PATENT DOCUMENTS

| 6,395,513 | B1 | 5/2002 | Foster et al. |
|---|---|---|---|
| 6,632,440 | B1 | 10/2003 | Quinn et al. |
| 7,052,702 | B1 | 5/2006 | Duggan et al. |
| 7,132,259 | B1 | 11/2006 | Dolly et al. |
| 7,192,596 | B2 | 3/2007 | Shone et al. |
| 7,419,676 | B2 | 9/2008 | Dolly et al. |
| 7,422,877 | B2 | 9/2008 | Dolly et al. |
| 7,811,584 | B2 | 10/2010 | Steward et al. |
| 8,124,074 | B2 | 2/2012 | Foster et al. |
| 8,372,615 | B2 * | 2/2013 | Foster et al. .................. 435/188 |
| 2003/0166238 | A1 | 9/2003 | Shone et al. |
| 2003/0180289 | A1 | 9/2003 | Foster et al. |
| 2004/0071736 | A1 | 4/2004 | Quinn et al. |
| 2008/0032930 | A1 | 2/2008 | Steward et al. |
| 2008/0032931 | A1 | 2/2008 | Steward et al. |
| 2008/0064092 | A1 | 3/2008 | Foster et al. |
| 2008/0081355 | A1 | 4/2008 | Dolly et al. |
| 2008/0096248 | A1 | 4/2008 | Steward et al. |
| 2008/0161226 | A1 | 7/2008 | Steward et al. |
| 2008/0161543 | A1 | 7/2008 | Steward et al. |
| 2008/0182294 | A1 | 7/2008 | Dolly et al. |
| 2008/0213830 | A1 | 9/2008 | Steward et al. |
| 2008/0221012 | A1 | 9/2008 | Steward et al. |
| 2008/0311622 | A1 | 12/2008 | Dolly et al. |
| 2009/0004224 | A1 | 1/2009 | Steward et al. |
| 2009/0005313 | A1 | 1/2009 | Steward et al. |

FOREIGN PATENT DOCUMENTS

| WO | 9421300 | 9/1994 |
|---|---|---|
| WO | 9807864 A1 | 2/1998 |
| WO | 0114570 A1 | 3/2001 |
| WO | 0121213 A3 | 3/2001 |

(Continued)

OTHER PUBLICATIONS

Foster, Keith A. "The Analgesic Potential of Clostridial Neurotoxin Derivatives" Expert Opinion, Ashley Publications, (2004) 13(11); pp. 1437-1443.
Michaela Robbie-Ryan, "The role of mast cells in allergy and autoimmunity" ScienceDirect, Current Opinion in Immunology, vol. 14, Issue 6, Dec. 1, 2002. [Abstract].
David A. Brenner, "Prolonged activation of jun and collagenase genes by tumour necrosis factor" Letters to Nature, 337, Feb. 16, 1989. [Abstract].
Stack WA, "Randomized controlled trial of CDP571 antibody to tumour necrosis factor-alpha in Crohn's disease" PubMed, Lancet, Feb. 22, 1997; 349(9051). [Abstract].
C. Parksinson, "The relationship between Serum GH and Serum IGF-I in Acromegaly is Gender-Specific" The Journal of Clinical Endocrinology & Metabolism, Metabolism 86(11); p. 5240; [2001]. [Abstract].
Ira D. Goldfine, "Medical Treatment of Acromegaly" Ann. Rev. Med. [1978] 29; p. 407. [Abstract].

(Continued)

*Primary Examiner* — Scott Long
(74) *Attorney, Agent, or Firm* — Morris, Manning & Martin, LLP; Christopher W. Raimund

(57) ABSTRACT

The invention provides a single chain, polypeptide fusion protein, comprising: a non-cytotoxic protease, or a fragment thereof, which protease or protease fragment is capable of cleaving a protein of the exocytic fusion apparatus of a target cell; a Targeting Moiety that is capable of binding to a Binding Site on the target cell, which Binding Site is capable of undergoing endocytosis to be incorporated into an endocome within the target cell; a protease cleaving site at which site the fusion protein is cleavable by the protease, wherein the protease cleavage site is located between the non-cytotoxic protease or fragment thereof and the Targeting Moiety; and the translocation domain that is capable of translocating the protease or protease fragment from within an endosome, across the endosomal membrane and into the cytosol of the target cell.

25 Claims, 1 Drawing Sheet

(56) References Cited

FOREIGN PATENT DOCUMENTS

| WO | 0162269 A2 | 8/2001 |
| WO | 02074327 A3 | 9/2002 |
| WO | 2004024909 A2 | 3/2004 |
| WO | 2005023309 A2 | 3/2005 |
| WO | 2006059093 A2 | 6/2006 |
| WO | 2006059105 A2 | 6/2006 |
| WO | 2006059113 A2 | 6/2006 |

OTHER PUBLICATIONS

Dagar, et al. (Journal of Controlled Release. 2001; 74: 129-134).

J.M. Sutton, et al., "Preparation of Specifically Activatable Endopeptidase Derivatives of *Clostridium botulinum* Toxins Type A, B and C and their Applications," Protein Expression and Purification, Academic Press, vol. 40, No. 1, Mar. 2005, pp. 31-41.

J. A. Chaddock, et al., "Clostridial Neurotoxins: Structure-function Led Design of New Therapeutics," Cellular and Molecular Life Sciences: CMLS, vol. 63, No. 5, Mar. 2006, pp. 540-551.

\* cited by examiner

FUSION PROTEINS

This application is a continuation of U.S. patent application Ser. No. 13/354,787, filed on Jan. 20, 2012, allowed, which is a continuation of U.S. patent application Ser. No. 11/792,076, now U.S. Pat. No. 8,124,074, which is a national phase entry of International Patent Application No. PCT/GB2005/04606, filed on Dec. 1, 2005. Each of the above applications is incorporated by reference herein in its entirety.

Pursuant to the provisions of 37 C.F.R. §1.52(e)(5), the sequence listing text file named 88143_Seq_Listing.txt, created on Dec. 17, 2012 and having a size of 126,976 bytes, and which is being submitted herewith, is incorporated by reference herein in its entirety.

This invention relates to non-cytotoxic fusion proteins, and to the therapeutic application thereof.

Toxins may be generally divided into two groups according to the type of effect that they have on a target cell. In more detail, the first group of toxins kill their natural target cells, and are therefore known as cytotoxic toxin molecules. This group of toxins is exemplified inter alia by plant toxins such as ricin, and abrin, and by bacterial toxins such as diphtheria toxin, and *Pseudomonas* exotoxin A. Cytotoxic toxins have attracted much interest in the design of "magic bullets" (eg. immunoconjugates, which comprise a cytotoxic toxin component and an antibody that binds to a specific marker on a target cell) for the treatment of cellular disorders and conditions such as cancer. Cytotoxic toxins typically kill their target cells by inhibiting the cellular process of protein synthesis.

The second group of toxins, which are known as non-cytotoxic toxins, do not (as their name confirms) kill their natural target cells. Non-cytotoxic toxins have attracted much less commercial interest than have their cytotoxic counterparts, and exert their effects on a target cell by inhibiting cellular processes other than protein synthesis. Non-cytotoxic toxins are produced by a variety of plants, and by a variety of microorganisms such as *Clostridium* sp. and *Neisseria* sp.

Clostridial neurotoxins are proteins that typically have a molecular mass of the order of 150 kDa. They are produced by various species of bacteria, especially of the genus *Clostridium*, most importantly *C. tetani* and several strains of *C. botulinum*, *C. butyricum* and *C. argentinense*. There are at present eight different classes of the clostridial neurotoxin, namely: tetanus toxin, and botulinum neurotoxin in its serotypes A, B, C1, D, E, F and G, and they all share similar structures and modes of action.

Clostridial neurotoxins represent a major group of non-cytotoxic toxin molecules, and are synthesised by the host bacterium as single polypeptides that are modified post-translationally by a proteolytic cleavage event to form two polypeptide chains joined together by a disulphide bond. The two chains are termed the heavy chain (H-chain), which has a molecular mass of approximately 100 kDa, and the light chain (L-chain), which has a molecular mass of approximately 50 kDa.

L-chains possess a protease function (zinc-dependent endopeptidase activity) and exhibit a high substrate specificity for vesicle and/or plasma membrane associated proteins involved in the exocytic process. L-chains from different clostridial species or serotypes may hydrolyse different but specific peptide bonds in one of three substrate proteins, namely synaptobrevin, syntaxin or SNAP-25. These substrates are important components of the neurosecretory machinery.

*Neisseria* sp., most importantly from the species *N. gonorrhoeae*, produce functionally similar non-cytotoxic proteases. An example of such a protease is IgA protease (see WO99/58571).

It has been well documented in the art that toxin molecules may be re-targeted to a cell that is not the toxin's natural target cell. When so re-targeted, the modified toxin is capable of binding to a desired target cell and, following subsequent translocation into the cytosol, is capable of exerting its effect on the target cell. Said re-targeting is achieved by replacing the natural Targeting Moiety (TM) of the toxin with a different TM. In this regard, the TM is selected so that it will bind to a desired target cell, and allow subsequent passage of the modified toxin into an endosome within the target cell. The modified toxin also comprises a translocation domain to enable entry of the non-cytotoxic protease into the cell cytosol. The translocation domain can be the natural translocation domain of the toxin or it can be a different translocation domain obtained from a microbial protein with translocation activity.

For example, WO94/21300 describes modified clostridial neurotoxin molecules that are capable of regulating Integral Membrane Protein (IMP) density present at the cell surface of the target cell. The modified neurotoxin molecules are thus capable of controlling cell activity (eg. glucose uptake) of the target cell. WO96/33273 and WO99/17806 describe modified clostridial neurotoxin molecules that target peripheral sensory afferents. The modified neurotoxin molecules are thus capable of demonstrating an analgesic effect. WO00/10598 describes the preparation of modified clostridial neurotoxin molecules that target mucus hypersecreting cells (or neuronal cells controlling said mucus hypersecreting cells), which modified neurotoxins are capable of inhibiting hypersecretion from said cells. WO01/21213 describes modified clostridial neurotoxin molecules that target a wide range of different types of non-neuronal target cells. The modified molecules are thus capable of preventing secretion from the target cells. Additional publications in the technical field of re-targeted toxin molecules include:—WO00/62814; WO00/04926; U.S. Pat. No. 5,773,586; WO93/15766; WO00/61192; and WO99/58571.

The above-mentioned TM replacement may be effected by conventional chemical conjugation techniques, which are well known to a skilled person. In this regard, reference is made to Hermanson, G. T. (1996), Bioconjugate techniques, Academic Press, and to Wong, S. S. (1991), Chemistry of protein conjugation and cross-linking, CRC Press.

Chemical conjugation is, however, often imprecise. For example, following conjugation, a TM may become joined to the remainder of the conjugate at more than one attachment site.

Chemical conjugation is also difficult to control. For example, a TM may become joined to the remainder of the modified toxin at an attachment site on the protease component and/or on the translocation component. This is problematic when attachment to only one of said components (preferably at a single site) is desired for therapeutic efficacy.

Thus, chemical conjugation results in a mixed population of modified toxin molecules, which is undesirable.

As an alternative to chemical conjugation, TM replacement may be effected by recombinant preparation of a single polypeptide fusion protein (see WO98/07864). This technique is based on the in vivo bacterial mechanism by which native clostridial neurotoxin (ie. holotoxin) is prepared, and results in a fusion protein having the following structural arrangement:

NH$_2$-[protease component]-[translocation component]-[TM]-COOH

According to WO98/07864, the TM is placed towards the C-terminal end of the fusion protein. The fusion protein is then activated by treatment with a protease, which cleaves at a site between the protease component and the translocation component. A di-chain protein is thus produced, comprising the protease component as a single polypeptide chain covalently attached (via a disulphide bridge) to another single polypeptide chain containing the translocation component plus TM. Whilst the WO 98/07864 methodology follows (in terms of structural arrangement of the fusion protein) the natural expression system of clostridial holotoxin, the present inventors have found that this system may result in the production of certain fusion proteins that have a substantially-reduced binding ability for the intended target cell.

There is therefore a need for an alternative or improved system for constructing a non-cytotoxic fusion protein.

The present invention addresses one or more of the above-mentioned problems by providing a single chain, polypeptide fusion protein, comprising:—
  a. a non-cytotoxic protease, or a fragment thereof, which protease or protease fragment is capable of cleaving a protein of the exocytic fusion apparatus in a target cell;
  b. a Targeting Moiety that is capable of binding to a Binding Site on the target cell, which Binding Site is capable of undergoing endocytosis to be incorporated into an endosome within the target cell;
  c. a protease cleavage site at which site the fusion protein is cleavable by a protease, wherein the protease cleavage site is located between the non-cytotoxic protease or fragment thereof and the Targeting Moiety; and
a translocation domain that is capable of translocating the protease or protease fragment from within an endosome, across the endosomal membrane and into the cytosol of the target cell.

The WO98/07864 system works well for the preparation of conjugates having a TM that requires a C-terminal domain for interaction with a Binding Site on a target cell. In this regard, WO98/07864 provides fusion proteins having a C-terminal domain that is "free" to interact with a Binding Site on a target cell. The present inventors have found that this structural arrangement is not suitable for all TMs. In more detail, the present inventors have found that the WO 98/07864 fusion protein system is not optimal for TMs requiring a N-terminal domain for interaction with a binding site on a target cell. This problem is particularly acute with TMs that require a specific N-terminus amino acid residue or a specific sequence of amino acid residues including the N-terminus amino acid residue for interaction with a binding site on a target cell.

In contrast to WO98/07864, the present invention provides a system for preparing non-cytotoxic conjugates, wherein the TM component of the conjugate has an N-terminal domain (or an intra domain sequence) that is capable of binding to a Binding Site on a target cell.

The non-cytotoxic protease component of the present invention is a non-cytotoxic protease, or a fragment thereof, which protease or protease fragment is capable of cleaving different but specific peptide bonds in one of three substrate proteins, namely synaptobrevin, syntaxin or SNAP-25, of the exocytic fusion apparatus. These substrates are important components of the neurosecretory machinery. The non-cytotoxic protease component of the present invention is preferably a neisserial IgA protease or a fragment thereof or a clostridial neurotoxin L-chain or a fragment thereof. A particularly preferred non-cytotoxic protease component is a botulinum neurotoxin (BoNT) L-chain or a fragment thereof.

The translocation component of the present invention enables translocation of the non-cytotoxic protease (or fragment thereof) into the target cell such that functional expression of protease activity occurs within the cytosol of the target cell. The translocation component is preferably capable of forming ion-permeable pores in lipid membranes under conditions of low pH. Preferably it has been found to use only those portions of the protein molecule capable of pore-formation within the endosomal membrane. The translocation component may be obtained from a microbial protein source, in particular from a bacterial or viral protein source. Hence, in one embodiment, the translocation component is a translocating domain of an enzyme, such as a bacterial toxin or viral protein. The translocation component of the present invention is preferably a clostridial neurotoxin H-chain or a fragment thereof. Most preferably it is the H$_N$ domain (or a functional component thereof), wherein H$_N$ means a portion or fragment of the H-chain of a clostridial neurotoxin approximately equivalent to the amino-terminal half of the H-chain, or the domain corresponding to that fragment in the intact H-chain.

The TM component of the present invention is responsible for binding the conjugate of the present invention to a Binding Site on a target cell. Thus, the TM component is simply a ligand through which a conjugate of the present invention binds to a selected target cell.

In the context of the present invention, the target cell may be any target cell, though with the proviso that the target cell is not a nociceptive sensory afferent such as a primary sensory afferent. Thus, the TM may bind to non-neuronal cells and/or to neuronal cells.

It is routine to confirm that a TM binds to a given target cell. For example, a simple radioactive displacement experiment may be employed in which tissue or cells representative of the target cell are exposed to labelled (eg. tritiated) ligand in the presence of an excess of unlabelled ligand. In such an experiment, the relative proportions of non-specific and specific binding may be assessed, thereby allowing confirmation that the ligand binds to the target cell. Optionally, the assay may include one or more binding antagonists, and the assay may further comprise observing a loss of ligand binding. Examples of this type of experiment can be found in Hulme, E. C. (1990), Receptor-binding studies, a brief outline, pp. 303-311, In Receptor biochemistry, A Practical Approach, Ed. E. C. Hulme, Oxford University Press.

The fusion proteins of the present invention generally demonstrate a reduced binding affinity (in the region of up to 100-fold) for target cells when compared with the corresponding 'free' TM. However, despite this observation, the fusion proteins of the present invention surprisingly demonstrate good efficacy. This can be attributed to two principal features. First, the non-cytotoxic protease component is catalytic—thus, the therapeutic effect of a few such molecules is rapidly amplified. Secondly, the receptors present on the target cells need only act as a gateway for entry of the therapeutic, and need not necessarily be stimulated to a level required in order to achieve a ligand-receptor mediated pharmacological response. Accordingly, the fusion proteins of the present invention may be administered at a dosage that is lower that would be employed for other types of therapeutic molecules, which are typically administered at high microgram to milligram (even up to hundreds of milligram) quantities. In contrast, the fusion proteins of the present invention may be administered at much lower dosages, typically at least 10-fold lower, and more typically at 100-fold lower.

The TM preferably comprises a maximum of 50 amino acid residues, more preferably a maximum of 40 amino acid residues, particularly preferably a maximum of 30 amino acid residues, and most preferably a maximum of 20 amino acid residues.

Proteinase activated receptor ligands represent a preferred group of TMs of the present invention, in particular PAR1. PARs represent a unique subtype of 7-transmembrane receptor G-protein-coupled receptors in that they are proteolytically modified to expose a new extracellular N-terminus, which acts as a tethered activating ligand. PAR1 agonists (such as TFLLR) have been identified that activate their cognate receptor.

Parathyroid hormone (PTH) also represents a preferred TM of the present invention. PTH is released by the parathyroid gland and binds to the PTH-1 receptor. This receptor has a widespread distribution but is particularly abundant in PTH target tissues, predominantly the kidney and in bone.

Thus, the most preferred TMs of the present invention are:—

| LIGAND | REFERENCE |
| --- | --- |
| Protease activated receptor Ligand (PAR1) | C. K. Derian, B. E. Maryanoff, P. Andrade-Gordon, and H-C Zhang DRUG DEVELOPMENT RESEARCH 59: 355 (2003) |
| PTH | Shimizu M., et al 2000, J Biol Chem. Jul 21; 275(29): 21836-43 |

According to one embodiment of the present invention, the TM binds to a mucus-secreting cell, or to a neuronal cell controlling or directing mucus secretion. More specifically, the TM bind to (a) cells that secrete mucins, such as epithelial goblet cells and submucosal gland mucus secreting cells, (b) cells that secrete aqueous components of mucus, such as Clara cells and serous cells, or (c) cells that control or direct mucus secretion, such as "sensory-efferent" C-fibres, or NANC neural system fibres. In this regard, particular mention is made to the TMs:—VIP; beta$_2$ adrenoreceptor agonists; gastrin-releasing peptide; and calcitonin gene related peptide. Thus, according to this embodiment, said conjugates have therapeutic application in treating mucus hypersecretion, asthma, and/or chronic obstructive pulmonary disease.

In another embodiment, the TM binds to an endocrine cell. Particular mention is made here to thyroid stimulating hormone (TSH); insulin, insulin-like growth factor; TSH releasing hormone (protirelin); FSH/LH releasing hormone (gonadorelin); corticotrophin releasing hormone (CRH); and ACTH. Thus, according to this embodiment, said conjugates have therapeutic application in treating:—endocrine neoplasia including MEN; thyrotoxicosis and other diseases dependent on hypersecretions from the thyroid; acromegaly, hyperprolactinaemia, Cushings disease and other diseases dependent on anterior pituitary hypersecretion; hyperandrogenism, chronic anovulation and other diseases associated with polycystic ovarian syndrome.

In another embodiment the TM binds to an inflammatory cell. Particular mention here is made to ligands (i) for mast cells, such as the C4 domain of the Fc IgE; (ii) for eosinophils, such as ligands to the C3a/C4a-R complement receptor, antigens reactive towards CR4 complement receptor; (iii) for macrophages and monocytes, such as macrophage stimulating factor, (iv) for neutrophils, such as an antigen associated with the iC3b complement receptor, or IL8. Thus, according to this embodiment, said conjugates have therapeutic application for treating allergies (seasonal allergic rhinitis (hay fever), allergic conjunctivitis, vasomotor rhinitis and food allergy), eosinophilia, asthma, rheumatoid arthritis, systemic lupus erythematosus, discoid lupus erythematosus, ulcerative colitis, Crohn's disease, haemorrhoids, pruritus, glomerulonephritis, hepatitis, pancreatitis, gastritis, vasculitis, myocarditis, psoriasis, eczema, chronic radiation-induced fibrosis, lung scarring and other fibrotic disorders.

In another embodiment, the TM binds to an exocrine cell. Particular mention here is made to pituitary adenyl cyclase activating peptide (PACAP-38). Thus, according to this embodiment, said conjugates have therapeutic application for treating mucus hypersecretion from mucus-secreting cells located in the alimentary tract, in particular located in the colon.

In a further embodiment, the TM binds to an immunological cell. Mention here is made to the ligands:—Epstein Barr virus fragment/surface feature. Thus, according to this embodiment, said conjugates have therapeutic application for treating myasthenia gravis, rheumatoid arthritis, systemic lupus erythematosus, discoid lupus erythematosus, organ transplant, tissue transplant, fluid transplant, Graves disease, thyrotoxicosis, autoimmune diabetes, haemolytic anaemia, thrombocytopenic purpura, neutropenia, chronic autoimmune hepatitis, autoimmune gastritis, pernicious anaemia, Hashimoto's thyroiditis, Addison's disease, Sjogren's syndrome, primary biliary cirrhosis, polymyositis, scleroderma, systemic sclerosis, pemphigus vulgaris, bullous pemphigoid, myocarditis, rheumatic carditis, glomerulonephritis (Goodpasture type), uveitis, orchitis, ulcerative colitis, vasculitis, atrophic gastritis, pernicious anaemia, type 1 diabetes mellitus.

In a further embodiment the TM binds to a cardiovascular cell. Mention here is made to thrombin and TRAP (thrombin receptor agonist peptide), and ligands that bind to cardiovascular endothelial cells such as GP1b surface antigen-recognising antibodies. Thus, according to this embodiment, said conjugates have therapeutic application for treating cardiovascular conditions and/or hypertension In a further embodiment, the TM binds to a bone cell. Mention here is made to ligands that bind to osteoblasts for the treatment of a disease selected from osteopetrosis and osteoporosis include calcitonin, and to ligands that bind to osteoclasts including osteoclast differentiation factors (eg. TRANCE, or RANKL or OPGL). Thus, according to this embodiment, said conjugates have therapeutic application for treating bone conditions.

Linear and cyclic integrin binding sequences are a preferred group of TMs of the present invention. Many integrins recognise the triple Arg-Gly-Asp (RGD) peptide sequence (Ruoslahti, 1996). The RGD motif is found in over 100 proteins including fibronectin, tenascin, fibrinogen and vitronectin. The RGD-integrin interaction is exploited as a conserved mechanism of cell entry by many pathogens including coxsackievirus (Roivaninen et al., 1991) and adenovirus (Mathias et al., 1994). The linear and cyclic peptide sequences, PLAEIDGIEL and CPLAEIDGIELC respectively, have been shown to bind and internalise DNA in cells expressing $\alpha_9\beta_1$ integrin (Schneider et al., 1999).

Other TMs of the present invention include those discovered by phage display techniques, in particular those which target and are internalised by human airway epithelial cells. These include, linear and cyclic THALWHT (Jost et al., 2001); LEBP-1 (QPFMQCLCLIYDASC), LEBP-2 (RNVPPIFNDVYWIAF) and LEBP-3 (VFRVRPWYQSTSQS) (Wu et al., 2003); CDSAFVTVDWGRSMSLC (Florea et al., 2003); SERSMNF, YGLPHKF, PSGAARA, LPHKSMP, LQHKSMP (Writer et al., 2004); FSLSKPP, HSMQLST and STQAMFQ peptides (Rahim et al., 2003).

The protease cleavage site of the present invention allows cleavage (preferably controlled cleavage) of the fusion protein at a position between the non-cytotoxic protease component and the TM component. It is this cleavage reaction that converts the fusion protein from a single chain polypeptide into a disulphide-linked, di-chain polypeptide.

According to a preferred embodiment of the present invention, the TM binds via a domain or amino acid sequence that is located away from the C-terminus of the TM. For example, the relevant binding domain may include an intra domain or an amino acid sequence located towards the middle (ie. of the linear peptide sequence) of the TM. Preferably, the relevant binding domain is located towards the N-terminus of the TM, more preferably at or near to the N-terminus.

In one embodiment, the single chain polypeptide fusion may include more than one proteolytic cleavage site. However, where two or more such sites exist, they are different, thereby substantially preventing the occurrence of multiple cleavage events in the presence of a single protease. In another embodiment, it is preferred that the single chain polypeptide fusion has a single protease cleavage site.

The protease cleavage sequence(s) may be introduced (and/or any inherent cleavage sequence removed) at the DNA level by conventional means, such as by site-directed mutagenesis. Screening to confirm the presence of cleavage sequences may be performed manually or with the assistance of computer software (eg. the MapDraw program by DNAS-TAR, Inc.).

Whilst any protease cleavage site may be employed, the following are preferred:—

| | |
|---|---|
| Enterokinase | (DDDDK↓) |
| Factor Xa | (IEGR↓/IDGR↓) |
| TEV(Tobacco Etch virus) | (ENLYFQ↓G) |
| Thrombin | (LVPR↓GS) |
| PreScission | (LEVLFQ↓GP). |

Also embraced by the term protease cleavage site is an intein, which is a self-cleaving sequence. The self-splicing reaction is controllable, for example by varying the concentration of reducing agent present.

In use, the protease cleavage site is cleaved and the N-terminal region (preferably the N-terminus) of the TM becomes exposed. The resulting polypeptide has a TM with an N-terminal domain or an intra domain that is substantially free from the remainder of the conjugate. This arrangement ensures that the N-terminal component (or intra domain) of the TM may interact directly with a Binding Site on a target cell.

In a preferred embodiment, the TM and the protease cleavage site are distanced apart in the fusion protein by at most 10 amino acid residues, more preferably by at most 5 amino acid residues, and most preferably by zero amino acid residues. Thus, following cleavage of the protease cleavage site, a conjugate is provided with a TM that has an N-terminal domain that is substantially free from the remainder of the conjugate. This arrangement ensures that the N-terminal component of the Targeting Moiety may interact directly with a Binding Site on a target cell.

One advantage associated with the above-mentioned activation step is that the TM only becomes susceptible to N-terminal degradation once proteolytic cleavage of the fusion protein has occurred. In addition, the selection of a specific protease cleavage site permits selective activation of the polypeptide fusion into a di-chain conformation.

Construction of the single-chain polypeptide fusion of the present invention places the protease cleavage site between the TM and the non-cytotoxic protease component.

It is preferred that, in the single-chain fusion, the TM is located between the protease cleavage site and the translocation component. This ensures that the TM is attached to the translocation domain (ie. as occurs with native clostridial holotoxin), though in the case of the present invention the order of the two components is reversed vis-à-vis native holotoxin. A further advantage with this arrangement is that the TM is located in an exposed loop region of the fusion protein, which has minimal structural effects on the conformation of the fusion protein. In this regard, said loop is variously referred to as the linker, the activation loop, the inter-domain linker, or just the surface exposed loop (Schiavo et al 2000, Phys. Rev., 80, 717-766; Turton et al., 2002, Trends Biochem. Sci., 27, 552-558).

In one embodiment, in the single chain polypeptide, the non-cytotoxic protease component and the translocation component are linked together by a disulphide bond. Thus, following cleavage of the protease cleavage site, the polypeptide assumes a di-chain conformation, wherein the protease and translocation components remain linked together by the disulphide bond. To this end, it is preferred that the protease and translocation components are distanced apart from one another in the single chain fusion protein by a maximum of 100 amino acid residues, more preferably a maximum of 80 amino acid residues, particularly preferably by a maximum of 60 amino acid residues, and most preferably by a maximum of 50 amino acid residues.

In one embodiment, the non-cytotoxic protease component forms a disulphide bond with the translocation component of the fusion protein. For example, the amino acid residue of the protease component that forms the disulphide bond is located within the last 20, preferably within the last 10 C-terminal amino acid residues of the protease component. Similarly, the amino acid residue within the translocation component that forms the second part of the disulphide bond may be located within the first 20, preferably within the first 10 N-terminal amino acid residues of the translocation component.

Alternatively, in the single chain polypeptide, the non-cytotoxic protease component and the TM may be linked together by a disulphide bond. In this regard, the amino acid residue of the TM that forms the disulphide bond is preferably located away from the N-terminus of the TM, more preferably towards to C-terminus of the TM.

In one embodiment, the non-cytotoxic protease component forms a disulphide bond with the TM component of the fusion protein. In this regard, the amino acid residue of the protease component that forms the disulphide bond is preferably located within the last 20, more preferably within the last 10 C-terminal amino acid residues of the protease component. Similarly, the amino acid residue within the TM component that forms the second part of the disulphide bond is preferably located within the last 20, more preferably within the last 10 C-terminal amino acid residues of the TM.

The above disulphide bond arrangements have the advantage that the protease and translocation components are arranged in a manner similar to that for native clostridial neurotoxin. By way of comparison, referring to the primary amino acid sequence for native clostridial neurotoxin, the respective cysteine amino acid residues are distanced apart by between 8 and 27 amino acid residues—taken from Popoff, M R & Marvaud, J-C, 1999, Structural & genomic features of clostridial neurotoxins, Chapter 9, in The Comprehensive Sourcebook of Bacterial Protein Toxins. Ed. Alouf & Freer:—

| Serotype[1] | Sequence | 'Native' length between C-C |
|---|---|---|
| BoNT/A1 | CVRGIITSKTKS----LDKGYNKALNDLC | 23 |
| BoNT/A2 | CVRGIIPFKTKS----LDEGYNKALNDLC | 23 |
| BoNT/B | CKSVKAPG------------------IC | 8 |
| BoNT/C | CHKAIDGRS----------LYNKTLDC | 15 |
| BoNT/D | CLRLTK--------------NSRDDSTC | 12 |
| BoNT/E | CKN-IVSVK----------GIRK---SIC | 13 |
| BoNT/F | CKS-VIPRK----------GTKAPP-RLC | 15 |
| BoNT/G | CKPVMYKNT----------GKSE----QC | 13 |
| TeNT | CKKIIPPTNIRENLYNRTASLTDLGGELC | 27 |

[1]Information from proteolytic strains only

The fusion protein may comprise one or more purification tags, which are located N-terminal to the protease component and/or C-terminal to the translocation component.

Whilst any purification tag may be employed, the following are preferred:—

His-tag (eg. 6×histidine), preferably as a C-terminal and/or N-terminal tag

MBP-tag (maltose binding protein), preferably as an N-terminal tag

GST-tag (glutathione-S-transferase), preferably as an N-terminal tag

His-MBP-tag, preferably as an N-terminal tag

GST-MBP-tag, preferably as an N-terminal tag

Thioredoxin-tag, preferably as an N-terminal tag

CBD-tag (Chitin Binding Domain), preferably as an N-terminal tag.

According to a further embodiment of the present invention, one or more peptide spacer molecules may be included in the fusion protein. For example, a peptide spacer may be employed between a purification tag and the rest of the fusion protein molecule (eg. between an N-terminal purification tag and a protease component of the present invention; and/or between a C-terminal purification tag and a translocation component of the present invention). A peptide spacer may be also employed between the TM and translocation components of the present invention.

In accordance with a second aspect of the present invention, there is provided a DNA sequence that encodes the above-mentioned single chain polypeptide.

In a preferred aspect of the present invention, the DNA sequence is prepared as part of a DNA vector, wherein the vector comprises a promoter and terminator.

A variety of different spacer molecules may be employed in any of the fusion proteins of the present invention. Examples of such spacer molecules include GS15, GS20, GS25, and Hx27.

The present inventors have unexpectedly found that the fusion proteins of the present invention may demonstrate an improved binding activity for target cells when the size of the spacer is selected so that (in use) the C-terminus of the TM and the N-terminus of the translocation component are separated from one another by 40-105 angstroms, preferably by 50-100 angstroms, and more preferably by 50-90 angstroms. In another embodiment, the preferred spacers have an amino acid sequence of 11-29 amino acid residues, preferably 15-27 amino acid residues, and more preferably 20-27 amino acid residues. Suitable spacers may be routinely identified and obtained according to Crasto, C. J. and Feng, J. A. (2000) May; 13(5); pp. 309-312—see also http://www.fccc.edu/research/labs/feng/limker.html.

In a preferred embodiment, the vector has a promoter selected from:

| Promoter | Induction agent | Typical induction condition |
|---|---|---|
| tac (hybrid) | IPTG | 0.2 mM (0.05-2.0 mM) |
| AraBAD | L-arabinose | 0.2% (0.002-0.4%) |
| T7-lac operator | IPTG | 0.2 mM (0.05-2.0 mM) |

The DNA construct of the present invention is preferably designed in silico, and then synthesised by conventional DNA synthesis techniques.

The above-mentioned DNA sequence information is optionally modified for codon-biasing according to the ultimate host cell (eg. *E. coli*) expression system that is to be employed.

The DNA backbone is preferably screened for any inherent nucleic acid sequence, which when transcribed and translated would produce an amino acid sequence corresponding to the protease cleave site encoded by the second peptide-coding sequence. This screening may be performed manually or with the assistance of computer software (eg. the MapDraw program by DNASTAR, Inc.).

According to a further embodiment of the present invention, there is provided a method of preparing a non-cytotoxic agent, comprising:— a. contacting a single-chain polypeptide fusion protein of the invention with a protease capable of cleaving the protease cleavage site;

b. cleaving the protease cleavage site, and thereby forming a di-chain fusion protein.

This aspect provides a di-chain polypeptide, which generally mimics the structure of clostridial holotoxin. In more detail, the resulting di-chain polypeptide typically has a structure wherein:— a. the first chain comprises the non-cytotoxic protease, or a fragment thereof, which protease or protease fragment is capable of cleaving a protein of the exocytic fusion apparatus of a target cell;

b. the second chain comprises the TM and the translocation domain that is capable of translocating the protease or protease fragment from within an endosome, across the endosomal membrane and into the cytosol of the target cell; and the first and second chains are disulphide linked together.

According to a further aspect of the present invention, there is provided use of a single chain or di-chain polypeptide of the invention, for the manufacture of a medicament for treating, preventing or ameliorating a medical condition selected from the group consisting of mucus hypersecretion, asthma, and/or chronic obstructive pulmonary disease, endocrine neoplasia including MEN, thyrotoxicosis and other diseases dependent on hypersecretions from the thyroid; acromegaly, hyperprolactinaemia, Cushings disease and other diseases dependent on anterior pituitary hypersecretion; hyperandrogenism, chronic anovulation and other diseases associated with polycystic ovarian syndrome, allergies (seasonal allergic rhinitis (hay fever), allergic conjunctivitis, vasomotor rhinitis and food allergy), eosinophilia, asthma, rheumatoid arthritis, systemic lupus erythematosus, discoid lupus erythematosus, ulcerative colitis, Crohn's disease, haemorrhoids, pruritus, glomerulonephritis, hepatitis, pancreatitis, gastritis, vasculitis, myocarditis, psoriasis, eczema, chronic radiation-induced fibrosis, lung scarring and other fibrotic disorders, mucus hypersecretion from mucus-secreting cells located in the alimentary tract, in particular located in the colon, myasthenia gravis, rheumatoid arthritis, systemic lupus erythematosus, discoid lupus erythematosus, organ transplant, tissue transplant, fluid transplant, Graves disease, thyrotoxicosis, autoimmune diabetes, haemolytic anaemia, thrombocytopenic purpura, neutropenia, chronic autoimmune hepatitis, autoimmune gastritis, pernicious anaemia, Hashimoto's thyroiditis, Addison's disease, Sjogren's syndrome, primary biliary cirrhosis, polymyositis, scleroderma, systemic sclerosis, pemphigus vulgaris, bullous pemphigoid, myocarditis, rheumatic carditis, glomerulonephritis (Goodpasture type), uveitis, orchitis, ulcerative colitis, vasculitis, atrophic gastritis, pernicious anaemia, type 1 diabetes mellitus, cardiovascular conditions and/or hypertension, and bone conditions such as osteopetrosis and osteoporosis.

According to a related aspect, there is provided a method of treating, preventing or ameliorating a medical condition or disease in a subject, comprising administering to said patient a therapeutically effective amount of a single chain or di-chain polypeptide of the invention, wherein the medical condition or disease is selected from the group consisting of mucus hypersecretion, asthma, and/or chronic obstructive pulmonary disease, endocrine neoplasia including MEN, thyrotoxicosis and other diseases dependent on hypersecretions from the thyroid; acromegaly, hyperprolactinaemia, Cushings disease and other diseases dependent on anterior pituitary hypersecretion; hyperandrogenism, chronic anovulation and other diseases associated with polycystic ovarian syndrome, allergies (seasonal allergic rhinitis (hay fever), allergic conjunctivitis, vasomotor rhinitis and food allergy), eosinophilia, asthma, rheumatoid arthritis, systemic lupus erythematosus, discoid lupus erythematosus, ulcerative colitis, Crohn's disease, haemorrhoids, pruritus, glomerulonephritis, hepatitis, pancreatitis, gastritis, vasculitis, myocarditis, psoriasis, eczema, chronic radiation-induced fibrosis, lung scarring and other fibrotic disorders, mucus hypersecretion from mucus-secreting cells located in the alimentary tract, in particular located in the colon, myasthenia gravis, rheumatoid arthritis, systemic lupus erythematosus, discoid lupus erythematosus, organ transplant, tissue transplant, fluid transplant, Graves disease, thyrotoxicosis, autoimmune diabetes, haemolytic anaemia, thrombocytopenic purpura, neutropenia, chronic autoimmune hepatitis, autoimmune gastritis, pernicious anaemia, Hashimoto's thyroiditis, Addison's disease, Sjogren's syndrome, primary biliary cirrhosis, polymyositis, scleroderma, systemic sclerosis, pemphigus vulgaris, bullous pemphigoid, myocarditis, rheumatic carditis, glomerulonephritis (Goodpasture type), uveitis, orchitis, ulcerative colitis, vasculitis, atrophic gastritis, pernicious anaemia, type 1 diabetes mellitus, cardiovascular conditions and/or hypertension, and bone conditions such as osteopetrosis and osteoporosis.

In use, the polypeptides of the present invention are typically employed in the form of a pharmaceutical composition in association with a pharmaceutical carrier, diluent and/or excipient, although the exact form of the composition may be tailored to the mode of administration. Administration is preferably to a mammal, more preferably to a human.

The polypeptides may, for example, be employed in the form of an aerosol or nebulisable solution for inhalation or a sterile solution for parenteral administration, intra-articular administration or intra-cranial administration.

For treating endocrine targets, i.v. injection, direct injection into gland, or aerosolisation for lung delivery are preferred; for treating inflammatory cell targets, i.v. injection, sub-cutaneous injection, or surface patch administration or aerosolisation for lung delivery are preferred; for treating exocrine targets, i.v. injection, or direct injection into or direct administration to the gland or aerosolisation for lung delivery are preferred; for treating immunological targets, i.v. injection, or injection into specific tissues eg. thymus, bone marrow, or lymph tissue are preferred; for treatment of cardiovascular targets, i.v. injection is preferred; and for treatment of bone targets, i.v. injection, or direct injection is preferred. In cases of i.v. injection, this should also include the use of pump systems. In the case of compositions for treating neuronal targets, spinal injection (eg. epidural or intrathecal) or indwelling pumps may be used.

The dosage ranges for administration of the polypeptides of the present invention are those to produce the desired therapeutic effect. It will be appreciated that the dosage range required depends on the precise nature of the components, the route of administration, the nature of the formulation, the age of the patient, the nature, extent or severity of the patient's condition, contraindications, if any, and the judgement of the attending physician.

Suitable daily dosages are in the range 0.0001-1 mg/kg, preferably 0.0001-0.5 mg/kg, more preferably 0.002-0.5 mg/kg, and particularly preferably 0.004-0.5 mg/kg. The unit dosage can vary from less that 1 microgram to 30 mg, but typically will be in the region of 0.01 to 1 mg per dose, which may be administered daily or preferably less frequently, such as weekly or six monthly.

A particularly preferred dosing regimen is based on 2.5 ng of fusion protein as the 1× dose per kg patient. In this regard, preferred dosages are in the range 1×–100×(ie. 2.5-250 ng). This dosage range is significantly lower (ie. at least 10-fold, typically 100-fold lower) than would be employed with other types of therapeutic molecules. Moreover, the above-mentioned difference is significantly magnified when the same comparison is made on a molar basis—this is because the fusion proteins of the present invention have a considerably greater molecular weight than the conventional 'small' molecule therapeutics.

Wide variations in the required dosage, however, are to be expected depending on the precise nature of the components, and the differing efficiencies of various routes of administration. For example, oral administration would be expected to require higher dosages than administration by intravenous injection.

Variations in these dosage levels can be adjusted using standard empirical routines for optimisation, as is well understood in the art.

Compositions suitable for injection may be in the form of solutions, suspensions or emulsions, or dry powders which are dissolved or suspended in a suitable vehicle prior to use.

Fluid unit dosage forms are typically prepared utilising a pyrogen-free sterile vehicle. The active ingredients, depending on the vehicle and concentration used, can be either dissolved or suspended in the vehicle.

Solutions may be used for all forms of parenteral administration, and are particularly used for intravenous injection. In preparing solutions the components can be dissolved in the vehicle, the solution being made isotonic if necessary by addition of sodium chloride and sterilised by filtration through a sterile filter using aseptic techniques before filling into suitable sterile vials or ampoules and sealing. Alternatively, if solution stability is adequate, the solution in its sealed containers may be sterilised by autoclaving.

Advantageously additives such as buffering, solubilising, stabilising, preservative or bactericidal, suspending or emulsifying agents and/or local anaesthetic agents may be dissolved in the vehicle.

Dry powders which are dissolved or suspended in a suitable vehicle prior to use may be prepared by filling presterilised drug substance and other ingredients into a sterile container using aseptic technique in a sterile area.

Alternatively the components (ie. agent plus inhibitor) and other ingredients may be dissolved in an aqueous vehicle, the solution is sterilized by filtration and distributed into suitable containers using aseptic technique in a sterile area. The product is then freeze dried and the containers are sealed aseptically.

Parenteral suspensions, suitable for intramuscular, subcutaneous or intradermal injection, are prepared in substantially the same manner, except that the sterile components are suspended in the sterile vehicle, instead of being dissolved and sterilisation cannot be accomplished by filtration. The components may be isolated in a sterile state or alternatively it may be sterilised after isolation, eg. by gamma irradiation.

Advantageously, a suspending agent for example polyvinylpyrrolidone is included in the composition/s to facilitate uniform distribution of the components.

Compositions suitable for administration via the respiratory tract include aerosols, nebulisable solutions or microfine powders for insufflation. In the latter case, particle size of less than 50 microns, especially less than 10 microns, is preferred. Such compositions may be made up in a conventional manner and employed in conjunction with conventional administration devices.

Definitions Section

Targeting Moiety (TM) means any chemical structure associated with an agent that functionally interacts with a Binding Site to cause a physical association between the agent and the surface of a target cell. In the context of the present invention, the target cell is any cell except a nociceptive sensory afferent. The term TM embraces any molecule (ie. a naturally occurring molecule, or a chemically/physically modified variant thereof) that is capable of binding to a Binding Site on the target cell, which Binding Site is capable of internalisation (eg. endosome formation)—also referred to as receptor-mediated endocytosis. The TM may possess an endosomal membrane translocation function, in which case separate TM and Translocation Domain components need not be present in an agent of the present invention.

The TM of the present invention binds (preferably specifically binds) to a target cell.

The term non-cytotoxic means that the protease molecule in question does not kill the target cell to which it has been re-targeted.

The protease of the present invention embraces all naturally-occurring non-cytotoxic proteases that are capable of cleaving one or more proteins of the exocytic fusion apparatus in eukaryotic cells.

The protease of the present invention is preferably a bacterial protease (or fragment thereof). More preferably the bacterial protease is selected from the genera *Clostridium* or *Neisseria* (eg. a clostridial L-chain, or a neisserial IgA protease preferably from *N. gonorrhoeae*).

The present invention also embraces modified non-cytotoxic proteases, which include amino acid sequences that do not occur in nature and/or synthetic amino acid residues, so long as the modified proteases still demonstrate the above-mentioned protease activity.

The protease of the present invention preferably demonstrates a serine or metalloprotease activity (eg. endopeptidase activity). The protease is preferably specific for a SNARE protein (eg. SNAP-25, synaptobrevin/VAMP, or syntaxin).

Particular mention is made to the protease domains of neurotoxins, for example the protease domains of bacterial neurotoxins. Thus, the present invention embraces the use of neurotoxin domains, which occur in nature, as well as recombinantly prepared versions of said naturally-occurring neurotoxins.

Exemplary neurotoxins are produced by clostridia, and the term clostridial neurotoxin embraces neurotoxins produced by *C. tetani* (TeNT), and by *C. botulinum* (BoNT) serotypes A-G, as well as the closely related BoNT-like neurotoxins produced by *C. baratii* and *C. butyricum*. The above-mentioned abbreviations are used throughout the present specification. For example, the nomenclature BoNT/A denotes the source of neurotoxin as BoNT (serotype A). Corresponding nomenclature applies to other BoNT serotypes.

The term L-chain fragment means a component of the L-chain of a neurotoxin, which fragment demonstrates a metalloprotease activity and is capable of proteolytically cleaving a vesicle and/or plasma membrane associated protein involved in cellular exocytosis.

A Translocation Domain is a molecule that enables translocation of a protease (or fragment thereof) into a target cell such that a functional expression of protease activity occurs within the cytosol of the target cell. Whether any molecule (eg. a protein or peptide) possesses the requisite translocation function of the present invention may be confirmed by any one of a number of conventional assays.

For example, Shone C. (1987) describes an in vitro assay employing liposomes, which are challenged with a test molecule. Presence of the requisite translocation function is confirmed by release from the liposomes of $K^+$ and/or labelled NAD, which may be readily monitored [see Shone C. (1987) Eur. J. Biochem; vol. 167(1): pp. 175-180].

A further example is provided by Blaustein R. (1987), which describes a simple in vitro assay employing planar phospholipid bilayer membranes. The membranes are challenged with a test molecule and the requisite translocation function is confirmed by an increase in conductance across said membranes [see Blaustein (1987) FEBS Letts; vol. 226, no. 1: pp. 115-120].

Additional methodology to enable assessment of membrane fusion and thus identification of Translocation Domains suitable for use in the present invention are provided by Methods in Enzymology Vol 220 and 221, Membrane Fusion Techniques, Parts A and B, Academic Press 1993.

The Translocation Domain is preferably capable of formation of ion-permeable pores in lipid membranes under conditions of low pH. Preferably it has been found to use only those portions of the protein molecule capable of pore-formation within the endosomal membrane.

The Translocation Domain may be obtained from a microbial protein source, in particular from a bacterial or viral protein source. Hence, in one embodiment, the Translocation Domain is a translocating domain of an enzyme, such as a bacterial toxin or viral protein.

It is well documented that certain domains of bacterial toxin molecules are capable of forming such pores. It is also known that certain translocation domains of virally expressed membrane fusion proteins are capable of forming such pores. Such domains may be employed in the present invention.

The Translocation Domain may be of a clostridial origin, namely the $H_N$ domain (or a functional component thereof). $H_N$ means a portion or fragment of the H-chain of a clostridial neurotoxin approximately equivalent to the amino-terminal half of the H-chain, or the domain corresponding to that fragment in the intact H-chain. It is preferred that the H-chain substantially lacks the natural binding function of the $H_C$ component of the H-chain. In this regard, the $H_C$ function may be removed by deletion of the $H_C$ amino acid sequence (either at the DNA synthesis level, or at the post-synthesis level by nuclease or protease treatment). Alternatively, the $H_C$ function may be inactivated by chemical or biological treatment. Thus, the H-chain is preferably incapable of binding to the Binding Site on a target cell to which native clostridial neurotoxin (ie. holotoxin) binds.

In one embodiment, the translocation domain is a $H_N$ domain (or a fragment thereof) of a clostridial neurotoxin. Examples of suitable clostridial Translocation Domains include:—

Botulinum type A neurotoxin—amino acid residues (449-871)
Botulinum type B neurotoxin—amino acid residues (441-858)
Botulinum type C neurotoxin—amino acid residues (442-866)
Botulinum type D neurotoxin—amino acid residues (446-862)
Botulinum type E neurotoxin—amino acid residues (423-845)
Botulinum type F neurotoxin—amino acid residues (440-864)
Botulinum type G neurotoxin—amino acid residues (442-863)
Tetanus neurotoxin—amino acid residues (458-879)

For further details on the genetic basis of toxin production in *Clostridium botulinum* and *C. tetani*, we refer to Henderson et al (1997) in *The Clostridia: Molecular Biology and Pathogenesis*, Academic press.

The term $H_N$ embraces naturally-occurring neurotoxin $H_N$ portions, and modified $H_N$ portions having amino acid sequences that do not occur in nature and/or synthetic amino acid residues, so long as the modified $H_N$ portions still demonstrate the above-mentioned translocation function.

Alternatively, the Translocation Domain may be of a non-clostridial origin (see Table 1). Examples of non-clostridial Translocation Domain origins include, but not be restricted to, the translocation domain of diphtheria toxin [O=Keefe et al., Proc. Natl. Acad. Sci. USA (1992) 89, 6202-6206; Silverman et al., J. Biol. Chem. (1993) 269, 22524-22532; and London, E. (1992) *Biochem. Biophys. Acta.*, 1112, pp. 25-51], the translocation domain of *Pseudomonas* exotoxin type A [Prior et al. Biochemistry (1992) 31, 3555-3559], the translocation domains of anthrax toxin [Blanke et al. Proc. Natl. Acad. Sci. USA (1996) 93, 8437-8442], a variety of fusogenic or hydrophobic peptides of translocating function [Plank et al. J. Biol. Chem. (1994) 269, 12918-12924; and Wagner et al (1992) *PNAS*, 89, pp. 7934-7938], and amphiphilic peptides [Murata et al (1992) *Biochem.*, 31, pp. 1986-1992]. The Translocation Domain may mirror the Translocation Domain present in a naturally-occurring protein, or may include amino acid variations so long as the variations do not destroy the translocating ability of the Translocation Domain.

Particular examples of viral Translocation Domains suitable for use in the present invention include certain translocating domains of virally expressed membrane fusion proteins. For example, Wagner et al. (1992) and Murata et al. (1992) describe the translocation (ie. membrane fusion and vesiculation) function of a number of fusogenic and amphiphilic peptides derived from the N-terminal region of influenza virus haemagglutinin. Other virally expressed membrane fusion proteins known to have the desired translocating activity are a translocating domain of a fusogenic peptide of Semliki Forest Virus (SFV), a translocating domain of vesicular stomatitis virus (VSV) glycoprotein G, a translocating domain of SER virus F protein and a translocating domain of Foamy virus envelope glycoprotein. Virally encoded Aspike proteins have particular application in the context of the present invention, for example, the E1 protein of SFV and the G protein of the G protein of VSV.

Use of the Translocation Domains listed in Table 1 includes use of sequence variants thereof. A variant may comprise one or more conservative nucleic acid substitutions and/or nucleic acid deletions or insertions, with the proviso that the variant possesses the requisite translocating function. A variant may also comprise one or more amino acid substitutions and/or amino acid deletions or insertions, so long as the variant possesses the requisite translocating function.

TABLE 1

| Translocation domain source | Amino acid Residues | References |
|---|---|---|
| Diphtheria toxin | 194-380 | Silverman et al., 1994, J. Biol. Chem. 269, 22524-22532 London E., 1992, Biochem. Biophys. Acta., 1113, 25-51 |
| Domain II of *pseudomonas* exotoxin | 405-613 | Prior et al., 1992, Biochemistry 31, 3555-3559 Kihara & Pastan, 1994, Bioconj Chem. 5, 532-538 |
| Influenza virus haemagglutinin | GLFGAIAGFIENGW EGMIDGWYG, and Variants thereof | Plank et al., 1994, J. Biol. Chem. 269, 12918-12924 Wagner et al., 1992, PNAS, 89, 7934-7938 Murata et al., 1992, Biochemistry 31, 1986-1992 |
| Semliki Forest virus fusogenic protein | Translocation domain | Kielian et al., 1996, J Cell Biol. 134(4), 863-872 |
| Vesicular Stomatitis virus glycoprotein G | 118-139 | Yao et al., 2003, Virology 310(2), 319-332 |
| SER virus F protein | Translocation domain | Seth et al., 2003, J Virol 77(11) 6520-6527 |
| Foamy virus envelope glycoprotein | Translocation domain | Picard-Maureau et al., 2003, J Virol. 77(8), 4722-4730 |

SEQ ID NOs

SEQ ID1 DNA sequence of the LC/A
SEQ ID2 DNA sequence of the $H_N$/A
SEQ ID3 DNA sequence of the LC/B
SEQ ID4 DNA sequence of the $H_N$/B
SEQ ID5 DNA sequence of the LC/C
SEQ ID6 DNA sequence of the $H_N$/C
SEQ ID7 DNA sequence of the CP PAR1-B linker
SEQ ID8 DNA sequence of the CP PTH-C linker
SEQ ID9 DNA sequence of the CP PAR1-B fusion
SEQ ID10 Protein sequence of the CP PAR1-B fusion
SEQ ID11 DNA sequence of the CP PTH-C fusion
SEQ ID12 Protein sequence of the CP PTH-C fusion
SEQ ID13 DNA sequence of the CP RGD-C linker
SEQ ID14 DNA sequence of the CP RGD-C fusion
SEQ ID15 Protein sequence of the CP RGD-C fusion
SEQ ID16 DNA sequence of the CP cyclicRGD-C linker
SEQ ID17 DNA sequence of the CP cyclicRGD-C fusion
SEQ ID18 Protein sequence of the CP cyclicRGD-C fusion
SEQ ID19 DNA sequence of the CP THALWHT-C linker
SEQ ID20 DNA sequence of the CP THALWHT-C fusion
SEQ ID21 Protein sequence of the CP THALWHT-C fusion
SEQ ID22 DNA sequence of the CP cyclicTHALWHT-C linker
SEQ ID23 DNA sequence of the CP cyclicTHALWHT-C fusion SEQ ID24 Protein sequence of the CP cyclicTHALWHT-C fusion
SEQ ID25 DNA sequence of the CP ANP-C linker
SEQ ID26 DNA sequence of the CP ANP-C fusion
SEQ ID27 Protein sequence of the CP ANP-C fusion
SEQ ID28 DNA sequence of the CP VIP-C linker
SEQ ID29 DNA sequence of the CP VIP-C fusion
SEQ ID30 Protein sequence of the CP VIP-C fusion
SEQ ID31 DNA sequence of the CP Gastrin releasing peptide-C linker
SEQ ID32 DNA sequence of the CP Gastrin releasing peptide-C fusion
SEQ ID33 Protein sequence of the CP Gastrin releasing peptide-C fusion

EXAMPLES

Example 1

Preparation of LC/B and $H_N$/B Backbone Clones

The following procedure creates the LC and $H_N$ fragments for use as the component backbone for multidomain fusion expression. This example is based on preparation of a serotype B based clone (SEQ ID3 and SEQ ID4), though the procedures and methods are equally applicable to the other serotypes (illustrated by the sequence listing for serotype A (SEQ ID1 and SEQ ID2) and serotype C (SEQ ID5 and SEQ ID6)).

Preparation of Cloning and Expression Vectors pCR 4 (Invitrogen) is the chosen standard cloning vector chosen due to the lack of restriction sequences within the vector and adjacent sequencing primer sites for easy construct confirmation. The expression vector is based on the pMAL (NEB) expression vector, which has the desired restriction sequences within the multiple cloning site in the correct orientation for construct insertion (BamHI-SalI-PstI-HindIII). A fragment of the expression vector has been removed to create a non-mobilisable plasmid and a variety of different fusion tags have been inserted to increase purification options.

Preparation of Protease (eg. LC/B) Insert

The LC/B (SEQ ID3) is created by one of two ways:

The DNA sequence is designed by back translation of the LC/B amino acid sequence (obtained from freely available database sources such as GenBank (accession number P10844) or Swissprot (accession locus BXB_CLOBO) using one of a variety of reverse translation software tools (for example EditSeq best *E. coli* reverse translation (DNASTAR Inc.), or Backtranslation tool v2.0 (Entelechon)). BamHI/SalI recognition sequences are incorporated at the 5' and 3' ends respectively of the sequence maintaining the correct reading frame. The DNA sequence is screened (using software such as MapDraw, DNASTAR Inc.) for restriction enzyme cleavage sequences incorporated during the back translation. Any cleavage sequences that are found to be common to those required by the cloning system are removed manually from the proposed coding sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, Sep. 13, 2004). This optimised DNA sequence containing the LC/B open reading frame (ORF) is then commercially synthesized (for example by Entelechon, Geneart or Sigma-Genosys) and is provided in the pCR 4 vector.

The alternative method is to use PCR amplification from an existing DNA sequence with BamHI and SalI restriction enzyme sequences incorporated into the 5' and 3' PCR primers respectively. Complementary oligonucleotide primers are chemically synthesised by a Supplier (for example MWG or Sigma-Genosys) so that each pair has the ability to hybridize to the opposite strands (3' ends pointing "towards" each other) flanking the stretch of *Clostridium* target DNA, one oligonucleotide for each of the two DNA strands. To generate a PCR product the pair of short oligonucleotide primers specific for the *Clostridium* DNA sequence are mixed with the *Clostridium* DNA template and other reaction components and placed in a machine (the 'PCR machine') that can change the incubation temperature of the reaction tube automatically, cycling between approximately 94° C. (for denaturation), 55° C. (for oligonucleotide annealing), and 72° C. (for synthesis). Other reagents required for amplification of a PCR product include a DNA polymerase (such as Taq or Pfu polymerase), each of the four nucleotide dNTP building blocks of DNA in equimolar amounts (50-200 µM) and a buffer appropriate for the enzyme optimised for Mg2+ concentration (0.5-5 mM).

The amplification product is cloned into pCR 4 using either, TOPO TA cloning for Taq PCR products or Zero Blunt TOPO cloning for Pfu PCR products (both kits commercially available from Invitrogen). The resultant clone is checked by sequencing. Any additional restriction sequences that are not compatible with the cloning system are then removed using site directed mutagenesis (for example using Quickchange (Stratagene Inc.)).

Preparation of Translocation (eg. $H_N$) Insert

The $H_N$/B (SEQ ID4) is created by one of two ways:

The DNA sequence is designed by back translation of the $H_N$/B amino acid sequence (obtained from freely available database sources such as GenBank (accession number P10844) or Swissprot (accession locus BXB_CLOBO)) using one of a variety of reverse translation software tools (for example EditSeq best *E. coli* reverse translation (DNASTAR Inc.), or Backtranslation tool v2.0 (Entelechon)). A PstI restriction sequence added to the N-terminus and XbaI-stop codon-HindIII to the C-terminus ensuring the correct reading frame in maintained. The DNA sequence is screened (using software such as MapDraw, DNASTAR Inc.) for restriction enzyme cleavage sequences incorporated during the back translation. Any sequences that are found to be common to those required by the cloning system are removed manually from the proposed coding sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, Sep. 13, 2004). This optimised DNA sequence is then commercially synthesized (for example by Entelechon, Geneart or Sigma-Genosys) and is provided in the pCR 4 vector.

The alternative method is to use PCR amplification from an existing DNA sequence with PstI and XbaI-stop codon-HindIII restriction enzyme sequences incorporated into the 5' and 3' PCR primers respectively. The PCR amplification is performed as described above. The PCR product is inserted into pCR 4 vector and checked by sequencing. Any additional restriction sequences that are not compatible with the cloning system are then removed using site directed mutagenesis (for example using Quickchange (Stratagene Inc.)).

Example 2

Preparation of a LC/B-PAR1-H$_N$/B Fusion Protein

Preparation of Linker-PAR1-Spacer Insert

The LC-$H_N$ linker can be designed from first principle, using the existing sequence information for the linker as the template. For example, the serotype B linker defined as the inter-domain polypeptide region that exists between the cysteines of the disulphide bridge between LC and $H_N$ within which proteolytic activation occurs. This sequence information is freely available from available database sources such as GenBank (accession number P10844) or Swissprot (accession locus BXB_CLOBO). It is into this linker that an Enterokinase site, PAR1 and spacer are incorporated and using one of a variety of reverse translation software tools (for example EditSeq best *E. coli* reverse translation (DNASTAR Inc.), or Backtranslation tool v2.0 (Entelechon)), the DNA sequence encoding the linker-ligand-spacer region is determined. Restriction site are then incorporated into the DNA sequence and can be arranged as BamHI-SalI-linker-protease site-PAR1-NheI-spacer-SpeI-PstI-XbaI-stop codon-HindIII (SEQ ID7). It is important to ensure the correct reading frame is maintained for the spacer, PAR1 and restriction sequences and that the XbaI sequence is not preceded by the bases, TC which would result on DAM methylation. The DNA sequence is screened for restriction sequence incorporated and any additional sequences are removed manually from the remaining sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, Sep. 13, 2004). This optimised DNA sequence is then commercially synthesized (for example by Entelechon, Geneart or Sigma-Genosys) and is provided in the pCR 4 vector.

Preparation of the LC/B-PAR1-$H_N$/B Fusion

In order to create the LC-linker-PAR1-spacer-$H_N$ construct (SEQ ID9), the pCR 4 vector encoding the linker (SEQ ID7) is cleaved with BamHI+SalI restriction enzymes. This cleaved vector then serves as the recipient vector for insertion and ligation of the LC/B DNA (SEQ ID3) cleaved with BamHI+SalI. The resulting plasmid DNA is then cleaved with PstI+XbaI restriction enzymes and serves as the recipient vector for the insertion and ligation of the $H_N$/B DNA (SEQ ID4) cleaved with PstI+XbaI. The final construct contains the LC-linker-PAR1-spacer-$H_N$ ORF (SEQ ID9) for transfer into expression vectors for expression to result in a fusion protein of the sequence illustrated in SEQ ID10.

Example 3

Preparation LC/C-PTH-$H_N$/C Fusion Protein

The LC-$H_N$ linker can be designed using the methods described in example two but using the C serotype linker arranged as BamHI-Sail-linker-protease site-PTH-NheI-spacer-SpeI-PstI-XbaI-stop codon-HindIII (SEQ ID8). The LC/C-PTH-$H_N$/C fusion is then assembled using the LC/C (SEQ ID5) and $H_N$/C (SEQ ID6) made using the methods described in example one and constructed using methods described in example two. The final construct contains the LC-linker-PTH-spacer-$H_N$ ORF (SEQ ID 11) for transfer into expression vectors for expression to result in a fusion protein of the sequence illustrated in SEQ ID 12.

Example 4

Preparation and Purification of LC/C-RGD-$H_N$/C Fusion Protein

The LC-$H_N$ linker is designed using the methods described in Example 2 but using the C serotype linker arranged as BamHI-Sail-linker-protease site-RGD-NheI-spacer-SpeI-PstI-XbaI-stop codon-HindIII (SEQ ID 13). The LC/C-RGD-$H_N$/C fusion is then assembled using the LC/C (SEQ ID 5) and $H_N$/C (SEQ ID 6) made using the methods described in Example 1 and constructed using methods described in Example 2. The final construct contains the LC-linker-RGD-spacer-$H_N$ ORF (SEQ ID 14) for transfer into expression vectors for expression to result in a fusion protein of the sequence illustrated in SEQ ID15. The resultant expression plasmid, pMAL LC/C-RGD-$H_N$/C is transformed into *E. coli* BL21 for recombinant protein expression.

Expression of LC/C-RGD-$H_N$/C Fusion Protein

Expression of the LC/C-RGD-$H_N$/C fusion protein is achieved using the following protocol. Inoculate 100 ml of modified TB containing 0.2% glucose and 100 μg/ml ampicillin in a 250 ml flask with a single colony from the LC/C-RGD-$H_N$/C expression strain. Grow the culture at 37° C., 225 rpm for 16 hours. Inoculate 1 L of modified TB containing 0.2% glucose and 100 μg/ml ampicillin in a 2 L flask with 10 ml of overnight culture. Grow cultures at 37° C. until an approximate $OD_{600nm}$ of 0.5 is reached at which point reduce the temperature to 16° C. After 1 hour induce the cultures with 1 mM IPTG and grow at 16° C. for a further 16 hours. FIG. 1 demonstrates the expressed protein in *E. coli* as analysed by SDS-PAGE.

Purification of LC/C-RGD-$H_N$/C Fusion Protein

Defrost falcon tube containing 25 ml 50 mM HEPES pH 7.2 200 mM NaCl and approximately 10 g of *E. coli* BL21 cell paste. Sonicate the cell paste on ice 30 seconds on, 30 seconds off for 10 cycles at a power of 22 microns ensuring the sample remains cool. Spin the lysed cells at 18 000 rpm, 4° C. for 30 minutes. Load the supernatant onto a 0.1 M $NiSO_4$ charged Chelating column (20-30 ml column is sufficient) equilibrated with 50 mM HEPES pH 7.2 200 mM NaCl. Using a step gradient of 10 and 40 mM imidazole, wash away the non-specific bound protein and elute the fusion protein with 100 mM imidazole. Dialyse the eluted fusion protein against 5 L of 50 mM HEPES pH 7.2 200 mM NaCl at 4° C. overnight and measure the OD of the dialysed fusion protein. Add 1 unit of factor Xa per 100 μg fusion protein and incubate at 25° C. static overnight. Load onto a 0.1 M $NiSO_4$ charged Chelating column (20-30 ml column is sufficient) equilibrated with 50 mM HEPES pH 7.2 200 mM NaCl. Wash column to baseline with 50 mM HEPES pH 7.2 200 mM NaCl. Using a step gradient of 10 and 40 mM imidazole, wash away the non-specific bound protein and elute the fusion protein with 100 mM imidazole. Dialyse the eluted fusion protein against 5 L of 50 mM HEPES pH 7.2 200 mM NaCl at 4° C. overnight and concentrate the fusion to about 2 mg/ml, aliquot sample and freeze at −20° C. Test purified protein using OD, BCA and purity analysis. FIG. 2 demonstrates the purified protein as analysed by SDS-PAGE.

Example 5

Preparation LC/C-CyclicRGD-$H_N$/C Fusion Protein

The LC-$H_N$ linker can be designed using the methods described in Example 2 but using the C serotype linker arranged as BamHI-SalI-linker-protease site-cyclicRGD-NheI-spacer-SpeI-PstI-XbaI-stop codon-HindIII (SEQ ID16). The LC/C-cyclicRGD-$H_N$/C fusion is then assembled using the LC/C (SEQ ID5) and $H_N$/C (SEQ ID6) made using the methods described in Example 1 and constructed using methods described in Example 2. The final construct contains the LC-linker-cyclicRGD-spacer-$H_N$ ORF (SEQ ID17) for transfer into expression vectors for expression to result in a fusion protein of the sequence illustrated in SEQ ID18. The resultant expression plasmid, pMAL LC/C-cyclicRGD-$H_N$/C was transformed into *E. coli* BL21 for recombinant protein expression. Expression of the fusion protein was carried out as described in Example 4. FIG. 1 demonstrates the protein expressed in *E. coli* as analysed by SDS-PAGE.

Example 6

Preparation LC/C-THALWHT-$H_N$/C Fusion Protein

The LC-$H_N$ linker can be designed using the methods described in Example 2 but using the C serotype linker arranged as BamHI-SalI-linker-protease site-THALWHT-NheI-spacer-SpeI-PstI-XbaI-stop codon-HindIII (SEQ ID19). The LC/C-THALWHT-$H_N$/C fusion is then assembled using the LC/C (SEQ ID5) and $H_N$/C (SEQ ID6) made using the methods described in Example 1 and constructed using methods described in Example 2. The final construct contains the LC-linker-THALWHT-spacer-$H_N$ ORF (SEQ ID20) for transfer into expression vectors for expression to result in a fusion protein of the sequence illustrated in SEQ ID21. Expression of the fusion protein was carried out as described in Example 4. FIG. 1 demonstrates the protein expressed in *E. coli* as analysed by SDS-PAGE.

The THALWHT peptide sequence given in this Example (SEQ IDs 19, 20 and 21) can be exchanged with another peptide sequence found by phage display techniques. For example, LEBP-1 (QPFMQCLCLIYDASC), LEBP-2 (RN-VPPIFNDVYWIAF) and LEBP-3 (VFRVRPWYQSTSQS) (Wu et al., 2003); CDSAFVTVDWGRSMSLC (Florea et al., 2003); SERSMNF, YGLPHKF, PSGAARA, LPHKSMP, LQHKSMP (Writer et al., 2004); FSLSKPP, HSMQLST and STQAMFQ peptides (Rahim et al., 2003).

Example 7

Preparation LC/C-CyclicTHALWHT-$H_N$/C Fusion Protein

The LC-$H_N$ linker can be designed using the methods described in Example 2 but using the C serotype linker arranged as BamHI-SalI-linker-protease site-cyclicTHAL-WHT-NheI-spacer-SpeI-PstI-XbaI-stop codon-Hind III (SEQ ID22). The LC/C-cyclicTHALWHT-$H_N$/C fusion is then assembled using the LC/C (SEQ ID5) and $H_N$/C (SEQ ID6) made using the methods described in example one and constructed using methods described in Example 2. The final construct contains the LC-linker-cyclicTHALWHT-spacer-$H_N$ ORF (SEQ ID23) for transfer into expression vectors for expression to result in a fusion protein of the sequence illustrated in SEQ ID24. Expression of the fusion protein was carried out as described in Example 4. FIG. 1 demonstrates the protein expressed in *E. coli* as analysed by SDS-PAGE.

The THALWHT peptide sequence given in this Example (SEQ IDs 19, 20 and 21) can be exchanged with another peptide sequence found by phage display techniques. For example, LEBP-1 (QPFMQCLCLIYDASC), LEBP-2 (RN-VPPIFNDVYWIAF) and LEBP-3 (VFRVRPWYQSTSQS) (Wu et al., 2003); CDSAFVTVDWGRSMSLC (Florea et al., 2003); SERSMNF, YGLPHKF, PSGAARA, LPHKSMP, LQHKSMP (Writer et al., 2004); FSLSKPP, HSMQLST and STQAMFQ peptides (Rahim et al., 2003).

Example 8

Preparation LC/C-ANP-$H_N$/C Fusion Protein

The LC-$H_N$ linker can be designed using the methods described in Example 2 but using the C serotype linker arranged as BamHI-SalI-linker-protease site-ANP-NheI-spacer-SpeI-PstI-XbaI-stop codon-HindIII (SEQ ID25). The LC/C-ANP-$H_N$/C fusion is then assembled using the LC/C (SEQ ID5) and $H_N$/C (SEQ ID6) made using the methods described in Example 1 and constructed using methods described in Example 2. The final construct contains the LC-linker-ANP-spacer-$H_N$ ORF (SEQ ID26) for transfer into expression vectors for expression to result in a fusion protein of the sequence illustrated in SEQ ID27.

Example 9

Preparation LC/C-VIP-$H_N$/C Fusion Protein

The LC-$H_N$ linker can be designed using the methods described in Example 2 but using the C serotype linker arranged as BamHI-SalI-linker-protease site-VIP-NheI-spacer-SpeI-PstI-XbaI-stop codon-HindIII (SEQ ID28). The LC/C-VIP-$H_N$/C fusion is then assembled using the LC/C (SEQ ID5) and $H_N$/C (SEQ ID6) made using the methods described in Example 1 and constructed using methods described in Example 2. The final construct contains the LC-linker-VIP-spacer-$H_N$ ORF (SEQ ID29) for transfer into expression vectors for expression to result in a fusion protein of the sequence illustrated in SEQ ID30.

The VIP sequence given in SEQ ID28 could be replaced with VIP analogue or agonist sequences. For example, $[R^{15,20,21}, L^{17}]$-VIP or $[R^{15,20,21}, L^{17}]$-VIP-GRR (Kashimoto et al., 1996; Onoue et al., 2004), $[A^{2,8,9,16,19,24}]$-VIP or $[A^{2,8,9,16,19,24,25}]$-VIP (Igarashi et al., 2005).

Example 10

Preparation LC/C-Gastrin Releasing Peptide-$H_N$/C Fusion Protein

The LC-$H_N$ linker can be designed using the methods described in Example 2 but using the C serotype linker arranged as BamHI-SalI-linker-protease site-gastrin releasing peptide-NheI-spacer-SpeI-PstI-XbaI-stop codon-HindIII (SEQ ID34). The LC/C-gastrin releasing peptide-$H_N$/C fusion is then assembled using the LC/C (SEQ ID5) and $H_N$/C (SEQ ID6) made using the methods described in Example 1 and constructed using methods described in Example 2. The final construct contains the LC-linker-gastrin releasing peptide-spacer-$H_N$ ORF (SEQ ID35) for transfer into expression vectors for expression to result in a fusion protein of the sequence illustrated in SEQ ID36.

Example 11

Assessment of Functionality of the LC/C-RGD-$H_N$/C Fusion Protein

The functionality of the TM component of the LC/C-RGD-$H_N$/C fusion protein (prepared according to Example 4) is assessed by a ligand binding assay. To facilitate assessment of ligand binding, an RGD binding peptide is synthesised in a biotinylated and non-biotinylated form. Binding of the fusion protein is determined by a competition assay with the biotinylated form. Briefly, NCI-H292 cells are plated into 96 well plates and viable cultures established. Cells and solutions are pre-chilled to 4° C. and solutions are prepared in cell feeding medium-plus-HEPES (50 mM). Prior to treatment, media is removed from the cells and replaced with media-plus-HEPES (500 μl per well), which is then also removed. Labelled ligand, at ×2 the required concentration, is added to all wells (50 μl per well). The fusion protein, at ×2 the required concentration, is then added to wells (50 μl per well). After 1 hour at 4° C., the media is removed and replaced with media+HEPES (100 μl per well). This media is removed and replaced with media+HEPES (100 μl per well). Cells are lysed with 100 μl per well PBS-Tween 0.1% for 5 mins at 4° C. PBS-Tween is removed and cells are washed with media+HEPES (100 μl per well). This media is removed and replaced with 100 μl PBS+100 μl streptavidin-HRP per well. Cells are incubated at RTP for 20 mins. The PBS+streptavidin is removed and the cells are washed with PBS-Tween. 100 μl per well of TMB is added and the cells are incubated at 37° C. for 10 mins. 50 μl per well 2M $H_2SO_4$ is added and the plate read at 450 nm. Using this methodology, the ability of the TM component of the LC/C-RGD-$H_N$/C fusion protein to bind to the cell surface is confirmed.

Using the methodology outlined in Example 4, LC/C-RGD-$H_N$/C, LC/C-cyclicRGD-$H_N$/C, LC/C-THALWHT-$H_N$/C and LC/C-cyclicTHALWHT-$H_N$/C fusion proteins were expressed in E. coli BL21 cells. Briefly, 1 L of TB media containing 0.2% glucose and 100 μg/ml ampicillin was inoculated with 10 ml of starter culture. Cultures were grown at 37° C. until an approximate $OD_{600nm}$ of 0.5 was reached at which point the temperature was reduced to 16° C. After 1 hour the cultures were induced with 1 mM IPTG and grown for a further 16 hours.

Lane 1, LC/C-THALWHT-$H_N$/C;
Lane 2, LC/C-RGD-$H_N$/C;
Lane 3, LC/C-cyclicTHALWHT-$H_N$/C;
Lane 4, LC/C-cyclicRGD-$H_N$/C.

Figure 1:
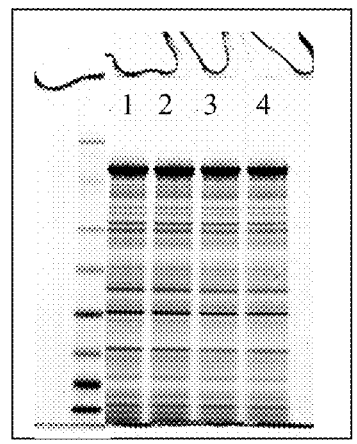
FIG. 1—Expression of LC/C-RGD-$H_N$/C, LC/C-cyclicRGD-$H_N$/C, LC/C-THALWHT-$H_N$/C and LC/C-cyclicTHALWHT-$H_N$/C fusion proteins in E. coli.
Figure 2:
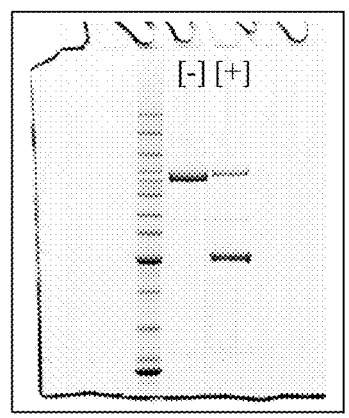

FIG. 2—Purification of a LC/C-RGD-$H_N$/C fusion protein

Using the methodology outlined in Example 5, a LC/C-RGD-$H_N$/C fusion protein was purified from E. coli BL21 cells. Briefly, the soluble products obtained following cell disruption were applied to a nickel-charged affinity capture column. Bound proteins were eluted with 100 mM imidazole, treated with Factor Xa to activate the fusion protein and remove the maltose-binding protein (MBP) tag, then re-applied to a second nickel-charged affinity capture column. Samples from the purification procedure were assessed by SDS-PAGE. The final purified material in the absence and presence of reducing agent is identified in the lanes marked [−] and [+] respectively.

REFERENCES

Florea et al., (2003) J. Drug Targeting 11: 383-390
Jost et al., (2001) FEBS lett. 489: 263-269
Lee et al., (2001) Eur. J. Biochem. 268: 2004-2012
Mathias et al., (1994) J. Virol. 68: 6811-6814
Rahim et al., (2003) Biotechniques 35: 317-324
Roivaninen et al., (1991) J. Virol. 65: 4735-4740
Ruoslahti (1996) Ann. Rev. Cell Dev. Biol. 12: 697-715
Schneider et al., (1999) FEBS lett. 458: 329-332
Writer et al., (2004) J. Drug Targeting 12: 185-193
Wu et al., (2003) Gene Ther. 10: 1429-1436

The invention claimed is:

1. A single chain, polypeptide fusion protein, comprising:
   a) a non-cytotoxic protease that cleaves a protein of the exocytic fusion apparatus of a target cell;
   b) a Targeting Moiety that binds to a Binding Site on the target cell, which Binding Site undergoes endocytosis to be incorporated into an endosome within the target cell;
   c) a protease cleavage site at which site the fusion protein is cleavable by a protease, wherein the protease cleavage site is located between the non-cytotoxic protease and the Targeting Moiety; and
   d) a translocation domain that translocates the non-cytotoxic protease from within an endosome, across the endosomal membrane and into the cytosol of the target cell;
   wherein the Targeting Moiety is located between the protease cleavage site and the translocation domain; and
   wherein the non-cytotoxic protease forms a disulphide bond with the translocation domain of the fusion protein, wherein the amino acid residue of the non-cytotoxic protease that forms the first part of the disulphide bond is located within the last 20 C-terminal amino acid residues of the non-cytotoxic protease, and the amino acid residue of the translocation domain that forms the second part of the disulphide bond is located within the first 20 N-terminal amino acid residues of the translocation domain.

2. The fusion protein according to claim 1, wherein the Targeting Moiety and the protease cleavage site are separated by at most 10 amino acid residues, by at most 5 amino acid residues, or by zero amino acid residues.

3. The fusion protein according to claim 1, wherein the non-cytotoxic protease is a clostridial neurotoxin L-chain.

4. The fusion protein according to claim 1, wherein the translocation domain is the $H_N$ domain of a clostridial neurotoxin.

5. The fusion protein according to claim 1, wherein the Targeting Moiety comprises at most 50 amino acid residues, at most 40 amino acid residues, or at most 20 amino acid residues.

6. The fusion protein according to claim 1, wherein the Targeting Moiety comprises a PAR ligand or the ligand PAR-1.

7. The fusion protein according to claim 1, wherein the Targeting Moiety comprises a ligand that binds to PTH-1, a PTH peptide, a linear or cyclic integrin-binding sequence; or a triple Arg-Gly-Asp (RGD) binding sequence.

8. The fusion protein according to claim 1, wherein the fusion protein comprises one or more purification tags.

9. The fusion protein according to claim 8, wherein the one or more purification tags are present at the N-terminal and/or C-terminal end of the fusion protein.

10. The fusion protein according to claim 9, wherein the one or more purification tags are joined to the fusion protein by a peptide spacer molecule.

11. The fusion protein according to claim 8, wherein the one or more purification tags are joined to the fusion protein by a peptide spacer molecule.

12. The fusion protein according to claim 1, wherein the translocation domain is separated from the Targeting Moiety by a peptide spacer molecule.

13. A nucleic acid encoding the polypeptide fusion protein of claim 1.

14. A DNA vector, which comprises a promoter, the nucleic acid of claim 13, and a terminator, wherein said nucleic acid is located downstream of the promoter, and said terminator is located downstream of the nucleic acid.

15. A nucleic acid which is complementary to the nucleic acid of claim 13.

16. A method for preparing a single-chain polypeptide fusion protein, comprising expressing the nucleic acid sequence of claim 13 in a host cell.

17. A method of preparing a di-chain fusion protein, comprising:
   a) contacting a single-chain polypeptide fusion protein according to claim 1 with a protease capable of cleaving the protease cleavage site;
   b) cleaving the protease cleavage site; and
   thereby forming the di-chain fusion protein.

18. A di-chain fusion protein obtained by the method of claim 17, wherein the di-chain fusion protein comprises a first chain and a second chain, and wherein a) the first chain comprises the non-cytotoxic protease, or a fragment thereof, which protease or protease fragment cleaves a protein of the exocytic fusion apparatus of a target cell; and, b) the second chain comprises the Targeting Moiety and the translocation domain, wherein the translocation domain translocates the protease or protease fragment from within an endosome, across the endosomal membrane and into the cytosol of the target cell; and the first and second chains are disulphide linked together.

19. A composition comprising a fusion protein according to claim 1.

20. The fusion protein of claim 1, wherein the Targeting Moiety binds to a cell selected from the group consisting of: a mucus secreting cell; a neuronal cell controlling or directing mucus secretion; an endocrine cell; an inflammatory cell; an exocrine cell; an immunological cell; a cardiovascular cell; and a bone cell.

21. The fusion protein of claim 1, wherein the Targeting Moiety comprises a ligand selected from the group consisting of: TFLLR; PAR-1; PTH; VIP; a VIP analogue selected from the group consisting of $[R^{15, 20, 21}, L^{17}]$-VIP, $[R^{15, 20, 21}, L^{17}]$-VIP-GRR, $[A^{2, 8, 9, 16, 19, 24}]$-VIP and $[A^{2, 8, 9, 16, 19, 24, 25}]$-VIP; a VIP agonist; beta$_2$ adrenoreceptor agonists; gastrin-releasing peptide (GRP); calcitonin gene related peptide (CGRP); thyroid-stimulating hormone (TSH); insulin; insulin-like growth factor; TSH-releasing hormone (protirelin); FSH/LH-releasing hormone (gonadorelin); corticotrophin releasing hormone (CRH); adenocorticotrophic hormone (ACTH); pituitary adenyl cyclase activating peptide; a ligand to the C4 domain of the Fc IgE; a ligand to the C3a/C4a-R complement receptor; an antigen reactive towards the CR4 complement receptor; macrophage stimulating factor; an antigen associated with the iC3b complement receptor; IL8; Epstein Barr virus fragment/surface feature; thrombin; thrombin receptor agonist peptide (TRAP); GP1b surface antigen-recognizing antibodies; calcitonin; the osteoclast differentiation factors TRANCE, RANKL, and OPGL; a linear or cyclic peptide selected from the group consisting of: THALWHT, LEBP-1 (QPFMQ-CLCLIYDASC), LEBP-2 (RNVPPIFNDVYWIAF), LEBP-3 (VFRVRPWYQSTSQS), CDSAFVTVD-WGRSMSLC, SERSMNF, YGLPHKF, PSGAARA, LPH-KSMP, LQHKSMP, FSLSKPP, HSMQLST, and STQAMFQ; and ANP.

22. The fusion protein of claim 1, wherein the Targeting Moiety and the protease cleavage site are separated by at most 5 amino acid residues.

23. The fusion protein of claim 1, wherein the Targeting Moiety comprises at most 20 amino acid residues.

24. A single chain, polypeptide fusion protein, comprising:
a) a non-cytotoxic protease that cleaves a protein of the exocytic fusion apparatus of a target cell;
b) a Targeting Moiety that binds to a Binding Site on the target cell, which Binding Site undergoes endocytosis to be incorporated into an endosome within the target cell;
c) a protease cleavage site at which site the fusion protein is cleavable by a protease, wherein the protease cleavage site is located between the non-cytotoxic protease and the Targeting Moiety;
d) a translocation domain that translocates the non-cytotoxic protease from within an endosome, across the endosomal membrane and into the cytosol of the target cell;
wherein the Targeting Moiety is located between the protease cleavage site and the translocation domain; and
and wherein the non-cytotoxic protease forms a disulphide bond with the Targeting Moiety of the fusion protein, wherein the amino acid residue of the non-cytotoxic protease that forms the first part of the disulphide bond is located within the last 20 C-terminal amino acid residues of the non-cytotoxic protease, and the amino acid residue of the TM component that forms the second part of the disulphide bond is located within the last 20 C-terminal amino acid residues of the Targeting Moiety.

25. A single chain, polypeptide fusion protein, comprising:
a) a non-cytotoxic protease that cleaves a protein of the exocytic fusion apparatus of a target cell;
b) a Targeting Moiety that binds to a Binding Site on the target cell, which Binding Site undergoes endocytosis to be incorporated into an endosome within the target cell;
c) a protease cleavage site at which site the fusion protein is cleavable by a protease, wherein the protease cleavage site is located between the non-cytotoxic protease and the Targeting Moiety;
d) a translocation domain that translocates the non-cytotoxic protease from within an endosome, across the endosomal membrane and into the cytosol of the target cell;
wherein the Targeting Moiety is located between the protease cleavage site and the translocation domain; and
wherein the non-cytotoxic protease and the translocation domain are distanced apart from one another by a maximum of 100 amino acid residues.

* * * * *

SEQUENCE LISTING

```
<160> NUMBER OF SEQ ID NOS: 64

<210> SEQ ID NO 1
<211> LENGTH: 1302
<212> TYPE: DNA
<213> ORGANISM: Artificial Sequence
<220> FEATURE:
<223> OTHER INFORMATION: Synthetic

<400> SEQUENCE: 1
ggatccatgg agttcgttaa caaacagttc aactataaag acccagttaa cggtgttgac      60
attgcttaca tcaaaatccc gaacgctggc cagatgcagc cggtaaaggc attcaaaatc     120
cacaacaaaa tctgggttat cccggaacgt gataccttta ctaacccgga agaaggtgac     180
ctgaacccgc caccggaagc gaaacaggtg ccggtatctt actatgactc cacctacctg     240
tctaccgata acgaaaagga caactacctg aaaggtgtta ctaaactgtt cgagcgtatt     300
tactccaccg acctgggccg tatgctgctg actagcatcg ttcgcggtat cccgttctgg     360
ggcggttcta ccatcgatac cgaactgaaa gtaatcgaca ctaactgcat caacgttatt     420
cagccggacg gttcctatcg ttccgaagaa ctgaacctgg tgatcatcgg cccgtctgct     480
gatatcatcc agttcgagtg taagagcttt ggtcacgaag ttctgaacct cacccgtaac     540
ggctacggtt ccactcagta catccgtttc tctccggact tcaccttcgg ttttgaagaa     600
tccctggaag tagacacgaa cccactgctg ggcgctggta aattcgcaac tgatcctgcg     660
```

```
gttaccctgg ctcacgaact gattcatgca ggccaccgcc tgtacggtat cgccatcaat    720
ccgaaccgtg tcttcaaagt taacaccaac gcgtattacg agatgtccgg tctggaagtt    780
agcttcgaag aactgcgtac ttttggcggt cacgacgcta aattcatcga ctctctgcaa    840
gaaaacgagt tccgtctgta ctactataac aagttcaaag atatcgcatc caccctgaac    900
aaagcgaaat ccatcgtggg taccactgct ctctccagt acatgaagaa cgttttaaa    960 gaaaatacc tgctcagcga agacacctcc ggcaaattct ctgtagacaa gttgaaattc   1020
gataaacttt acaaaatgct gactgaaatt taccccgaag acaacttcgt taagttcttt   1080
aaagttctga accgcaaaac ctatctgaac ttcgacaagg cagtattcaa atcaacatc   1140 gtgccgaaag ttaactacac tatctacgat ggtttcaacc tgcgtaacac caacctggct   1200
gctaatttta acggcagaa cacggaaatc aacaacatga acttcacaaa actgaaaaac   1260
ttcactggtc tgttcgagtt ttacaagctg ctgtgcgtcg ac                     1302
```

<210> SEQ ID NO 2
<211> LENGTH: 1257
<212> TYPE: DNA
<213> ORGANISM: Artificial Sequence
<220> FEATURE:
<223> OTHER INFORMATION: Synthetic

<400> SEQUENCE: 2

```
ctgcagtgta tcaaggttaa caactgggat ttattcttca gcccgagtga agacaacttc     60
accaacgacc tgaacaaagg tgaagaaatc acctcagata ctaacatcga agcagccgaa    120
gaaaacatct cgctggacct gatccagcag tactacctga cctttaattt cgacaacgag    180
ccggaaaaca tttctatcga aaacctgagc tctgatatca tcggccagct ggaactgatg    240
ccgaacatcg aacgtttccc aaacggtaaa agtacgagc tggacaaata ccatgttc     300 cactacctgc gcgcgcagga atttgaacac ggcaaatccc gtatcgcact gactaactcc    360
gttaacgaag ctctgctcaa cccgtcccgt gtatacacct tcttctctag cgactacgtg    420
aaaaaggtca acaaagcgac tgaagctgca atgttcttgg gttgggttga acagcttgtt    480
tatgatttta ccgacgagac gtccgaagta tctactaccg acaaaattgc ggatatcact    540
atcatcatcc cgtacatcgg tccggctctg aacattggca acatgctgta caaagacgac    600
ttcgttggcg cactgatctt ctccggtgcg gtgatcctgc tggagttcat cccggaaatc    660
gccatcccgg tactgggcac ctttgctctg gtttcttaca ttgcaaacaa ggttctgact    720
gtacaaacca tcgacaacgc gctgagcaaa cgtaacgaaa atgggatga agtttacaaa    780 tatatcgtga ccaactggct ggctaaggtt aatactcaga tcgacctcat ccgcaaaaaa    840
atgaaagaag cactggaaaa ccaggcgaaa gctaccaagg caatcattaa ctaccagtac    900
aaccagtaca ccgaggaaga aaaaaacaac atcaacttca acatcgacga tctgtcctct    960
aaactgaacg aatccatcaa caaagctatg atcaacatca caagttcct gaaccagtgc   1020 tctgtaagct atctgatgaa ctccatgatc ccgtacggtg ttaaacgtct ggaggacttc   1080
gatgcgtctc tgaaagacgc cctgctgaaa tacattacg acaaccgtgg cactctgatc   1140
ggtcaggttg atcgtctgaa ggacaaagtg aacaatacct atcgaccga catcccttt   1200 cagctcagta aatatgtcga taaccaacgc ctttttgtcca ctctagacta gaagctt     1257
```

<210> SEQ ID NO 3
<211> LENGTH: 1323
<212> TYPE: DNA

<213> ORGANISM: Artificial Sequence
<220> FEATURE:
<223> OTHER INFORMATION: Synthetic

<400> SEQUENCE: 3

```
ggatccatgc cggttaccat caacaacttc aactacaacg acccgatcga caacaacaac      60
atcattatga tggaaccgcc gttcgcacgt ggtaccggac gttactacaa ggcttttaag     120
atcaccgacc gtatctggat catcccggaa cgttacacct cggttacaa  acctgaggac     180
ttcaacaaga gtagcgggat tttcaatcgt gacgtctgcg agtactatga tccagattat     240
ctgaatacca acgataagaa gaacatattc cttcagacta tgattaaact cttcaaccgt     300
atcaaaagca aaccgctcgg tgaaaaactc ctcgaaatga ttatcaacgg tatcccgtac     360
ctcggtgacc gtcgtgtccc gcttgaagag ttcaacacca catcgcaag  cgtcaccgtc     420
aacaaactca tcagcaaccc aggtgaagtc gaacgtaaaa aaggtatctt cgcaaacctc     480
atcatcttcg gtccgggtcc ggtcctcaac gaaaacgaaa ccatcgacat cggtatccag     540
aaccacttcg caagccgtga aggtttcggt ggtatcatgc agatgaaatt ctgcccggaa     600
tacgtcagtg tcttcaacaa cgtccaggaa aacaaaggtg caagcatctt caaccgtcgt     660
ggttacttca gcgacccggc actcatcctc atgcatgaac tcatccacgt cctccacggt     720
ctctacggta tcaaagttga cgacctcccg atcgtcccga acgagaagaa attcttcatg     780
cagagcaccg acgcaatcca ggctgaggaa ctctacacct cggtggcca  agacccaagt     840
atcataaccc cgtccaccga caaaagcatc tacgacaaag tcctccagaa cttcaggggt     900
atcgtggaca gactcaacaa agtcctcgtc tgcatcagcg acccgaacat caatatcaac     960
atatacaaga acaagttcaa agacaagtac aaattcgtcg aggacagcga aggcaaatac    1020
agcatcgacg tagaaagttt cgacaagctc tacaaaagcc tcatgttcgg tttcaccgaa    1080
accaacatcg ccgagaacta caagatcaag acaagggcaa gttacttcag cgacagcctc    1140
ccgcctgtca aaatcaagaa cctcttagac aacgagattt acacaattga gagggcttc    1200
aacatcagtg acaaagacat ggagaaggaa tacagaggtc agaacaaggc tatcaacaaa    1260
caggcatacg aggagatcag caaagaacac ctcgcagtct acaagatcca gatgtgcgtc    1320
gac                                                                   1323
```

<210> SEQ ID NO 4
<211> LENGTH: 1260
<212> TYPE: DNA
<213> ORGANISM: Artificial Sequence
<220> FEATURE:
<223> OTHER INFORMATION: Synthetic

<400> SEQUENCE: 4

```
ctgcagtgca tcgacgttga caacgaagac ctgttcttca tcgctgacaa aaacagcttc      60
agtgacgacc tgagcaaaaa cgaacgtatc gaatacaaca cccagagcaa ctacatcgaa     120
aacgacttcc cgatcaacga actgatcctg gacaccgacc tgataagtaa aatcgaactg     180
ccgagcgaaa acaccgaaag tctgaccgac ttcaacgttg acgttccggt ttacgaaaaa     240
cagccggcta tcaagaaaat cttcaccgac gaaaacacca tcttccagta cctgtacagc     300
cagaccttcc cgctggacat ccgtgacatc agtctgacca gcagtttcga cgacgctctg     360
ctgttcagca acaaagttta cagtttcttc agcatggact acatcaaaac cgctaacaaa     420
gttgttgaag cagggctgtt cgctggttgg gttaaacaga tcgttaacga cttcgttatc     480
gaagctaaca aaagcaacac tatggacaaa atcgctgaca tcagtctgat cgttccgtac     540
```

```
atcggtctgg ctctgaacgt tggtaacgaa accgctaaag gtaactttga aaacgctttc      600
gagatcgctg gtgcaagcat cctgctggag ttcatcccgg aactgctgat cccggttgtt      660
ggtgctttcc tgctggaaag ttacatcgac aacaaaaaca agatcatcaa aaccatcgac      720
aacgctctga ccaaacgtaa cgaaaaatgg agtgatatgt acggtctgat cgttgctcag      780
tggctgagca ccgtcaacac ccagttctac accatcaaag aaggtatgta caaagctctg      840
aactaccagg ctcaggctct ggaagagatc atcaaatacc gttacaacat ctacagtgag      900
aaggaaaaga gtaacatcaa catcgacttc aacgacatca acagcaaact gaacgaaggt      960
atcaaccagg ctatcgacaa catcaacaac ttcatcaacg gttgcagtgt tagctacctg     1020
atgaagaaga tgatcccgct ggctgttgaa aaactgctgg acttcgacaa caccctgaaa     1080
aagaacctgc tgaactacat cgacgaaaac aagctgtacc tgatcggtag tgctgaatac     1140
gaaaaaagta agtgaacaa atacctgaag accatcatgc cgttcgacct gagtatctac     1200
accaacgaca ccatcctgat cgaaatgttc aacaaataca actctctaga ctagaagctt     1260
```

<210> SEQ ID NO 5
<211> LENGTH: 1329
<212> TYPE: DNA
<213> ORGANISM: Artificial Sequence
<220> FEATURE:
<223> OTHER INFORMATION: Synthetic

<400> SEQUENCE: 5

```
ggatccgaat tcatgccgat caccatcaac aacttcaact acagcgatcc ggtggataac       60
aaaaacatcc tgtacctgga tacccatctg aatacccctgg cgaacgaacc ggaaaaagcg      120
tttcgtatca ccggcaacat ttgggttatt ccggatcgtt ttagccgtaa cagcaacccg      180
aatctgaata aaccgccgcg tgttaccagc ccgaaaagcg gttattacga tccgaactat      240
ctgagcaccg atagcgataa agatacccttc ctgaaagaaa tcatcaaact gttcaaacgc      300
atcaacagcc gtgaaattgg cgaagaactg atctatcgcc tgagcaccga tattccgttt      360
ccgggcaaca caacacccc gatcaacacc tttgatttcg atgtggattt caacagcgtt      420
gatgttaaaa cccgccaggg taacaattgg gtgaaaaccg gcagcattaa cccgagcgtg      480
attattaccg gtccgcgcga aaacattatt gatccggaaa ccagcacctt taaactgacc      540 aacaacaccct ttgcggcgca ggaaggtttt ggcgcgctga gcattattag cattagcccg      600
cgctttatgc tgacctatag caacgcgacc aacgatgttg gtgaaggccg tttcagcaaa      660
agcgaatttt gcatggaccc gatcctgatc ctgatgcatg aactgaacca tgcgatgcat      720
aacctgtatg gcatcgcgat tccgaacgat cagaccatta gcagcgtgac cagcaacatc      780
ttttacagcc agtacaacgt gaaactgaa tatgcggaaa tctatgcgtt tggcggtccg      840
accattgatc tgattccgaa agcgcgcgc aaatacttcg aagaaaaagc gctggattac      900
tatcgcagca ttgcgaaacg tctgaacagc attaccaccg cgaatccgag cagcttcaac      960
aaatatatcg gcgaatataa acagaaactg atccgcaaat atcgctttgt ggtggaaagc     1020
agcggcgaag ttaccgttaa ccgcaataaa ttcgtggaac tgtacaacga actgacccag     1080
atcttcaccg aatttaacta tgcgaaaatc tataacgtgc agaaccgtaa aatctacctg     1140
agcaacgtgt atacccccggt gaccgcgaat attctggatg ataacgtgta cgatatccag     1200 aacggctta acatcccgaa aagcaacctg aacgttctgt ttatgggcca gaacctgagc     1260
cgtaatccgg cgctgcgtaa agtgaacccg gaaaacatgc tgtacctgtt caccaaattt     1320
```

```
tgcgtcgac                                                         1329
```

<210> SEQ ID NO 6
<211> LENGTH: 1263
<212> TYPE: DNA
<213> ORGANISM: Artificial Sequence
<220> FEATURE:
<223> OTHER INFORMATION: Synthetic

<400> SEQUENCE: 6

```
ctgcagtgtc gtgaactgct ggtgaaaaac accgatctgc cgtttattgg cgatatcagc    60
gatgtgaaaa ccgatatctt cctgcgcaaa gatatcaacg aagaaaccga agtgatctac   120
tacccggata acgtgagcgt tgatcaggtg atcctgagca aaaacaccag cgaacatggt   180
cagctggatc tgctgtatcc gagcattgat agcgaaagcg aaattctgcc gggcgaaaac   240
caggtgtttt acgataaccg tacccagaac gtggattacc tgaacagcta ttactacctg   300
gaaagccaga aactgagcga taacgtggaa gattttaccct ttacccgcag cattgaagaa   360
gcgctggata acagcgcgaa agtttacacc tattttccga ccctggcgaa caaagttaat   420
gcgggtgttc agggcggtct gtttctgatg tgggcgaacg atgtggtgga agatttcacc   480
accaacatcc tgcgtaaaga tacccctggat aaaatcagcg atgttagcgc gattattccg   540
tatattggtc cggcgctgaa cattagcaat agcgtgcgtc gtggcaattt taccgaagcg   600
tttgcggtta ccgtgtgac cattctgctg aagcgtttc cggaatttac cattccggcg   660
ctgggtgcgt ttgtgatcta tagcaaagtg caggaacgca acgaaatcat caaaaccatc   720
gataactgcc tggaacagcg tattaaacgc tggaaagata gctatgaatg gatgatgggc   780
acctggctga gccgtattat cacccagttc aacaacatca gctaccagat gtacgatagc   840
ctgaactatc aggcgggtgc gattaaagcg aaaatcgatc tggaatacaa aaaatacagc   900
ggcagcgata agaaaaacat caaaagccag gttgaaaacc tgaaaaacag cctggatgtg   960
aaaattagcg aagcgatgaa taacatcaac aaattcatcc gcgaatgcag cgtgacctac  1020
ctgttcaaaa acatgctgcc gaaagtgatc gatgaactga acgaatttga tcgcaacacc  1080
aaagcgaaac tgatcaacct gatcgatagc cacaacatta ttctggtggg cgaagtggat  1140
aaactgaaag cgaaagttaa caacagcttc cagaacacca tcccgtttaa catcttcagc  1200
tataccaaca cagcctgct gaaagatatc atcaacgaat acttcaatct agactagaag  1260
ctt                                                                1263
```

<210> SEQ ID NO 7
<211> LENGTH: 159
<212> TYPE: DNA
<213> ORGANISM: Artificial Sequence
<220> FEATURE:
<223> OTHER INFORMATION: Synthetic

<400> SEQUENCE: 7

```
ggatccacgc acgtcgacga agaaaagctg tacgacgacg acgacaaaac cttttttactg    60
cgtgcgctag cgggcggtgg cggtagcggc ggtggcggta gcggcggtgg cggtagcgca   120
ctagtgctgc agacgcacgg tctagaatga taaaagctt                          159
```

<210> SEQ ID NO 8
<211> LENGTH: 231
<212> TYPE: DNA
<213> ORGANISM: Artificial Sequence
<220> FEATURE:
<223> OTHER INFORMATION: Synthetic

<400> SEQUENCE: 8

```
ggatccacgc acgtcgacgc gattgatggt cgtagcgtct ctgagattca gctgatgcat    60
aatttaggca aacacttgaa tagtatggaa cgtgttgaat ggctgcgcaa aaaacttcaa   120
gatgtgcata actttgcgct agcgggcggt ggcggtagcg gcggtggcgg tagcggcggt   180
ggcggtagcg cactagtgct gcagacgcac ggtctagaat gataaaagct t            231
```

<210> SEQ ID NO 9
<211> LENGTH: 2685
<212> TYPE: DNA
<213> ORGANISM: Artificial Sequence
<220> FEATURE:
<223> OTHER INFORMATION: Synthetic

<400> SEQUENCE: 9

```
ggatccatgc cggttaccat caacaacttc aactacaacg acccgatcga caacaacaac    60
atcattatga tggaaccgcc gttcgcacgt ggtaccggac gttactacaa ggcttttaag   120
atcaccgacc gtatctggat catcccggaa cgttacacct tcggttacaa acctgaggac   180
ttcaacaaga gtagcgggat tttcaatcgt gacgtctgcg agtactatga tccagattat   240
ctgaatacca acgataagaa gaacatattc cttcagacta tgattaaact cttcaaccgt   300
atcaaaagca aacgctcgg tgaaaaactc ctcgaaatga ttatcaacgg tatcccgtac   360
ctcggtgacc gtcgtgtccc gcttgaagag ttcaacacca acatcgcaag cgtcaccgtc   420
aacaaactca tcagcaaccc aggtgaagtc gaacgtaaaa aaggtatctt cgcaaacctc   480
atcatcttcg gtccgggtcc ggtcctcaac gaaaacgaaa ccatcgacat cggtatccag   540
aaccacttcg caagccgtga aggtttcggt ggtatcatgc agatgaaatt ctgcccggaa   600
tacgtcagtg tcttcaacaa cgtccaggaa acaaaggtg caagcatctt caaccgtcgt   660
ggttacttca cgaccccggc actcatcctc atgcatgaac tcatccacgt cctccacggt   720
ctctacggta tcaaagttga cgacctcccg atcgtcccga acgagaagaa attcttcatg   780
cagagccaccg acgcaatcca ggctgaggaa ctctacacct tcggtggcca agacccaagt   840
atcataaccc cgtccaccga caaaagcatc tacgacaaag tcctccagaa cttcaggggt   900
atcgtggaca gactcaacaa agtcctcgtc tgcatcagcg acccgaacat caatatcaac   960
atatacaaga acaagttcaa agacaagtac aaattcgtcg aggacagcga aggcaaatac  1020
agcatcgacg tagaaagttt cgacaagctc tacaaaagcc tcatgttcgg tttcaccgaa  1080
accaacatcg ccgagaacta caagatcaag acaagggcaa gttacttcag cgacagcctc  1140
ccgcctgtca aaatcaagaa cctcttagac aacgagattt acacaattga gagggcttc  1200
aacatcagtg acaagacat ggagaaggaa tacagaggtc agaacaaggc tatcaacaaa  1260
caggcatacg aggagatcag caaagaacac ctcgcagtct acaagatcca gatgtgcgtc  1320
gacgaagaaa agctgtacga cgacgacgac aaaacctttt tactgcgtgc gctagcgggc  1380
ggtggcggta gcggcggtgg cggtagcggc ggtggcggta gcgcactagt gctgcagtgc  1440
atcgacgttg acaacgaaga cctgttcttc atcgctgaca aaaacagctt cagtgacgac  1500
ctgagcaaaa acgaacgtat cgaatacaac acccagagca actacatcga aaacgacttc  1560
ccgatcaacg aactgatcct ggacaccgac ctgataagta aaatcgaact gccgagcgaa  1620
aacaccgaaa gtctgaccga cttcaacgtt gacgttccgg tttacgaaaa acagccggct  1680
atcaagaaaa tcttcaccga cgaaaacacc atcttccagt acctgtacag ccagaccttc  1740
```

```
ccgctggaca tccgtgacat cagtctgacc agcagtttcg acgacgctct gctgttcagc    1800
aacaaagttt acagtttctt cagcatggac tacatcaaaa ccgctaacaa agttgttgaa    1860
gcagggctgt tcgctggttg ggttaaacag atcgttaacg acttcgttat cgaagctaac    1920
aaaagcaaca ctatggacaa aatcgctgac atcagtctga tcgttccgta catcggtctg    1980
gctctgaacg ttggtaacga aaccgctaaa ggtaactttg aaaacgcttt cgagatcgct    2040
ggtgcaagca tcctgctgga gttcatcccg gaactgctga tcccggttgt tggtgctttc    2100
ctgctggaaa gttacatcga acaaaaaac aagatcatca aaccatcga caacgctctg    2160 accaaacgta acgaaaaatg gagtgatatg tacggtctga tcgttgctca gtggctgagc    2220
accgtcaaca cccagttcta caccatcaaa gaaggtatgt acaaagctct gaactaccag    2280
gctcaggctc tggaagagat catcaaatac cgttacaaca tctacagtga aaggaaaag    2340 agtaacatca acatcgactt caacgacatc aacagcaaac tgaacgaagg tatcaaccag    2400
gctatcgaca catcaacaa cttcatcaac ggttgcagtg ttagctacct gatgaagaag    2460
atgatcccgc tggctgttga aaaactgctg gacttcgaca cacccctgaa aaagaacctg    2520
ctgaactaca tcgacgaaaa caagctgtac ctgatcggta gtgctgaata cgaaaaaagt    2580
aaagtgaaca ataccctgaa gaccatcatg ccgttcgacc tgagtatcta caccaacgac    2640
accatcctga tcgaaatgtt caacaaatac aactctctag actag              2685
```

<210> SEQ ID NO 10
<211> LENGTH: 894
<212> TYPE: PRT
<213> ORGANISM: Artificial Sequence
<220> FEATURE:
<223> OTHER INFORMATION: Synthetic

<400> SEQUENCE: 10

```
Gly Ser Met Pro Val Thr Ile Asn Asn Phe Asn Tyr Asn Asp Pro Ile
1               5                   10                  15

Asp Asn Asn Asn Ile Ile Met Met Glu Pro Pro Phe Ala Arg Gly Thr
            20                  25                  30

Gly Arg Tyr Tyr Lys Ala Phe Lys Ile Thr Asp Arg Ile Trp Ile Ile
        35                  40                  45

Pro Glu Arg Tyr Thr Phe Gly Tyr Lys Pro Glu Asp Phe Asn Lys Ser
    50                  55                  60

Ser Gly Ile Phe Asn Arg Asp Val Cys Glu Tyr Tyr Asp Pro Asp Tyr
65                  70                  75                  80

Leu Asn Thr Asn Asp Lys Lys Asn Ile Phe Leu Gln Thr Met Ile Lys
                85                  90                  95

Leu Phe Asn Arg Ile Lys Ser Lys Pro Leu Gly Glu Lys Leu Leu Glu
            100                 105                 110

Met Ile Ile Asn Gly Ile Pro Tyr Leu Gly Asp Arg Arg Val Pro Leu
        115                 120                 125

Glu Glu Phe Asn Thr Asn Ile Ala Ser Val Thr Val Asn Lys Leu Ile
    130                 135                 140

Ser Asn Pro Gly Glu Val Glu Arg Lys Lys Gly Ile Phe Ala Asn Leu
145                 150                 155                 160

Ile Ile Phe Gly Pro Gly Pro Val Leu Asn Glu Asn Glu Thr Ile Asp
                165                 170                 175

Ile Gly Ile Gln Asn His Phe Ala Ser Arg Glu Gly Phe Gly Gly Ile
            180                 185                 190

Met Gln Met Lys Phe Cys Pro Glu Tyr Val Ser Val Phe Asn Asn Val
```

-continued

```
                195                 200                 205
Gln Glu Asn Lys Gly Ala Ser Ile Phe Asn Arg Arg Gly Tyr Phe Ser
210                 215                 220

Asp Pro Ala Leu Ile Leu Met His Glu Leu Ile His Val Leu His Gly
225                 230                 235                 240

Leu Tyr Gly Ile Lys Val Asp Asp Leu Pro Ile Val Pro Asn Glu Lys
                245                 250                 255

Lys Phe Phe Met Gln Ser Thr Asp Ala Ile Gln Ala Glu Glu Leu Tyr
                260                 265                 270

Thr Phe Gly Gly Gln Asp Pro Ser Ile Ile Thr Pro Ser Thr Asp Lys
            275                 280                 285

Ser Ile Tyr Asp Lys Val Leu Gln Asn Phe Arg Gly Ile Val Asp Arg
290                 295                 300

Leu Asn Lys Val Leu Val Cys Ile Ser Asp Pro Asn Ile Asn Ile Asn
305                 310                 315                 320

Ile Tyr Lys Asn Lys Phe Lys Asp Lys Tyr Lys Phe Val Glu Asp Ser
                325                 330                 335

Glu Gly Lys Tyr Ser Ile Asp Val Glu Ser Phe Asp Lys Leu Tyr Lys
                340                 345                 350

Ser Leu Met Phe Gly Phe Thr Glu Thr Asn Ile Ala Glu Asn Tyr Lys
            355                 360                 365

Ile Lys Thr Arg Ala Ser Tyr Phe Ser Asp Ser Leu Pro Pro Val Lys
370                 375                 380

Ile Lys Asn Leu Leu Asp Asn Glu Ile Tyr Thr Ile Glu Glu Gly Phe
385                 390                 395                 400

Asn Ile Ser Asp Lys Asp Met Glu Lys Glu Tyr Arg Gly Gln Asn Lys
                405                 410                 415

Ala Ile Asn Lys Gln Ala Tyr Glu Glu Ile Ser Lys Glu His Leu Ala
                420                 425                 430

Val Tyr Lys Ile Gln Met Cys Val Asp Glu Glu Lys Leu Tyr Asp Asp
            435                 440                 445

Asp Asp Lys Thr Phe Leu Leu Arg Ala Leu Ala Gly Gly Gly Gly Ser
450                 455                 460

Gly Gly Gly Gly Ser Gly Gly Gly Ser Ala Leu Val Leu Gln Cys
465                 470                 475                 480

Ile Asp Val Asp Asn Glu Asp Leu Phe Phe Ile Ala Asp Lys Asn Ser
                485                 490                 495

Phe Ser Asp Asp Leu Ser Lys Asn Glu Arg Ile Glu Tyr Asn Thr Gln
                500                 505                 510

Ser Asn Tyr Ile Glu Asn Asp Phe Pro Ile Asn Glu Leu Ile Leu Asp
            515                 520                 525

Thr Asp Leu Ile Ser Lys Ile Glu Leu Pro Ser Glu Asn Thr Glu Ser
530                 535                 540

Leu Thr Asp Phe Asn Val Asp Val Pro Val Tyr Glu Lys Gln Pro Ala
545                 550                 555                 560

Ile Lys Lys Ile Phe Thr Asp Glu Asn Thr Ile Phe Gln Tyr Leu Tyr
                565                 570                 575

Ser Gln Thr Phe Pro Leu Asp Ile Arg Asp Ile Ser Leu Thr Ser Ser
            580                 585                 590

Phe Asp Asp Ala Leu Leu Phe Ser Asn Lys Val Tyr Ser Phe Phe Ser
            595                 600                 605

Met Asp Tyr Ile Lys Thr Ala Asn Lys Val Val Glu Ala Gly Leu Phe
            610                 615                 620
```

```
Ala Gly Trp Val Lys Gln Ile Val Asn Asp Phe Val Ile Glu Ala Asn
625                 630                 635                 640

Lys Ser Asn Thr Met Asp Lys Ile Ala Asp Ile Ser Leu Ile Val Pro
            645                 650                 655

Tyr Ile Gly Leu Ala Leu Asn Val Gly Asn Glu Thr Ala Lys Gly Asn
        660                 665                 670

Phe Glu Asn Ala Phe Glu Ile Ala Gly Ala Ser Ile Leu Leu Glu Phe
    675                 680                 685

Ile Pro Glu Leu Leu Ile Pro Val Val Gly Ala Phe Leu Leu Glu Ser
690                 695                 700

Tyr Ile Asp Asn Lys Asn Lys Ile Ile Lys Thr Ile Asp Asn Ala Leu
705                 710                 715                 720

Thr Lys Arg Asn Glu Lys Trp Ser Asp Met Tyr Gly Leu Ile Val Ala
            725                 730                 735

Gln Trp Leu Ser Thr Val Asn Thr Gln Phe Tyr Thr Ile Lys Glu Gly
        740                 745                 750

Met Tyr Lys Ala Leu Asn Tyr Gln Ala Gln Ala Leu Glu Glu Ile Ile
    755                 760                 765

Lys Tyr Arg Tyr Asn Ile Tyr Ser Glu Lys Lys Ser Asn Ile Asn
770                 775                 780

Ile Asp Phe Asn Asp Ile Asn Ser Lys Leu Asn Glu Gly Ile Asn Gln
785                 790                 795                 800

Ala Ile Asp Asn Ile Asn Asn Phe Ile Asn Gly Cys Ser Val Ser Tyr
            805                 810                 815

Leu Met Lys Lys Met Ile Pro Leu Ala Val Glu Lys Leu Leu Asp Phe
        820                 825                 830

Asp Asn Thr Leu Lys Lys Asn Leu Leu Asn Tyr Ile Asp Glu Asn Lys
    835                 840                 845

Leu Tyr Leu Ile Gly Ser Ala Glu Tyr Glu Lys Ser Lys Val Asn Lys
850                 855                 860

Tyr Leu Lys Thr Ile Met Pro Phe Asp Leu Ser Ile Tyr Thr Asn Asp
865                 870                 875                 880

Thr Ile Leu Ile Glu Met Phe Asn Lys Tyr Asn Ser Leu Asp
            885                 890
```

<210> SEQ ID NO 11
<211> LENGTH: 2766
<212> TYPE: DNA
<213> ORGANISM: Artificial Sequence
<220> FEATURE:
<223> OTHER INFORMATION: Synthetic

<400> SEQUENCE: 11

```
ggatccgaat tcatgccgat caccatcaac aacttcaact acagcgatcc ggtggataac    60
aaaaacatcc tgtacctgga tacccatctg aatccctggc gaacgaacc ggaaaaagcg   120 tttcgtatca ccggcaacat ttgggttatt ccgatcgtt ttagccgtaa cagcaacccg   180
aatctgaata accgccgcg tgttaccagc ccgaaaagcg gttattacga tccgaactat   240
ctgagcaccg atagcgataa agatacctt ctgaaagaaa tcatcaaact gttcaaacgc   300
atcaacagcc gtgaaattgg cgaagaactg atctatcgcc tgagcaccga tattccgttt   360
ccgggcaaca caacacccc gatcaacacc tttgatttcg atgtggattt caacagcgtt   420
gatgttaaaa cccgccaggg taacaattgg gtgaaaccg gcagcattaa cccgagcgtg   480
attattaccg gtccgcgcga aaacattatt gatccggaaa ccagcaccctt taaactgacc   540
```

```
aacaacacct tgcggcgca ggaaggtttt ggcgcgctga gcattattag cattagcccg      600
cgctttatgc tgacctatag caacgcgacc aacgatgttg gtgaaggccg tttcagcaaa      660
agcgaatttt gcatggaccc gatcctgatc ctgatgcatg aactgaacca tgcgatgcat      720
aacctgtatg gcatcgcgat tccgaacgat cagaccatta gcagcgtgac cagcaacatc      780
ttttacagcc agtacaacgt gaaactggaa tatgcggaaa tctatgcgtt tggcggtccg      840
accattgatc tgattccgaa agcgcgcgc  aaatacttcg aagaaaaagc gctggattac      900
tatcgcagca ttgcgaaacg tctgaacagc attaccaccg cgaatccgag cagcttcaac      960
aaatatatcg gcgaatataa acagaaactg atccgcaaat atcgctttgt ggtggaaagc     1020
agcggcgaag ttaccgttaa ccgcaataaa ttcgtggaac tgtacaacga actgacccag     1080
atcttcaccg aatttaacta tgcgaaaatc tataacgtgc agaaccgtaa aatctacctg     1140
agcaacgtgt ataccccggt gaccgcgaat attctggatg ataacgtgta cgatatccag     1200
aacggcttta acatcccgaa aagcaacctg aacgttctgt ttatgggcca gaacctgagc     1260
cgtaatccgg cgctgcgtaa agtgaacccg gaaaacatgc tgtacctgtt caccaaattt     1320
tgcgtcgacg cgattgatgg tcgtagcgtc tctgagattc agctgatgca taatttaggc     1380
aaacacttga atagtatgga acgtgttgaa tggctgcgca aaaaacttca agatgtgcat     1440
aactttgcgc tagcgggcgg tggcggtagc ggcggtggcg gtagcggcgg tggcggtagc     1500
gcactagtgc tgcagtgtcg tgaactgctg gtgaaaaaca ccgatctgcc gtttattggc     1560
gatatcagcg atgtgaaaac cgatatcttc ctgcgcaaag atatcaacga agaaaccgaa     1620
gtgatctact acccggataa cgtgagcgtt gatcaggtga tcctgagcaa aaacaccagc     1680
gaacatggtc agctggatct gctgtatccg agcattgata gcgaaagcga aattctgccg     1740
ggcgaaaacc aggtgttta  cgataaccgt acccagaacg tggattacct gaacagctat     1800
tactacctgg aaagccagaa actgagcgat aacgtggaag atttaccttt acccgcagc     1860 attgaagaag cgctggataa cagcgcgaaa gtttacacct attttccgac cctggcgaac     1920
aaagttaatg cgggtgttca gggcggtctg tttctgatgt gggcgaacga tgtggtggaa     1980
gatttcacca ccaacatcct gcgtaaagat accctggata aaatcagcga tgttagcgcg     2040
attattccgt atattggtcc ggcgctgaac attagcaata gcgtgcgtcg tggcaatttt     2100
accgaagcgt ttgcggttac cggtgtgacc attctgctgg aagcgttttcc ggaatttacc     2160 attccggcgc tgggtgcgtt tgtgatctat agcaaagtgc aggaacgcaa cgaaatcatc     2220
aaaaccatcg ataactgcct ggaacagcgt attaaacgct ggaaagatag ctatgaatgg     2280
atgatgggca cctggctgag ccgtattatc acccagttca acaacatcag ctaccagatg     2340
tacgatagcc tgaactatca ggcgggtgcg attaaagcga aaatcgatct ggaatacaaa     2400
aaatacagcg gcagcgataa agaaaacatc aaaagccagg ttgaaaacct gaaaaacagc     2460
ctggatgtga aaattagcga agcgatgaat aacatcaaca attcatccg  cgaatgcagc     2520 gtgacctacc tgttcaaaaa catgctgccg aaagtgatcg atgaactgaa cgaatttgat     2580
cgcaacacca aagcgaaact gatcaacctg atcgatagcc acaacattat tctggtgggc     2640
gaagtggata aactgaaagc gaaagttaac aacagcttcc agaacaccat cccgtttaac     2700
atcttcagct ataccaacaa cagcctgctg aaagatatca tcaacgaata cttcaatcta     2760
gactaa                                                               2766
```

<210> SEQ ID NO 12

<211> LENGTH: 921
<212> TYPE: PRT
<213> ORGANISM: Artificial Sequence
<220> FEATURE:
<223> OTHER INFORMATION: Synthetic

<400> SEQUENCE: 12

```
Gly Ser Glu Phe Met Pro Ile Thr Ile Asn Asn Phe Asn Tyr Ser Asp
1               5                   10                  15

Pro Val Asp Asn Lys Asn Ile Leu Tyr Leu Asp Thr His Leu Asn Thr
            20                  25                  30

Leu Ala Asn Glu Pro Glu Lys Ala Phe Arg Ile Thr Gly Asn Ile Trp
        35                  40                  45

Val Ile Pro Asp Arg Phe Ser Arg Asn Ser Asn Pro Asn Leu Asn Lys
50                  55                  60

Pro Pro Arg Val Thr Ser Pro Lys Ser Gly Tyr Tyr Asp Pro Asn Tyr
65                  70                  75                  80

Leu Ser Thr Asp Ser Asp Lys Asp Thr Phe Leu Lys Glu Ile Ile Lys
                85                  90                  95

Leu Phe Lys Arg Ile Asn Ser Arg Glu Ile Gly Glu Glu Leu Ile Tyr
            100                 105                 110

Arg Leu Ser Thr Asp Ile Pro Phe Pro Gly Asn Asn Asn Thr Pro Ile
        115                 120                 125

Asn Thr Phe Asp Phe Asp Val Asp Phe Asn Ser Val Asp Val Lys Thr
    130                 135                 140

Arg Gln Gly Asn Asn Trp Val Lys Thr Gly Ser Ile Asn Pro Ser Val
145                 150                 155                 160

Ile Ile Thr Gly Pro Arg Glu Asn Ile Ile Asp Pro Glu Thr Ser Thr
                165                 170                 175

Phe Lys Leu Thr Asn Asn Thr Phe Ala Ala Gln Glu Gly Phe Gly Ala
            180                 185                 190

Leu Ser Ile Ile Ser Ile Ser Pro Arg Phe Met Leu Thr Tyr Ser Asn
        195                 200                 205

Ala Thr Asn Asp Val Gly Glu Gly Arg Phe Ser Lys Ser Glu Phe Cys
    210                 215                 220

Met Asp Pro Ile Leu Ile Leu Met His Glu Leu Asn His Ala Met His
225                 230                 235                 240

Asn Leu Tyr Gly Ile Ala Ile Pro Asn Asp Gln Thr Ile Ser Ser Val
                245                 250                 255

Thr Ser Asn Ile Phe Tyr Ser Gln Tyr Asn Val Lys Leu Glu Tyr Ala
            260                 265                 270

Glu Ile Tyr Ala Phe Gly Gly Pro Thr Ile Asp Leu Ile Pro Lys Ser
        275                 280                 285

Ala Arg Lys Tyr Phe Glu Glu Lys Ala Leu Asp Tyr Tyr Arg Ser Ile
    290                 295                 300

Ala Lys Arg Leu Asn Ser Ile Thr Thr Ala Asn Pro Ser Ser Phe Asn
305                 310                 315                 320

Lys Tyr Ile Gly Glu Tyr Lys Gln Lys Leu Ile Arg Lys Tyr Arg Phe
                325                 330                 335

Val Val Glu Ser Ser Gly Glu Val Thr Val Asn Arg Asn Lys Phe Val
            340                 345                 350

Glu Leu Tyr Asn Glu Leu Thr Gln Ile Phe Thr Glu Phe Asn Tyr Ala
        355                 360                 365

Lys Ile Tyr Asn Val Gln Asn Arg Lys Ile Tyr Leu Ser Asn Val Tyr
    370                 375                 380
```

```
Thr Pro Val Thr Ala Asn Ile Leu Asp Asp Asn Val Tyr Asp Ile Gln
385                 390                 395                 400

Asn Gly Phe Asn Ile Pro Lys Ser Asn Leu Asn Val Leu Phe Met Gly
            405                 410                 415

Gln Asn Leu Ser Arg Asn Pro Ala Leu Arg Lys Val Asn Pro Glu Asn
        420                 425                 430

Met Leu Tyr Leu Phe Thr Lys Phe Cys Val Asp Ala Ile Asp Gly Arg
    435                 440                 445

Ser Val Ser Glu Ile Gln Leu Met His Asn Leu Gly Lys His Leu Asn
450                 455                 460

Ser Met Glu Arg Val Glu Trp Leu Arg Lys Lys Leu Gln Asp Val His
465                 470                 475                 480

Asn Phe Ala Leu Ala Gly Gly Gly Ser Gly Gly Gly Ser Gly
                485                 490                 495

Gly Gly Gly Ser Ala Leu Val Leu Gln Cys Arg Glu Leu Leu Val Lys
            500                 505                 510

Asn Thr Asp Leu Pro Phe Ile Gly Asp Ile Ser Asp Val Lys Thr Asp
            515                 520                 525

Ile Phe Leu Arg Lys Asp Ile Asn Glu Glu Thr Glu Val Ile Tyr Tyr
530                 535                 540

Pro Asp Asn Val Ser Val Asp Gln Val Ile Leu Ser Lys Asn Thr Ser
545                 550                 555                 560

Glu His Gly Gln Leu Asp Leu Leu Tyr Pro Ser Ile Asp Ser Glu Ser
            565                 570                 575

Glu Ile Leu Pro Gly Glu Asn Gln Val Phe Tyr Asp Asn Arg Thr Gln
            580                 585                 590

Asn Val Asp Tyr Leu Asn Ser Tyr Tyr Tyr Leu Glu Ser Gln Lys Leu
            595                 600                 605

Ser Asp Asn Val Glu Asp Phe Thr Phe Thr Arg Ser Ile Glu Glu Ala
610                 615                 620

Leu Asp Asn Ser Ala Lys Val Tyr Thr Tyr Phe Pro Thr Leu Ala Asn
625                 630                 635                 640

Lys Val Asn Ala Gly Val Gln Gly Gly Leu Phe Leu Met Trp Ala Asn
                645                 650                 655

Asp Val Val Glu Asp Phe Thr Thr Asn Ile Leu Arg Lys Asp Thr Leu
            660                 665                 670

Asp Lys Ile Ser Asp Val Ser Ala Ile Ile Pro Tyr Ile Gly Pro Ala
        675                 680                 685

Leu Asn Ile Ser Asn Ser Val Arg Arg Gly Asn Phe Thr Glu Ala Phe
    690                 695                 700

Ala Val Thr Gly Val Thr Ile Leu Leu Glu Ala Phe Pro Glu Phe Thr
705                 710                 715                 720

Ile Pro Ala Leu Gly Ala Phe Val Ile Tyr Ser Lys Val Gln Glu Arg
            725                 730                 735

Asn Glu Ile Ile Lys Thr Ile Asp Asn Cys Leu Glu Gln Arg Ile Lys
            740                 745                 750

Arg Trp Lys Asp Ser Tyr Glu Trp Met Met Gly Thr Trp Leu Ser Arg
        755                 760                 765

Ile Ile Thr Gln Phe Asn Asn Ile Ser Tyr Gln Met Tyr Asp Ser Leu
    770                 775                 780

Asn Tyr Gln Ala Gly Ala Ile Lys Ala Lys Ile Asp Leu Glu Tyr Lys
785                 790                 795                 800
```

-continued

| Lys | Tyr | Ser | Gly | Ser | Asp | Lys | Glu | Asn | Ile | Lys | Ser | Gln | Val | Glu | Asn |
|-----|-----|-----|-----|-----|-----|-----|-----|-----|-----|-----|-----|-----|-----|-----|-----|
|     |     |     |     | 805 |     |     |     |     | 810 |     |     |     |     | 815 |     |

Leu Lys Asn Ser Leu Asp Val Lys Ile Ser Glu Ala Met Asn Asn Ile
            820                 825                 830

Asn Lys Phe Ile Arg Glu Cys Ser Val Thr Tyr Leu Phe Lys Asn Met
        835                 840                 845

Leu Pro Lys Val Ile Asp Glu Leu Asn Glu Phe Asp Arg Asn Thr Lys
        850                 855                 860

Ala Lys Leu Ile Asn Leu Ile Asp Ser His Asn Ile Leu Val Gly
865             870             875                 880

Glu Val Asp Lys Leu Lys Ala Lys Val Asn Asn Ser Phe Gln Asn Thr
                885                 890                 895

Ile Pro Phe Asn Ile Phe Ser Tyr Thr Asn Asn Ser Leu Leu Lys Asp
            900                 905                 910

Ile Ile Asn Glu Tyr Phe Asn Leu Asp
            915             920

```
<210> SEQ ID NO 13
<211> LENGTH: 156
<212> TYPE: DNA
<213> ORGANISM: artificial sequence
<220> FEATURE:
<223> OTHER INFORMATION: DNA sequence of the CP RGD-C linker

<400> SEQUENCE: 13
ggatccacgc acgtcgacgc gattgatggt cgtggtggtc gtggtgacat gttcggtgct      60
gcgctagcgg gcggtggcgg tagcggcggt ggcggtagcg gcggtggcgg tagcgcacta     120
gtgctgcaga cgcacggtct agaatgataa aagctt                              156

<210> SEQ ID NO 14
<211> LENGTH: 2733
<212> TYPE: DNA
<213> ORGANISM: artificial sequence
<220> FEATURE:
<223> OTHER INFORMATION: DNA sequence of the CP RGD-C fusion

<400> SEQUENCE: 14
ggatccgaat tcatgccgat caccatcaac aacttcaact acagcgatcc ggtggataac      60
aaaaacatcc tgtacctgga tacccatctg aatccctggc gaacgaacc ggaaaaagcg     120 tttcgtatca ccggcaacat ttgggttatt ccggatcgtt ttagccgtaa cagcaacccg     180
aatctgaata aaccgccgcg tgttaccagc ccgaaaagcg gttattacga tccgaactat     240
ctgagcaccg atagcgataa agataccttc ctgaaagaaa tcatcaaact gttcaaacgc     300
atcaacagcc gtgaaattgg cgaagaactg atctatcgcc tgagcaccga tattccgttt     360
ccgggcaaca caacacccc gatcaacacc tttgatttcg atgtggattt caacagcgtt     420
gatgttaaaa cccgccaggg taacaattgg gtgaaaaccg gcagcattaa cccgagcgtg     480
attattaccg gtccgcgcga aaacattatt gatccggaaa ccagcacctt taaactgacc     540
aacaacacct tgcggcgca ggaaggtttt ggcgcgctga gcattattag cattagcccg     600
cgctttatgc tgacctatag caacgcgacc aacgatgttg tgaaggccg tttcagcaaa     660 agcgaatttt gcatggaccc gatcctgatc ctgatgcatg aactgaacca tgcgatgcat     720
aacctgtatg gcatcgcgat tccgaacgat cagaccatta gcagcgtgac cagcaacatc     780
ttttacagcc agtacaacgt gaaactggaa tatgcggaaa tctatgcgtt tggcggtccg     840
accattgatc tgattccgaa aagcgcgcgc aaatacttcg aagaaaaagc gctggattac     900
```

-continued

```
tatcgcagca ttgcgaaacg tctgaacagc attaccaccg cgaatccgag cagcttcaac    960
aaatatatcg gcgaatataa acagaaactg atccgcaaat atcgctttgt ggtggaaagc   1020
agcggcgaag ttaccgttaa ccgcaataaa ttcgtggaac tgtacaacga actgacccag   1080
atcttcaccg aatttaacta tgcgaaaatc tataacgtgc agaaccgtaa atctacctg    1140
agcaacgtgt ataccccggt gaccgcgaat attctggatg ataacgtgta cgatatccag   1200
aacggcttta catcccgaa aagcaacctg aacgttctgt tatgggcca gaacctgagc     1260
cgtaatccgg cgctgcgtaa agtgaacccg aaaacatgc tgtacctgtt caccaaattt    1320
tgcgtcgacg cgattgatgg tcgtggtggt cgtggtgaca tgttcggtgc tgcgctagcg   1380
ggcggtggcg gtagcggcgg tggcggtagc ggcggtggcg gtagcgcact agtgctgcag   1440
tgtcgtgaac tgctggtgaa aaacaccgat ctgccgttta ttggcgatat cagcgatgtg   1500
aaaaccgata tcttcctgcg caaagatatc aacgaagaaa ccgaagtgat ctactacccg   1560
gataacgtga cgttgatca ggtgatcctg agcaaaaaca ccagcgaaca tggtcagctg    1620
gatctgctgt atccgagcat tgatagcgaa agcgaaattc tgccgggcga aaaccaggtg   1680
ttttacgata accgtaccca gaacgtggat tacctgaaca gctattacta cctggaaagc   1740
cagaaactga gcgataacgt ggaagatttt acctttaccc gcagcattga agaagcgctg   1800
gataacagcg cgaaagttta cacctatttt ccgaccctgg cgaacaaagt taatgcgggt   1860
gttcagggcg gtctgtttct gatgtgggcg aacgatgtgg tggaagattt caccaccaac   1920
atcctgcgta aagataccct ggataaaatc agcgatgtta gcgcgattat tccgtatatt   1980
ggtccggcgc tgaacattag caatagcgtg cgtcgtggca ttttaccga gcgtttgcg     2040
gttaccggtg tgaccattct gctggaagcg tttccggaat ttaccattcc ggcgctgggt   2100
gcgtttgtga tctatagcaa agtgcaggaa cgcaacgaaa tcatcaaaac catcgataac   2160
tgcctggaac agcgtattaa acgctggaaa gatagctatg aatggatgat gggcaccctgg  2220
ctgagccgta ttatcaccca gttcaacaac atcagctacc agatgtacga tagcctgaac   2280
tatcaggcgg gtgcgattaa agcgaaaatc gatctggaat acaaaaaata cagcggcagc   2340
gataaagaaa acatcaaaag ccaggttgaa aacctgaaaa acagcctgga tgtgaaaatt   2400
agcgaagcga tgaataacat caacaaattc atccgcgaat gcagcgtgac ctacctgttc   2460
aaaaacatgc tgccgaaagt gatcgatgaa ctgaacgaat ttgatcgcaa caccaaagcg   2520
aaactgatca acctgatcga tagccacaac attattctgg tgggcgaagt ggataaactg   2580
aaagcgaaag ttaacaacag cttccagaac accatcccgt ttaacatctt cagctatacc   2640
aacaacagcc tgctgaaaga tatcatcaac gaatacttca atctagaagc actagcgagt   2700
gggcaccatc accatcacca ttaatgaaag ctt                                2733
```

<210> SEQ ID NO 15
<211> LENGTH: 909
<212> TYPE: PRT
<213> ORGANISM: artificial sequence
<220> FEATURE:
<223> OTHER INFORMATION: Protein sequence of the CP RGD-C fusion

<400> SEQUENCE: 15

```
Gly Ser Glu Phe Met Pro Ile Thr Ile Asn Asn Phe Asn Tyr Ser Asp
1               5                   10                  15

Pro Val Asp Asn Lys Asn Ile Leu Tyr Leu Asp Thr His Leu Asn Thr
            20                  25                  30
```

```
Leu Ala Asn Glu Pro Glu Lys Ala Phe Arg Ile Thr Gly Asn Ile Trp
             35                  40                  45

Val Ile Pro Asp Arg Phe Ser Arg Asn Ser Asn Pro Asn Leu Asn Lys
 50                  55                  60

Pro Pro Arg Val Thr Ser Pro Lys Ser Gly Tyr Tyr Asp Pro Asn Tyr
 65                  70                  75                  80

Leu Ser Thr Asp Ser Asp Lys Asp Thr Phe Leu Lys Glu Ile Ile Lys
                 85                  90                  95

Leu Phe Lys Arg Ile Asn Ser Arg Glu Ile Gly Glu Leu Ile Tyr
             100                 105                 110

Arg Leu Ser Thr Asp Ile Pro Phe Pro Gly Asn Asn Asn Thr Pro Ile
             115                 120                 125

Asn Thr Phe Asp Phe Asp Val Asp Phe Asn Ser Val Asp Val Lys Thr
             130                 135                 140

Arg Gln Gly Asn Asn Trp Val Lys Thr Gly Ser Ile Asn Pro Ser Val
145                 150                 155                 160

Ile Ile Thr Gly Pro Arg Glu Asn Ile Ile Asp Pro Glu Thr Ser Thr
                 165                 170                 175

Phe Lys Leu Thr Asn Asn Thr Phe Ala Ala Gln Glu Gly Phe Gly Ala
             180                 185                 190

Leu Ser Ile Ile Ser Ile Ser Pro Arg Phe Met Leu Thr Tyr Ser Asn
             195                 200                 205

Ala Thr Asn Asp Val Gly Glu Gly Arg Phe Ser Lys Ser Glu Phe Cys
             210                 215                 220

Met Asp Pro Ile Leu Ile Leu Met His Glu Leu Asn His Ala Met His
225                 230                 235                 240

Asn Leu Tyr Gly Ile Ala Ile Pro Asn Asp Gln Thr Ile Ser Ser Val
             245                 250                 255

Thr Ser Asn Ile Phe Tyr Ser Gln Tyr Asn Val Lys Leu Glu Tyr Ala
             260                 265                 270

Glu Ile Tyr Ala Phe Gly Gly Pro Thr Ile Asp Leu Ile Pro Lys Ser
             275                 280                 285

Ala Arg Lys Tyr Phe Glu Glu Lys Ala Leu Asp Tyr Tyr Arg Ser Ile
             290                 295                 300

Ala Lys Arg Leu Asn Ser Ile Thr Thr Ala Asn Pro Ser Ser Phe Asn
305                 310                 315                 320

Lys Tyr Ile Gly Glu Tyr Lys Gln Lys Leu Ile Arg Lys Tyr Arg Phe
             325                 330                 335

Val Val Glu Ser Ser Gly Glu Val Thr Val Asn Arg Asn Lys Phe Val
             340                 345                 350

Glu Leu Tyr Asn Glu Leu Thr Gln Ile Phe Thr Glu Phe Asn Tyr Ala
             355                 360                 365

Lys Ile Tyr Asn Val Gln Asn Arg Lys Ile Tyr Leu Ser Asn Val Tyr
             370                 375                 380

Thr Pro Val Thr Ala Asn Ile Leu Asp Asp Asn Val Tyr Asp Ile Gln
385                 390                 395                 400

Asn Gly Phe Asn Ile Pro Lys Ser Asn Leu Asn Val Leu Phe Met Gly
             405                 410                 415

Gln Asn Leu Ser Arg Asn Pro Ala Leu Arg Lys Val Asn Pro Glu Asn
             420                 425                 430

Met Leu Tyr Leu Phe Thr Lys Phe Cys Val Asp Ala Ile Asp Gly Arg
             435                 440                 445

Gly Gly Arg Gly Asp Met Phe Gly Ala Ala Leu Ala Gly Gly Gly Gly
```

-continued

```
            450             455             460
Ser Gly Gly Gly Ser Gly Gly Gly Ser Ala Leu Val Leu Gln
465                 470                 475             480

Cys Arg Glu Leu Leu Val Lys Asn Thr Asp Leu Pro Phe Ile Gly Asp
                485                 490                 495

Ile Ser Asp Val Lys Thr Asp Ile Phe Leu Arg Lys Asp Ile Asn Glu
            500                 505                 510

Glu Thr Glu Val Ile Tyr Tyr Pro Asp Asn Val Ser Val Asp Gln Val
        515                 520                 525

Ile Leu Ser Lys Asn Thr Ser Glu His Gly Gln Leu Asp Leu Leu Tyr
        530                 535                 540

Pro Ser Ile Asp Ser Glu Ser Glu Ile Leu Pro Gly Glu Asn Gln Val
545                 550                 555                 560

Phe Tyr Asp Asn Arg Thr Gln Asn Val Asp Tyr Leu Asn Ser Tyr Tyr
                565                 570                 575

Tyr Leu Glu Ser Gln Lys Leu Ser Asp Asn Val Glu Asp Phe Thr Phe
            580                 585                 590

Thr Arg Ser Ile Glu Glu Ala Leu Asp Asn Ser Ala Lys Val Tyr Thr
        595                 600                 605

Tyr Phe Pro Thr Leu Ala Asn Lys Val Asn Ala Gly Val Gln Gly Gly
        610                 615                 620

Leu Phe Leu Met Trp Ala Asn Asp Val Val Glu Asp Phe Thr Thr Asn
625                 630                 635                 640

Ile Leu Arg Lys Asp Thr Leu Asp Lys Ile Ser Asp Val Ser Ala Ile
                645                 650                 655

Ile Pro Tyr Ile Gly Pro Ala Leu Asn Ile Ser Asn Ser Val Arg Arg
            660                 665                 670

Gly Asn Phe Thr Glu Ala Phe Ala Val Thr Gly Val Thr Ile Leu Leu
        675                 680                 685

Glu Ala Phe Pro Glu Phe Thr Ile Pro Ala Leu Gly Ala Phe Val Ile
        690                 695                 700

Tyr Ser Lys Val Gln Glu Arg Asn Glu Ile Ile Lys Thr Ile Asp Asn
705                 710                 715                 720

Cys Leu Glu Gln Arg Ile Lys Arg Trp Lys Asp Ser Tyr Glu Trp Met
                725                 730                 735

Met Gly Thr Trp Leu Ser Arg Ile Ile Thr Gln Phe Asn Asn Ile Ser
            740                 745                 750

Tyr Gln Met Tyr Asp Ser Leu Asn Tyr Gln Ala Gly Ala Ile Lys Ala
        755                 760                 765

Lys Ile Asp Leu Glu Tyr Lys Lys Tyr Ser Gly Ser Asp Lys Glu Asn
        770                 775                 780

Ile Lys Ser Gln Val Glu Asn Leu Lys Asn Ser Leu Asp Val Lys Ile
785                 790                 795                 800

Ser Glu Ala Met Asn Asn Ile Asn Lys Phe Ile Arg Glu Cys Ser Val
                805                 810                 815

Thr Tyr Leu Phe Lys Asn Met Leu Pro Lys Val Ile Asp Glu Leu Asn
            820                 825                 830

Glu Phe Asp Arg Asn Thr Lys Ala Lys Leu Ile Asn Leu Ile Asp Ser
        835                 840                 845

His Asn Ile Ile Leu Val Gly Glu Val Asp Lys Leu Lys Ala Lys Val
        850                 855                 860

Asn Asn Ser Phe Gln Asn Thr Ile Pro Phe Asn Ile Phe Ser Tyr Thr
865                 870                 875                 880
```

```
Asn Asn Ser Leu Leu Lys Asp Ile Ile Asn Glu Tyr Phe Asn Leu Glu
                885                 890                 895

Ala Leu Ala Ser Gly His His His His His Lys Leu
        900                 905
```

```
<210> SEQ ID NO 16
<211> LENGTH: 162
<212> TYPE: DNA
<213> ORGANISM: artificial sequence
<220> FEATURE:
<223> OTHER INFORMATION: DNA sequence of CP cyclicRGD-C linker

<400> SEQUENCE: 16
```

| | | | | | |
|---|---|---|---|---|---|
| ggatccacgc | acgtcgacgc | gattgatggt | cgtggtggtt | gccgtggtga | catgttcggt | 60
| tgcgctgcgc | tagcgggcgg | tggcggtagc | ggcggtggcg | gtagcggcgg | tggcggtagc | 120
| gcactagtgc | tgcagacgca | cggtctagaa | tgataaaagc | tt | | 162

```
<210> SEQ ID NO 17
<211> LENGTH: 2739
<212> TYPE: DNA
<213> ORGANISM: artificial sequence
<220> FEATURE:
<223> OTHER INFORMATION: DNA sequence of the CP cyclicRGD-C fusion

<400> SEQUENCE: 17
```

| | | | | | |
|---|---|---|---|---|---|
| ggatccgaat | tcatgccgat | caccatcaac | aacttcaact | acagcgatcc | ggtggataac | 60
| aaaaacatcc | tgtacctgga | tacccatctg | aatccctgg | cgaacgaacc | ggaaaaagcg | 120
| tttcgtatca | ccggcaacat | tgggttatt | ccggatcgtt | tagccgtaa | cagcaacccg | 180
| aatctgaata | accgccgcg | tgttaccagc | ccgaaaagcg | gttattacga | tccgaactat | 240
| ctgagcaccg | atagcgataa | agataccttc | ctgaaagaaa | tcatcaaact | gttcaaacgc | 300
| atcaacagcc | gtgaaattgg | cgaagaactg | atctatcgcc | tgagcaccga | tattccgttt | 360
| ccgggcaaca | caacaccccc | gatcaacacc | tttgatttcg | atgtggattt | caacagcgtt | 420
| gatgttaaaa | cccgccaggg | taacaattgg | gtgaaaaccg | gcagcattaa | cccgagcgtg | 480
| attattaccg | gtccgcgcga | aaacattatt | gatccggaaa | ccagcacctt | taaactgacc | 540
| aacaacacct | tgcggcgca | ggaaggtttt | ggcgcgctga | cattattag | cattagcccg | 600
| cgctttatgc | tgacctatag | caacgcgacc | aacgatgttg | tgaaggccg | tttcagcaaa | 660
| agcgaatttt | gcatggaccc | gatcctgatc | ctgatgcatg | aactgaacca | tgcgatgcat | 720
| aacctgtatg | gcatcgcgat | tccgaacgat | cagaccatta | gcagcgtgac | cagcaacatc | 780
| ttttacagcc | agtacaacgt | gaaactggaa | tatgcggaaa | tctatgcgtt | ggcggtccg | 840
| accattgatc | tgattccgaa | aagcgcgcgc | aaatacttcg | aagaaaaagc | gctggattac | 900
| tatcgcagca | ttgcgaaacg | tctgaacagc | attaccaccg | cgaatccgag | cagcttcaac | 960
| aaatatatcg | cgaatataa | acagaaactg | atccgcaaat | atcgctttgt | ggtggaaagc | 1020
| agcggcgaag | ttaccgttaa | ccgcaataaa | ttcgtggaac | tgtacaacga | actgacccag | 1080
| atcttcaccg | aatttaacta | tgcgaaaatc | tataacgtgc | agaaccgtaa | aatctacctg | 1140
| agcaacgtgt | atacccccggt | gaccgcgaat | attctggatg | ataacgtgta | cgatatccag | 1200
| aacggcttta | acatcccgaa | aagcaacctg | aacgttctgt | ttatgggcca | gaacctgagc | 1260
| cgtaatccgg | cgctgcgtaa | agtgaacccg | gaaaacatgc | tgtacctgtt | caccaaattt | 1320
| tgcgtcgacg | cgattgatgg | tcgtggtggt | tgccgtggtg | acatgttcgg | ttgcgctgcg | 1380

```
ctagcgggcg gtggcggtag cggcggtggc ggtagcggcg gtggcggtag cgcactagtg  1440
ctgcagtgtc gtgaactgct ggtgaaaaac accgatctgc cgtttattgg cgatatcagc  1500
gatgtgaaaa ccgatatctt cctgcgcaaa gatatcaacg aagaaaccga agtgatctac  1560
tacccggata acgtgagcgt tgatcaggtg atcctgagca aaaacaccag cgaacatggt  1620
cagctggatc tgctgtatcc gagcattgat agcgaaagcg aaattctgcc gggcgaaaac  1680
caggtgtttt acgataaccg tacccagaac gtggattacc tgaacagcta ttactacctg  1740
gaaagccaga aactgagcga taacgtggaa gattttacct ttacccgcag cattgaagaa  1800
gcgctggata cagcgcgaa agtttacacc tattttccga ccctggcgaa caaagttaat  1860
gcgggtgttc agggcggtct gtttctgatg tgggcgaacg atgtggtgga agatttcacc  1920
accaacatcc tgcgtaaaga tacctggat aaaatcagcg atgttagcgc gattattccg  1980
tatattggtc cggcgctgaa cattagcaat agcgtgcgtc gtggcaattt taccgaagcg  2040
tttgcggtta ccggtgtgac cattctgctg aagcgtttc cggaatttac cattccggcg  2100
ctgggtgcgt ttgtgatcta tagcaaagtg caggaacgca acgaaatcat caaaaccatc  2160
gataactgcc tggaacagcg tattaaacgc tggaaagata gctatgaatg gatgatgggc  2220
acctggctga ccgtattat cacccagttc aacaacatca gctaccagat gtacgatagc  2280
ctgaactatc aggcgggtgc gattaaagcg aaaatcgatc tggaatacaa aaaatacagc  2340
ggcagcgata agaaaacat caaaagccag gttgaaaacc tgaaaacag cctggatgtg  2400
aaaattagcg aagcgatgaa taacatcaac aaattcatcc gcgaatgcag cgtgacctac  2460
ctgttcaaaa acatgctgcc gaaagtgatc gatgaactga cgaatttga tcgcaacacc  2520
aaagcgaaac tgatcaacct gatcgatagc cacaacatta ttctggtggg cgaagtggat  2580
aaactgaaag cgaaagttaa caacagcttc agaacacca tcccgtttaa catcttcagc  2640
tataccaaca acagcctgct gaaagatatc atcaacgaat acttcaatct agaagcacta  2700
gcgagtgggc accatcacca tcaccattaa tgaaagctt                          2739
```

<210> SEQ ID NO 18
<211> LENGTH: 911
<212> TYPE: PRT
<213> ORGANISM: artificial sequence
<220> FEATURE:
<223> OTHER INFORMATION: Protein sequence of the CP cyclicRGD-C fusion

<400> SEQUENCE: 18

```
Gly Ser Glu Phe Met Pro Ile Thr Ile Asn Asn Phe Asn Tyr Ser Asp
1               5                   10                  15
Pro Val Asp Asn Lys Asn Ile Leu Tyr Leu Asp Thr His Leu Asn Thr
            20                  25                  30
Leu Ala Asn Glu Pro Glu Lys Ala Phe Arg Ile Thr Gly Asn Ile Trp
        35                  40                  45
Val Ile Pro Asp Arg Phe Ser Arg Asn Ser Asn Pro Asn Leu Asn Lys
    50                  55                  60
Pro Pro Arg Val Thr Ser Pro Lys Ser Gly Tyr Tyr Asp Pro Asn Tyr
65                  70                  75                  80
Leu Ser Thr Asp Ser Asp Lys Asp Thr Phe Leu Lys Glu Ile Ile Lys
                85                  90                  95
Leu Phe Lys Arg Ile Asn Ser Arg Glu Ile Gly Glu Glu Leu Ile Tyr
            100                 105                 110
Arg Leu Ser Thr Asp Ile Pro Phe Pro Gly Asn Asn Thr Pro Ile
            115                 120                 125
```

```
Asn Thr Phe Asp Phe Asp Val Asp Phe Asn Ser Val Asp Val Lys Thr
    130                 135                 140

Arg Gln Gly Asn Asn Trp Val Lys Thr Gly Ser Ile Asn Pro Ser Val
145                 150                 155                 160

Ile Ile Thr Gly Pro Arg Glu Asn Ile Ile Asp Pro Glu Thr Ser Thr
                165                 170                 175

Phe Lys Leu Thr Asn Asn Thr Phe Ala Ala Gln Glu Gly Phe Gly Ala
                180                 185                 190

Leu Ser Ile Ile Ser Ile Ser Pro Arg Phe Met Leu Thr Tyr Ser Asn
            195                 200                 205

Ala Thr Asn Asp Val Gly Glu Gly Arg Phe Ser Lys Ser Glu Phe Cys
    210                 215                 220

Met Asp Pro Ile Leu Ile Leu Met His Glu Leu Asn His Ala Met His
225                 230                 235                 240

Asn Leu Tyr Gly Ile Ala Ile Pro Asn Asp Gln Thr Ile Ser Ser Val
                245                 250                 255

Thr Ser Asn Ile Phe Tyr Ser Gln Tyr Asn Val Lys Leu Glu Tyr Ala
                260                 265                 270

Glu Ile Tyr Ala Phe Gly Gly Pro Thr Ile Asp Leu Ile Pro Lys Ser
            275                 280                 285

Ala Arg Lys Tyr Phe Glu Glu Lys Ala Leu Asp Tyr Tyr Arg Ser Ile
    290                 295                 300

Ala Lys Arg Leu Asn Ser Ile Thr Thr Ala Asn Pro Ser Ser Phe Asn
305                 310                 315                 320

Lys Tyr Ile Gly Glu Tyr Lys Gln Lys Leu Ile Arg Lys Tyr Arg Phe
                325                 330                 335

Val Val Glu Ser Ser Gly Glu Val Thr Val Asn Arg Asn Lys Phe Val
                340                 345                 350

Glu Leu Tyr Asn Glu Leu Thr Gln Ile Phe Thr Glu Phe Asn Tyr Ala
            355                 360                 365

Lys Ile Tyr Asn Val Gln Asn Arg Lys Ile Tyr Leu Ser Asn Val Tyr
    370                 375                 380

Thr Pro Val Thr Ala Asn Ile Leu Asp Asp Asn Val Tyr Asp Ile Gln
385                 390                 395                 400

Asn Gly Phe Asn Ile Pro Lys Ser Asn Leu Asn Val Leu Phe Met Gly
                405                 410                 415

Gln Asn Leu Ser Arg Asn Pro Ala Leu Arg Lys Val Asn Pro Glu Asn
            420                 425                 430

Met Leu Tyr Leu Phe Thr Lys Phe Cys Val Asp Ala Ile Asp Gly Arg
    435                 440                 445

Gly Gly Cys Arg Gly Asp Met Phe Gly Cys Ala Ala Leu Ala Gly Gly
450                 455                 460

Gly Gly Ser Gly Gly Gly Ser Gly Gly Gly Ser Ala Leu Val
465                 470                 475                 480

Leu Gln Cys Arg Glu Leu Leu Val Lys Asn Thr Asp Leu Pro Phe Ile
                485                 490                 495

Gly Asp Ile Ser Asp Val Lys Thr Asp Ile Phe Leu Arg Lys Asp Ile
            500                 505                 510

Asn Glu Glu Thr Glu Val Ile Tyr Tyr Pro Asp Asn Val Ser Val Asp
    515                 520                 525

Gln Val Ile Leu Ser Lys Asn Thr Ser Glu His Gly Gln Leu Asp Leu
530                 535                 540
```

Leu Tyr Pro Ser Ile Asp Ser Glu Ser Glu Ile Leu Pro Gly Glu Asn
545                 550                 555                 560

Gln Val Phe Tyr Asp Asn Arg Thr Gln Asn Val Asp Tyr Leu Asn Ser
            565                 570                 575

Tyr Tyr Tyr Leu Glu Ser Gln Lys Leu Ser Asp Asn Val Glu Asp Phe
            580                 585                 590

Thr Phe Thr Arg Ser Ile Glu Glu Ala Leu Asp Asn Ser Ala Lys Val
        595                 600                 605

Tyr Thr Tyr Phe Pro Thr Leu Ala Asn Lys Val Asn Ala Gly Val Gln
        610                 615                 620

Gly Gly Leu Phe Leu Met Trp Ala Asn Asp Val Val Glu Asp Phe Thr
625                 630                 635                 640

Thr Asn Ile Leu Arg Lys Asp Thr Leu Asp Lys Ile Ser Asp Val Ser
            645                 650                 655

Ala Ile Ile Pro Tyr Ile Gly Pro Ala Leu Asn Ile Ser Asn Ser Val
            660                 665                 670

Arg Arg Gly Asn Phe Thr Glu Ala Phe Ala Val Thr Gly Val Thr Ile
            675                 680                 685

Leu Leu Glu Ala Phe Pro Glu Phe Thr Ile Pro Ala Leu Gly Ala Phe
690                 695                 700

Val Ile Tyr Ser Lys Val Gln Glu Arg Asn Glu Ile Ile Lys Thr Ile
705                 710                 715                 720

Asp Asn Cys Leu Glu Gln Arg Ile Lys Arg Trp Lys Asp Ser Tyr Glu
            725                 730                 735

Trp Met Met Gly Thr Trp Leu Ser Arg Ile Ile Thr Gln Phe Asn Asn
            740                 745                 750

Ile Ser Tyr Gln Met Tyr Asp Ser Leu Asn Tyr Gln Ala Gly Ala Ile
            755                 760                 765

Lys Ala Lys Ile Asp Leu Glu Tyr Lys Lys Tyr Ser Gly Ser Asp Lys
            770                 775                 780

Glu Asn Ile Lys Ser Gln Val Glu Asn Leu Lys Asn Ser Leu Asp Val
785                 790                 795                 800

Lys Ile Ser Glu Ala Met Asn Asn Ile Asn Lys Phe Ile Arg Glu Cys
            805                 810                 815

Ser Val Thr Tyr Leu Phe Lys Asn Met Leu Pro Lys Val Ile Asp Glu
            820                 825                 830

Leu Asn Glu Phe Asp Arg Asn Thr Lys Ala Lys Leu Ile Asn Leu Ile
            835                 840                 845

Asp Ser His Asn Ile Ile Leu Val Gly Glu Val Asp Lys Leu Lys Ala
850                 855                 860

Lys Val Asn Asn Ser Phe Gln Asn Thr Ile Pro Phe Asn Ile Phe Ser
865                 870                 875                 880

Tyr Thr Asn Asn Ser Leu Leu Lys Asp Ile Ile Asn Glu Tyr Phe Asn
            885                 890                 895

Leu Glu Ala Leu Ala Ser Gly His His His His His Lys Leu
            900                 905                 910

<210> SEQ ID NO 19
<211> LENGTH: 150
<212> TYPE: DNA
<213> ORGANISM: artificial sequence
<220> FEATURE:
<223> OTHER INFORMATION: DNA sequence of the CP THALWHT-C linker

<400> SEQUENCE: 19

```
ggatccacgc acgtcgacgc gattgatggt cgtactcacg ctctgtggca caccgcgcta    60
gcgggcggtg gcggtagcgg cggtggcggt agcggcggtg gcggtagcgc actagtgctg   120
cagacgcacg gtctagaatg ataaaagctt                                    150
```

<210> SEQ ID NO 20
<211> LENGTH: 2727
<212> TYPE: DNA
<213> ORGANISM: artificial sequence
<220> FEATURE:
<223> OTHER INFORMATION: DNA sequence of the CP THALWHT-C fusion

<400> SEQUENCE: 20

```
ggatccgaat tcatgccgat caccatcaac aacttcaact acagcgatcc ggtggataac    60
aaaaacatcc tgtacctgga tacccatctg aatcccctgg cgaacgaacc ggaaaaagcg   120
tttcgtatca ccggcaacat ttgggttatt ccggatcgtt ttagccgtaa cagcaacccg   180
aatctgaata accgccgcg tgttaccagc ccgaaaagcg gttattacga tccgaactat   240
ctgagcaccg atagcgataa agataccttc ctgaaagaaa tcatcaaact gttcaaacgc   300
atcaacagcc gtgaaattgg cgaagaactg atctatcgcc tgagcaccga tattccgttt   360
ccgggcaaca caacacccc gatcaacacc tttgatttcg atgtggattt caacagcgtt   420
gatgttaaaa cccgccaggg taacaattgg gtgaaaaccg gcagcattaa cccgagcgtg   480
attattaccg gtccgcgcga aaacattatt gatccggaaa ccagcacctt taaactgacc   540
aacaacacct tgcggcgca ggaaggtttt ggcgcgctga gcattattag cattagcccg   600
cgctttatgc tgacctatag caacgcgacc aacgatgttg tgaaggccg tttcagcaaa   660 agcgaatttt gcatggaccc gatcctgatc ctgatgcatg aactgaacca tgcgatgcat   720
aacctgtatg gcatcgcgat tccgaacgat cagaccatta gcagcgtgac cagcaacatc   780
ttttacagcc agtacaacgt gaaactggaa tatgcggaaa tctatgcgtt ggcggtccg   840 accattgatc tgattccgaa aagcgcgcgc aaatacttcg aagaaaaagc gctggattac   900
tatcgcagca ttgcgaaacg tctgaacagc attaccaccg cgaatccgag cagcttcaac   960
aaatatatcg cgaatataaa acagaaactg atccgcaaat atcgctttgt ggtggaaagc  1020
agcggcgaag ttaccgttaa ccgcaataaa ttcgtggaac tgtacaacga actgacccag  1080
atcttcaccg aatttaacta tgcgaaaatc tataacgtgc agaaccgtaa atctacctg   1140 agcaacgtgt ataccccggt gaccgcgaat attctggatg ataacgtgta cgatatccag  1200
aacggcttta acatcccgaa aagcaacctg aacgttctgt tatgggcca gaacctgagc  1260 cgtaatccgg cgctgcgtaa agtgaacccg gaaaacatgc tgtacctgtt caccaaattt  1320
tgcgtcgacg cgattgatgg tcgtactcac gctctgtggc acaccgcgct agcgggcggt  1380
ggcggtagcg gcggtggcgg tagcggcggt ggcggtagcg cactagtgct gcagtgtcgt  1440
gaactgctgg tgaaaaacac cgatctgccg tttattggcg atatcagcga tgtgaaaacc  1500
gatatcttcc tgcgcaaaga tatcaacgaa gaaaccgaag tgatctacta cccggataac  1560
gtgagcgttg atcaggtgat cctgagcaaa acaccagcg aacatggtca gctggatctg  1620
ctgtatccga gcattgatag cgaaagcgaa attctgccgg cgaaaaccag gtgttttac  1680 gataaccgta cccagaacgt ggattacctg aacagctatt actacctgga aagccagaaa  1740
ctgagcgata acgtggaaga tttttacctt acccgcagca ttgaagaagc gctggataac  1800
agcgcgaaag tttacaccta ttttccgacc ctggcgaaca agttaatgc gggtgttcag  1860 ggcggtctgt ttctgatgtg ggcgaacgat gtggtggaag atttcaccac caacatcctg  1920
```

-continued

```
cgtaaagata ccctggataa aatcagcgat gttagcgcga ttattccgta tattggtccg    1980
gcgctgaaca ttagcaatag cgtgcgtcgt ggcaatttta ccgaagcgtt tgcggttacc    2040
ggtgtgacca ttctgctgga agcgtttccg gaatttacca ttccggcgct gggtgcgttt    2100
gtgatctata gcaaagtgca ggaacgcaac gaaatcatca aaaccatcga taactgcctg    2160
gaacagcgta ttaaacgctg gaaagatagc tatgaatgga tgatgggcac ctggctgagc    2220
cgtattatca cccagttcaa caacatcagc taccagatgt acgatagcct gaactatcag    2280
gcgggtgcga ttaaagcgaa aatcgatctg gaatacaaaa atacagcgg cagcgataaa    2340
gaaaacatca aaagccaggt tgaaaacctg aaaaacagcc tggatgtgaa aattagcgaa    2400
gcgatgaata acatcaacaa attcatccgc gaatgcagcg tgacctacct gttcaaaaac    2460
atgctgccga agtgatcga tgaactgaac gaatttgatc gcaacaccaa agcgaaactg    2520
atcaacctga tcgatagcca acacattatt ctggtgggcg aagtggataa actgaaagcg    2580
aaagttaaca acagcttcca gaacaccatc ccgtttaaca tcttcagcta taccaacaac    2640
agcctgctga agatatcat caacgaatac ttcaatctag aagcactagc gagtgggcac    2700
catcaccatc accattaatg aaagctt                                        2727
```

<210> SEQ ID NO 21
<211> LENGTH: 907
<212> TYPE: PRT
<213> ORGANISM: artificial sequence
<220> FEATURE:
<223> OTHER INFORMATION: Protein sequence of the CP THALWHT-C fusion

<400> SEQUENCE: 21

```
Gly Ser Glu Phe Met Pro Ile Thr Ile Asn Asn Phe Asn Tyr Ser Asp
1               5                  10                  15

Pro Val Asp Asn Lys Asn Ile Leu Tyr Leu Asp Thr His Leu Asn Thr
            20                  25                  30

Leu Ala Asn Glu Pro Glu Lys Ala Phe Arg Ile Thr Gly Asn Ile Trp
        35                  40                  45

Val Ile Pro Asp Arg Phe Ser Arg Asn Ser Asn Pro Asn Leu Asn Lys
    50                  55                  60

Pro Pro Arg Val Thr Ser Pro Lys Ser Gly Tyr Tyr Asp Pro Asn Tyr
65                  70                  75                  80

Leu Ser Thr Asp Ser Asp Lys Asp Thr Phe Leu Lys Glu Ile Ile Lys
                85                  90                  95

Leu Phe Lys Arg Ile Asn Ser Arg Glu Ile Gly Glu Glu Leu Ile Tyr
            100                 105                 110

Arg Leu Ser Thr Asp Ile Pro Phe Pro Gly Asn Asn Asn Thr Pro Ile
        115                 120                 125

Asn Thr Phe Asp Phe Asp Val Asp Phe Asn Ser Val Asp Val Lys Thr
    130                 135                 140

Arg Gln Gly Asn Asn Trp Val Lys Thr Gly Ser Ile Asn Pro Ser Val
145                 150                 155                 160

Ile Ile Thr Gly Pro Arg Glu Asn Ile Ile Asp Pro Glu Thr Ser Thr
                165                 170                 175

Phe Lys Leu Thr Asn Asn Thr Phe Ala Ala Gln Glu Gly Phe Gly Ala
            180                 185                 190

Leu Ser Ile Ile Ser Ile Ser Pro Arg Phe Met Leu Thr Tyr Ser Asn
        195                 200                 205

Ala Thr Asn Asp Val Gly Glu Gly Arg Phe Ser Lys Ser Glu Phe Cys
```

-continued

```
            210                 215                 220
Met Asp Pro Ile Leu Ile Leu Met His Glu Leu Asn His Ala Met His
225                 230                 235                 240

Asn Leu Tyr Gly Ile Ala Ile Pro Asn Asp Gln Thr Ile Ser Ser Val
                245                 250                 255

Thr Ser Asn Ile Phe Tyr Ser Gln Tyr Asn Val Lys Leu Glu Tyr Ala
            260                 265                 270

Glu Ile Tyr Ala Phe Gly Gly Pro Thr Ile Asp Leu Ile Pro Lys Ser
        275                 280                 285

Ala Arg Lys Tyr Phe Glu Glu Lys Ala Leu Asp Tyr Tyr Arg Ser Ile
        290                 295                 300

Ala Lys Arg Leu Asn Ser Ile Thr Thr Ala Asn Pro Ser Ser Phe Asn
305                 310                 315                 320

Lys Tyr Ile Gly Glu Tyr Lys Gln Lys Leu Ile Arg Lys Tyr Arg Phe
                325                 330                 335

Val Val Glu Ser Ser Gly Glu Val Thr Val Asn Arg Asn Lys Phe Val
                340                 345                 350

Glu Leu Tyr Asn Glu Leu Thr Gln Ile Phe Thr Glu Phe Asn Tyr Ala
            355                 360                 365

Lys Ile Tyr Asn Val Gln Asn Arg Lys Ile Tyr Leu Ser Asn Val Tyr
        370                 375                 380

Thr Pro Val Thr Ala Asn Ile Leu Asp Asp Asn Val Tyr Asp Ile Gln
385                 390                 395                 400

Asn Gly Phe Asn Ile Pro Lys Ser Asn Leu Asn Val Leu Phe Met Gly
                405                 410                 415

Gln Asn Leu Ser Arg Asn Pro Ala Leu Arg Lys Val Asn Pro Glu Asn
            420                 425                 430

Met Leu Tyr Leu Phe Thr Lys Phe Cys Val Asp Ala Ile Asp Gly Arg
        435                 440                 445

Thr His Ala Leu Trp His Thr Ala Leu Ala Gly Gly Gly Gly Ser Gly
        450                 455                 460

Gly Gly Gly Ser Gly Gly Gly Gly Ser Ala Leu Val Leu Gln Cys Arg
465                 470                 475                 480

Glu Leu Leu Val Lys Asn Thr Asp Leu Pro Phe Ile Gly Asp Ile Ser
                485                 490                 495

Asp Val Lys Thr Asp Ile Phe Leu Arg Lys Asp Ile Asn Glu Glu Thr
            500                 505                 510

Glu Val Ile Tyr Tyr Pro Asp Asn Val Ser Val Asp Gln Val Ile Leu
        515                 520                 525

Ser Lys Asn Thr Ser Glu His Gly Gln Leu Asp Leu Leu Tyr Pro Ser
530                 535                 540

Ile Asp Ser Glu Ser Glu Ile Leu Pro Gly Glu Asn Gln Val Phe Tyr
545                 550                 555                 560

Asp Asn Arg Thr Gln Asn Val Asp Tyr Leu Asn Ser Tyr Tyr Tyr Leu
                565                 570                 575

Glu Ser Gln Lys Leu Ser Asp Asn Val Glu Asp Phe Thr Phe Thr Arg
            580                 585                 590

Ser Ile Glu Glu Ala Leu Asp Asn Ser Ala Lys Val Tyr Thr Tyr Phe
        595                 600                 605

Pro Thr Leu Ala Asn Lys Val Asn Ala Gly Val Gln Gly Gly Leu Phe
        610                 615                 620

Leu Met Trp Ala Asn Asp Val Val Glu Asp Phe Thr Thr Asn Ile Leu
625                 630                 635                 640
```

```
Arg Lys Asp Thr Leu Asp Lys Ile Ser Asp Val Ser Ala Ile Ile Pro
                645                 650                 655
Tyr Ile Gly Pro Ala Leu Asn Ile Ser Asn Ser Val Arg Arg Gly Asn
            660                 665                 670
Phe Thr Glu Ala Phe Ala Val Thr Gly Val Thr Ile Leu Leu Glu Ala
        675                 680                 685
Phe Pro Glu Phe Thr Ile Pro Ala Leu Gly Ala Phe Val Ile Tyr Ser
    690                 695                 700
Lys Val Gln Glu Arg Asn Glu Ile Ile Lys Thr Ile Asp Asn Cys Leu
705                 710                 715                 720
Glu Gln Arg Ile Lys Arg Trp Lys Asp Ser Tyr Glu Trp Met Met Gly
                725                 730                 735
Thr Trp Leu Ser Arg Ile Ile Thr Gln Phe Asn Asn Ile Ser Tyr Gln
            740                 745                 750
Met Tyr Asp Ser Leu Asn Tyr Gln Ala Gly Ala Ile Lys Ala Lys Ile
        755                 760                 765
Asp Leu Glu Tyr Lys Lys Tyr Ser Gly Ser Asp Lys Glu Asn Ile Lys
    770                 775                 780
Ser Gln Val Glu Asn Leu Lys Asn Ser Leu Asp Val Lys Ile Ser Glu
785                 790                 795                 800
Ala Met Asn Asn Ile Asn Lys Phe Ile Arg Glu Cys Ser Val Thr Tyr
                805                 810                 815
Leu Phe Lys Asn Met Leu Pro Lys Val Ile Asp Glu Leu Asn Glu Phe
            820                 825                 830
Asp Arg Asn Thr Lys Ala Lys Leu Ile Asn Leu Ile Asp Ser His Asn
        835                 840                 845
Ile Ile Leu Val Gly Glu Val Asp Lys Leu Lys Ala Lys Val Asn Asn
    850                 855                 860
Ser Phe Gln Asn Thr Ile Pro Phe Asn Ile Phe Ser Tyr Thr Asn Asn
865                 870                 875                 880
Ser Leu Leu Lys Asp Ile Ile Asn Glu Tyr Phe Asn Leu Glu Ala Leu
                885                 890                 895
Ala Ser Gly His His His His His His Lys Leu
            900                 905

<210> SEQ ID NO 22
<211> LENGTH: 156
<212> TYPE: DNA
<213> ORGANISM: artificial sequence
<220> FEATURE:
<223> OTHER INFORMATION: DNA sequence of the CP cyclicTHALWHT-C linker

<400> SEQUENCE: 22
ggatccacgc acgtcgacgc gattgatggt cgttgtactc acgctctgtg gcacacctgc      60
gcgctagcgg gcggtggcgg tagcggcggt ggcggtagcg gcggtggcgg tagcgcacta     120
gtgctgcaga cgcacggtct agaatgataa aagctt                               156

<210> SEQ ID NO 23
<211> LENGTH: 2733
<212> TYPE: DNA
<213> ORGANISM: artificial sequence
<220> FEATURE:
<223> OTHER INFORMATION: DNA sequence of the CP cyclicTHALWHT-C fusion

<400> SEQUENCE: 23
ggatccgaat tcatgccgat caccatcaac aacttcaact acagcgatcc ggtggataac      60
```

```
aaaaacatcc tgtacctgga tacccatctg aatacctgg cgaacgaacc ggaaaaagcg      120
tttcgtatca ccggcaacat ttgggttatt ccgatcgtt ttagccgtaa cagcaacccg      180
aatctgaata aaccgccgcg tgttaccagc ccgaaaagcg gttattacga tccgaactat      240
ctgagcaccg atagcgataa agataccttc ctgaaagaaa tcatcaaact gttcaaacgc      300
atcaacagcc gtgaaattgg cgaagaactg atctatcgcc tgagcaccga tattccgttt      360 ccggcaaca caacacccc gatcaacacc tttgatttcg atgtggattt caacagcgtt      420
gatgttaaaa cccgccaggg taacaattgg gtgaaaaccg gcagcattaa cccgagcgtg      480
attattaccg gtccgcgcga aaacattatt gatccggaaa ccagcacctt taaactgacc      540
aacaacacct tgcggcgca ggaaggtttt ggcgcgctga gcattattag cattagcccg      600
cgctttatgc tgacctatag caacgcgacc aacgatgttg tgaaggccg tttcagcaaa      660 agcgaatttt gcatggaccc gatcctgatc ctgatgcatg aactgaacca tgcgatgcat      720
aacctgtatg gcatcgcgat tccgaacgat cagaccatta gcagcgtgac cagcaacatc      780
ttttacagcc agtacaacgt gaaactggaa tatgcggaaa tctatgcgtt ggcggtccg      840 accattgatc tgattccgaa aagcgcgcgc aaatacttcg aagaaaaagc gctggattac      900
tatcgcagca ttgcgaaacg tctgaacagc attaccaccg cgaatccgag cagcttcaac      960
aaatatatcg gcgaatataa acagaaactg atccgcaaat atcgctttgt ggtggaaagc      1020
agcggcgaag ttaccgttaa ccgcaataaa ttcgtggaac tgtacaacga actgacccag      1080
atcttcaccg aatttaacta tgcgaaaatc tataacgtgc agaaccgtaa aatctacctg      1140
agcaacgtgt atacccggt gaccgcgaat attctggatg ataacgtgta cgatatccag      1200
aacggcttta acatcccgaa aagcaacctg aacgttctgt tatgggcca gaacctgagc      1260 cgtaatccgg cgctgcgtaa agtgaacccg gaaaacatgc tgtacctgtt caccaaattt      1320
tgcgtcgacg cgattgatgg tcgttgtact cacgctctgt ggcacacctg cgcgctagcg      1380
ggcggtggcg gtagcggcgg tggcggtagc ggcggtggcg gtagcgcact agtgctgcag      1440
tgtcgtgaac tgctggtgaa aaacaccgat ctgccgttta ttggcgatat cagcgatgtg      1500
aaaaccgata tcttcctgcg caaagatatc aacgaagaaa ccgaagtgat ctactacccg      1560
gataacgtga cgcttgatca ggtgatcctg agcaaaaaca ccagcgaaca tggtcagctg      1620
gatctgctgt atccgagcat tgatagcgaa agcgaaattc tgccgggcga aaaccaggtg      1680
ttttacgata ccgtacccca gaacgtggat tacctgaaca gctattacta cctggaaagc      1740
cagaaactga gcgataacgt ggaagatttt acctttaccc gcagcattga agaagcgctg      1800
gataacagcg cgaaagttta cacctatttt ccgaccctgg cgaacaaagt taatgcgggt      1860
gttcagggcg gtctgttct gatgtgggcg aacgatgtgg tggaagattt caccaccaac      1920
atcctgcgta aagataccct ggataaaatc agcgatgtta gcgcgattat tccgtatatt      1980
ggtccggcgc tgaacattag caatagcgtg cgtcgtggca ttttaccga agcgtttgcg      2040 gttaccggtg tgaccattct gctggaagcg tttccggaat ttaccattcc ggcgctgggt      2100
gcgtttgtga tctatagcaa agtgcaggaa cgcaacgaaa tcatcaaaac catcgataac      2160
tgcctggaac agcgtattaa acgctggaaa gatagctatg aatggatgat gggcacctgg      2220
ctgagccgta ttatcaccca gttcaacaac atcagctacc agatgtacga tagcctgaac      2280
tatcaggcgg gtgcgattaa agcgaaaatc gatctggaat acaaaaaata cagcggcagc      2340
gataaagaaa acatcaaaag ccaggttgaa aacctgaaaa acagcctgga tgtgaaaatt      2400
```

```
agcgaagcga tgaataacat caacaaattc atccgcgaat gcagcgtgac ctacctgttc    2460
aaaaacatgc tgccgaaagt gatcgatgaa ctgaacgaat ttgatcgcaa caccaaagcg    2520
aaactgatca acctgatcga tagccacaac attattctgg tgggcgaagt ggataaactg    2580
aaagcgaaag ttaacaacag cttccagaac accatcccgt ttaacatctt cagctatacc    2640
aacaacagcc tgctgaaaga tatcatcaac gaatacttca atctagaagc actagcgagt    2700
gggcaccatc accatcacca ttaatgaaag ctt                                 2733
```

<210> SEQ ID NO 24
<211> LENGTH: 909
<212> TYPE: PRT
<213> ORGANISM: artificial sequence
<220> FEATURE:
<223> OTHER INFORMATION: Protein sequence of the CP cyclicTHALWHT-C fusion

<400> SEQUENCE: 24

```
Gly Ser Glu Phe Met Pro Ile Thr Ile Asn Asn Phe Asn Tyr Ser Asp
1               5                   10                  15

Pro Val Asp Asn Lys Asn Ile Leu Tyr Leu Asp Thr His Leu Asn Thr
            20                  25                  30

Leu Ala Asn Glu Pro Glu Lys Ala Phe Arg Ile Thr Gly Asn Ile Trp
        35                  40                  45

Val Ile Pro Asp Arg Phe Ser Arg Asn Ser Asn Pro Asn Leu Asn Lys
    50                  55                  60

Pro Pro Arg Val Thr Ser Pro Lys Ser Gly Tyr Tyr Asp Pro Asn Tyr
65                  70                  75                  80

Leu Ser Thr Asp Ser Asp Lys Asp Thr Phe Leu Lys Glu Ile Ile Lys
                85                  90                  95

Leu Phe Lys Arg Ile Asn Ser Arg Glu Ile Gly Glu Glu Leu Ile Tyr
            100                 105                 110

Arg Leu Ser Thr Asp Ile Pro Phe Pro Gly Asn Asn Asn Thr Pro Ile
        115                 120                 125

Asn Thr Phe Asp Phe Asp Val Asp Phe Asn Ser Val Asp Val Lys Thr
    130                 135                 140

Arg Gln Gly Asn Asn Trp Val Lys Thr Gly Ser Ile Asn Pro Ser Val
145                 150                 155                 160

Ile Ile Thr Gly Pro Arg Glu Asn Ile Ile Asp Pro Glu Thr Ser Thr
                165                 170                 175

Phe Lys Leu Thr Asn Asn Thr Phe Ala Ala Gln Glu Gly Phe Gly Ala
            180                 185                 190

Leu Ser Ile Ile Ser Ile Ser Pro Arg Phe Met Leu Thr Tyr Ser Asn
        195                 200                 205

Ala Thr Asn Asp Val Gly Glu Gly Arg Phe Ser Lys Ser Glu Phe Cys
    210                 215                 220

Met Asp Pro Ile Leu Ile Leu Met His Glu Leu Asn His Ala Met His
225                 230                 235                 240

Asn Leu Tyr Gly Ile Ala Ile Pro Asn Asp Gln Thr Ile Ser Ser Val
                245                 250                 255

Thr Ser Asn Ile Phe Tyr Ser Gln Tyr Asn Val Lys Leu Glu Tyr Ala
            260                 265                 270

Glu Ile Tyr Ala Phe Gly Gly Pro Thr Ile Asp Leu Ile Pro Lys Ser
        275                 280                 285

Ala Arg Lys Tyr Phe Glu Glu Lys Ala Leu Asp Tyr Tyr Arg Ser Ile
    290                 295                 300
```

```
Ala Lys Arg Leu Asn Ser Ile Thr Thr Ala Asn Pro Ser Ser Phe Asn
305                 310                 315                 320

Lys Tyr Ile Gly Glu Tyr Lys Gln Lys Leu Ile Arg Lys Tyr Arg Phe
                325                 330                 335

Val Val Glu Ser Ser Gly Glu Val Thr Val Asn Arg Asn Lys Phe Val
            340                 345                 350

Glu Leu Tyr Asn Glu Leu Thr Gln Ile Phe Thr Glu Phe Asn Tyr Ala
        355                 360                 365

Lys Ile Tyr Asn Val Gln Asn Arg Lys Ile Tyr Leu Ser Asn Val Tyr
370                 375                 380

Thr Pro Val Thr Ala Asn Ile Leu Asp Asp Asn Val Tyr Asp Ile Gln
385                 390                 395                 400

Asn Gly Phe Asn Ile Pro Lys Ser Asn Leu Asn Val Leu Phe Met Gly
                405                 410                 415

Gln Asn Leu Ser Arg Asn Pro Ala Leu Arg Lys Val Asn Pro Glu Asn
            420                 425                 430

Met Leu Tyr Leu Phe Thr Lys Phe Cys Val Asp Ala Ile Asp Gly Arg
        435                 440                 445

Cys Thr His Ala Leu Trp His Thr Cys Ala Leu Ala Gly Gly Gly Gly
450                 455                 460

Ser Gly Gly Gly Gly Ser Gly Gly Gly Ser Ala Leu Val Leu Gln
465                 470                 475                 480

Cys Arg Glu Leu Leu Val Lys Asn Thr Asp Leu Pro Phe Ile Gly Asp
                485                 490                 495

Ile Ser Asp Val Lys Thr Asp Ile Phe Leu Arg Lys Asp Ile Asn Glu
            500                 505                 510

Glu Thr Glu Val Ile Tyr Tyr Pro Asp Asn Val Ser Val Asp Gln Val
        515                 520                 525

Ile Leu Ser Lys Asn Thr Ser Glu His Gly Gln Leu Asp Leu Leu Tyr
530                 535                 540

Pro Ser Ile Asp Ser Glu Ser Glu Ile Leu Pro Gly Glu Asn Gln Val
545                 550                 555                 560

Phe Tyr Asp Asn Arg Thr Gln Asn Val Asp Tyr Leu Asn Ser Tyr Tyr
                565                 570                 575

Tyr Leu Glu Ser Gln Lys Leu Ser Asp Asn Val Glu Asp Phe Thr Phe
            580                 585                 590

Thr Arg Ser Ile Glu Glu Ala Leu Asp Asn Ser Ala Lys Val Tyr Thr
        595                 600                 605

Tyr Phe Pro Thr Leu Ala Asn Lys Val Asn Ala Gly Val Gln Gly Gly
610                 615                 620

Leu Phe Leu Met Trp Ala Asn Asp Val Val Glu Asp Phe Thr Thr Asn
625                 630                 635                 640

Ile Leu Arg Lys Asp Thr Leu Asp Lys Ile Ser Asp Val Ser Ala Ile
                645                 650                 655

Ile Pro Tyr Ile Gly Pro Ala Leu Asn Ile Ser Asn Ser Val Arg Arg
            660                 665                 670

Gly Asn Phe Thr Glu Ala Phe Ala Val Thr Gly Val Thr Ile Leu Leu
        675                 680                 685

Glu Ala Phe Pro Glu Phe Thr Ile Pro Ala Leu Gly Ala Phe Val Ile
            690                 695                 700

Tyr Ser Lys Val Gln Glu Arg Asn Glu Ile Ile Lys Thr Ile Asp Asn
705                 710                 715                 720

Cys Leu Glu Gln Arg Ile Lys Arg Trp Lys Asp Ser Tyr Glu Trp Met
```

```
                     725                 730                 735
Met Gly Thr Trp Leu Ser Arg Ile Ile Thr Gln Phe Asn Asn Ile Ser
                 740                 745                 750

Tyr Gln Met Tyr Asp Ser Leu Asn Tyr Gln Ala Gly Ala Ile Lys Ala
             755                 760                 765

Lys Ile Asp Leu Glu Tyr Lys Tyr Ser Gly Ser Asp Lys Glu Asn
         770                 775                 780

Ile Lys Ser Gln Val Glu Asn Leu Lys Asn Ser Leu Asp Val Lys Ile
785                 790                 795                 800

Ser Glu Ala Met Asn Asn Ile Asn Lys Phe Ile Arg Glu Cys Ser Val
                 805                 810                 815

Thr Tyr Leu Phe Lys Asn Met Leu Pro Lys Val Ile Asp Glu Leu Asn
                 820                 825                 830

Glu Phe Asp Arg Asn Thr Lys Ala Lys Leu Ile Asn Leu Ile Asp Ser
                 835                 840                 845

His Asn Ile Ile Leu Val Gly Glu Val Asp Lys Leu Lys Ala Lys Val
    850                 855                 860

Asn Asn Ser Phe Gln Asn Thr Ile Pro Phe Asn Ile Phe Ser Tyr Thr
865                 870                 875                 880

Asn Asn Ser Leu Leu Lys Asp Ile Ile Asn Glu Tyr Phe Asn Leu Glu
                 885                 890                 895

Ala Leu Ala Ser Gly His His His His His Lys Leu
                 900                 905

<210> SEQ ID NO 25
<211> LENGTH: 213
<212> TYPE: DNA
<213> ORGANISM: artificial sequence
<220> FEATURE:
<223> OTHER INFORMATION: DNA sequence of the CP ANP-C linker

<400> SEQUENCE: 25
ggatccacgc acgtcgacgc gattgatggt cgttctctgc gtcgttcttc ttgcttcggt    60
ggtcgtatgg accgtatcgg tgctcagtct ggtctgggtt gcaactcttt ccgttacgcg   120
ctagcgggcg gtggcggtag cggcggtggc ggtagcggcg gtggcggtag cgcactagtg   180
ctgcagacgc acggtctaga atgataaaag ctt                                213

<210> SEQ ID NO 26
<211> LENGTH: 2790
<212> TYPE: DNA
<213> ORGANISM: artificial sequence
<220> FEATURE:
<223> OTHER INFORMATION: DNA sequence of the CP ANP-C fusion

<400> SEQUENCE: 26
ggatccgaat tcatgccgat caccatcaac aacttcaact acagcgatcc ggtggataac    60
aaaaacatcc tgtacctgga tacccatctg aatccctggc gaacgaacc ggaaaaagcg    120 tttcgtatca ccggcaacat tgggttatt ccggatcgtt ttagccgtaa cagcaacccg    180
aatctgaata aaccgccgcg tgttaccagc ccgaaaagcg gttattacga tccgaactat   240
ctgagcaccg atagcgataa agataccttc ctgaaagaaa tcatcaaact gttcaaacgc   300
atcaacagcc gtgaaattgg cgaagaactg atctatcgcc tgagcaccga tattccgttt   360
ccgggcaaca caacaccccc gatcaacacc tttgatttcg atgtggattt caacagcgtt   420
gatgttaaaa cccgccaggg taacaattgg gtgaaaaccg gcagcattaa cccgagcgtg   480
```

```
attattaccg gtccgcgcga aaacattatt gatccggaaa ccagcaccett taaactgacc    540 aacaacacct tgcggcgca ggaaggtttt ggcgcgctga gcattattag cattagcccg     600
cgctttatgc tgacctatag caacgcgacc aacgatgttg gtgaaggccg tttcagcaaa    660
agcgaatttt gcatggaccc gatcctgatc ctgatgcatg aactgaacca tgcgatgcat    720
aacctgtatg gcatcgcgat tccgaacgat cagaccatta gcagcgtgac cagcaacatc    780
ttttacagcc agtacaacgt gaaactggaa tatgcgaaaa tctatgcgtt tggcggtccg    840
accattgatc tgattccgaa agcgcgcgc aaatacttcg aagaaaaagc gctggattac     900
tatcgcagca ttgcgaaacg tctgaacagc attaccaccg cgaatccgag cagcttcaac    960
aaatatatcg gcgaatataa acagaaactg atccgcaaat atcgctttgt ggtggaaagc    1020
agcggcgaag ttaccgttaa ccgcaataaa ttcgtggaac tgtacaacga actgacccag    1080
atcttcaccg aatttaacta tgcgaaaatc tataacgtgc agaaccgtaa aatctacctg    1140
agcaacgtgt atacccccggt gaccgcgaat attctggatg ataacgtgta cgatatccag    1200 aacggctta acatcccgaa aagcaacctg aacgttctgt ttatgggcca gaacctgagc    1260
cgtaatccgg cgctgcgtaa agtgaacccg gaaaacatgc tgtacctgtt caccaaattt    1320
tgcgtcgacg cgattgatgg tcgttctctg cgtcgttctt cttgcttcgg tggtcgtatg    1380
gaccgtatcg gtgctcagtc tggtctgggt tgcaactctt ccgttacgc gctagcgggc      1440 ggtggcggta gcggcggtgg cggtagcggc ggtggcggta gcgcactagt gctgcagtgt    1500
cgtgaactgc tggtgaaaaa caccgatctg ccgtttattg gcgatatcag cgatgtgaaa    1560
accgatatct tcctgcgcaa agatatcaac gaagaaaccg aagtgatcta ctacccggat    1620
aacgtgagcg ttgatcaggt gatcctgagc aaaaacacca gcgaacatgg tcagctggat    1680
ctgctgtatc cgagcattga tagcgaaagc gaaattctgc cgggcgaaaa ccaggtgttt    1740
tacgataacc gtacccagaa cgtggattac ctgaacagct attactacct ggaaagccag    1800
aaactgagcg ataacgtgga agattttacc tttacccgca gcattgaaga agcgctggat    1860
aacagcgcga agtttacac ctatttttccg accctggcga caaagttaa tgcgggtgtt      1920 cagggcggtc tgtttctgat gtgggcgaac gatgtggtgg aagatttcac caccaacatc    1980
ctgcgtaaag ataccctgga taaaatcagc gatgttagcg cgattattcc gtatattggt    2040
ccggcgctga acattagcaa tagcgtgcgt cgtggcaatt ttaccgaagc gtttgcggtt    2100
accggtgtga ccattctgct ggaagcgttt ccggaattta ccattccggc gctgggtgcg    2160
tttgtgatct atagcaaagt gcaggaacgc aacgaaatca tcaaaaccat cgataactgc    2220
ctggaacagc gtattaaacg ctggaaagat agctatgaat ggatgatggg cacctggctg    2280
agccgtatta tcacccagtt caacaacatc agctaccaga tgtacgatag cctgaactat    2340
caggcgggtg cgattaaagc gaaaatcgat ctggaataca aaaatacag cggcagcgat     2400 aaagaaaaca tcaaaagcca ggttgaaaac ctgaaaaaca gcctggatgt gaaaattagc    2460
gaagcgatga ataacatcaa caaattcatc cgcgaatgca gcgtgaccta cctgttcaaa    2520
aacatgctgc cgaaagtgat cgatgaactg aacgaatttg atcgcaacac caaagcgaaa    2580
ctgatcaacc tgatcgatag ccacaacatt attctggtgg gcgaagtgga taaactgaaa    2640
gcgaaagtta caacagctt ccagaacacc atcccgttta acatcttcag ctataccaac     2700
aacagcctgc tgaaagatat catcaacgaa tacttcaatc tagaagcact agcgagtggg    2760
caccatcacc atcaccatta atgaaagctt                                     2790
```

-continued

```
<210> SEQ ID NO 27
<211> LENGTH: 928
<212> TYPE: PRT
<213> ORGANISM: artificial sequence
<220> FEATURE:
<223> OTHER INFORMATION: Protein sequence of the CP ANP-C fusion

<400> SEQUENCE: 27
```

Gly Ser Glu Phe Met Pro Ile Thr Ile Asn Asn Phe Asn Tyr Ser Asp
1               5                   10                  15

Pro Val Asp Asn Lys Asn Ile Leu Tyr Leu Asp Thr His Leu Asn Thr
            20                  25                  30

Leu Ala Asn Glu Pro Glu Lys Ala Phe Arg Ile Thr Gly Asn Ile Trp
        35                  40                  45

Val Ile Pro Asp Arg Phe Ser Arg Asn Ser Asn Pro Asn Leu Asn Lys
50                  55                  60

Pro Pro Arg Val Thr Ser Pro Lys Ser Gly Tyr Tyr Asp Pro Asn Tyr
65                  70                  75                  80

Leu Ser Thr Asp Ser Asp Lys Asp Thr Phe Leu Lys Glu Ile Ile Lys
                85                  90                  95

Leu Phe Lys Arg Ile Asn Ser Arg Glu Ile Gly Glu Glu Leu Ile Tyr
            100                 105                 110

Arg Leu Ser Thr Asp Ile Pro Phe Pro Gly Asn Asn Asn Thr Pro Ile
        115                 120                 125

Asn Thr Phe Asp Phe Asp Val Asp Phe Asn Ser Val Asp Val Lys Thr
130                 135                 140

Arg Gln Gly Asn Asn Trp Val Lys Thr Gly Ser Ile Asn Pro Ser Val
145                 150                 155                 160

Ile Ile Thr Gly Pro Arg Glu Asn Ile Ile Asp Pro Glu Thr Ser Thr
                165                 170                 175

Phe Lys Leu Thr Asn Asn Thr Phe Ala Ala Gln Glu Gly Phe Gly Ala
            180                 185                 190

Leu Ser Ile Ile Ser Ile Ser Pro Arg Phe Met Leu Thr Tyr Ser Asn
        195                 200                 205

Ala Thr Asn Asp Val Gly Glu Gly Arg Phe Ser Lys Ser Glu Phe Cys
210                 215                 220

Met Asp Pro Ile Leu Ile Leu Met His Glu Leu Asn His Ala Met His
225                 230                 235                 240

Asn Leu Tyr Gly Ile Ala Ile Pro Asn Asp Gln Thr Ile Ser Ser Val
                245                 250                 255

Thr Ser Asn Ile Phe Tyr Ser Gln Tyr Asn Val Lys Leu Glu Tyr Ala
            260                 265                 270

Glu Ile Tyr Ala Phe Gly Gly Pro Thr Ile Asp Leu Ile Pro Lys Ser
        275                 280                 285

Ala Arg Lys Tyr Phe Glu Glu Lys Ala Leu Asp Tyr Tyr Arg Ser Ile
290                 295                 300

Ala Lys Arg Leu Asn Ser Ile Thr Thr Ala Asn Pro Ser Ser Phe Asn
305                 310                 315                 320

Lys Tyr Ile Gly Glu Tyr Lys Gln Lys Leu Ile Arg Lys Tyr Arg Phe
                325                 330                 335

Val Val Glu Ser Ser Gly Glu Val Thr Val Asn Arg Asn Lys Phe Val
            340                 345                 350

Glu Leu Tyr Asn Glu Leu Thr Gln Ile Phe Thr Glu Phe Asn Tyr Ala
        355                 360                 365

Lys Ile Tyr Asn Val Gln Asn Arg Lys Ile Tyr Leu Ser Asn Val Tyr

```
                370                 375                 380
Thr Pro Val Thr Ala Asn Ile Leu Asp Asp Asn Val Tyr Asp Ile Gln
385                 390                 395                 400

Asn Gly Phe Asn Ile Pro Lys Ser Asn Leu Asn Val Leu Phe Met Gly
                405                 410                 415

Gln Asn Leu Ser Arg Asn Pro Ala Leu Arg Lys Val Asn Pro Glu Asn
            420                 425                 430

Met Leu Tyr Leu Phe Thr Lys Phe Cys Val Asp Ala Ile Asp Gly Arg
        435                 440                 445

Ser Leu Arg Arg Ser Ser Cys Phe Gly Gly Arg Met Asp Arg Ile Gly
    450                 455                 460

Ala Gln Ser Gly Leu Gly Cys Asn Ser Phe Arg Tyr Ala Leu Ala Gly
465                 470                 475                 480

Gly Gly Gly Ser Gly Gly Gly Gly Ser Gly Gly Gly Gly Ser Ala Leu
                485                 490                 495

Val Leu Gln Cys Arg Glu Leu Leu Val Lys Asn Thr Asp Leu Pro Phe
            500                 505                 510

Ile Gly Asp Ile Ser Asp Val Lys Thr Asp Ile Phe Leu Arg Lys Asp
        515                 520                 525

Ile Asn Glu Glu Thr Glu Val Ile Tyr Tyr Pro Asp Asn Val Ser Val
    530                 535                 540

Asp Gln Val Ile Leu Ser Lys Asn Thr Ser Glu His Gly Gln Leu Asp
545                 550                 555                 560

Leu Leu Tyr Pro Ser Ile Asp Ser Glu Ser Glu Ile Leu Pro Gly Glu
                565                 570                 575

Asn Gln Val Phe Tyr Asp Asn Arg Thr Gln Asn Val Asp Tyr Leu Asn
            580                 585                 590

Ser Tyr Tyr Tyr Leu Glu Ser Gln Lys Leu Ser Asp Asn Val Glu Asp
        595                 600                 605

Phe Thr Phe Thr Arg Ser Ile Glu Glu Ala Leu Asp Asn Ser Ala Lys
    610                 615                 620

Val Tyr Thr Tyr Phe Pro Thr Leu Ala Asn Lys Val Asn Ala Gly Val
625                 630                 635                 640

Gln Gly Gly Leu Phe Leu Met Trp Ala Asn Asp Val Val Glu Asp Phe
                645                 650                 655

Thr Thr Asn Ile Leu Arg Lys Asp Thr Leu Asp Lys Ile Ser Asp Val
            660                 665                 670

Ser Ala Ile Ile Pro Tyr Ile Gly Pro Ala Leu Asn Ile Ser Asn Ser
        675                 680                 685

Val Arg Arg Gly Asn Phe Thr Glu Ala Phe Ala Val Thr Gly Val Thr
    690                 695                 700

Ile Leu Leu Glu Ala Phe Pro Glu Phe Thr Ile Pro Ala Leu Gly Ala
705                 710                 715                 720

Phe Val Ile Tyr Ser Lys Val Gln Glu Arg Asn Glu Ile Ile Lys Thr
                725                 730                 735

Ile Asp Asn Cys Leu Glu Gln Arg Ile Lys Arg Trp Lys Asp Ser Tyr
            740                 745                 750

Glu Trp Met Met Gly Thr Trp Leu Ser Arg Ile Ile Thr Gln Phe Asn
        755                 760                 765

Asn Ile Ser Tyr Gln Met Tyr Asp Ser Leu Asn Tyr Gln Ala Gly Ala
    770                 775                 780

Ile Lys Ala Lys Ile Asp Leu Glu Tyr Lys Lys Tyr Ser Gly Ser Asp
785                 790                 795                 800
```

```
Lys Glu Asn Ile Lys Ser Gln Val Glu Asn Leu Lys Asn Ser Leu Asp
                805                 810                 815
Val Lys Ile Ser Glu Ala Met Asn Asn Ile Asn Lys Phe Ile Arg Glu
            820                 825                 830
Cys Ser Val Thr Tyr Leu Phe Lys Asn Met Leu Pro Lys Val Ile Asp
        835                 840                 845
Glu Leu Asn Glu Phe Asp Arg Asn Thr Lys Ala Lys Leu Ile Asn Leu
    850                 855                 860
Ile Asp Ser His Asn Ile Ile Leu Val Gly Glu Val Asp Lys Leu Lys
865                 870                 875                 880
Ala Lys Val Asn Asn Ser Phe Gln Asn Thr Ile Pro Phe Asn Ile Phe
                885                 890                 895
Ser Tyr Thr Asn Asn Ser Leu Leu Lys Asp Ile Ile Asn Glu Tyr Phe
            900                 905                 910
Asn Leu Glu Ala Leu Ala Ser Gly His His His His His His Lys Leu
        915                 920                 925

<210> SEQ ID NO 28
<211> LENGTH: 213
<212> TYPE: DNA
<213> ORGANISM: artificial sequence
<220> FEATURE:
<223> OTHER INFORMATION: DNA sequence of the CP VIP-C linker

<400> SEQUENCE: 28
ggatccacgc acgtcgacgc gattgatggt cgtcactctg acgctgtttt caccgacaac      60
tacacccgtc tgcgtaaaca gatggctgtt aaaaaatacc tgaactctat cctgaacgcg     120
ctagcgggcg gtggcggtag cggcggtggc ggtagcggcg gtggcggtag cgcactagtg     180
ctgcagacgc acggtctaga atgataaaag ctt                                  213

<210> SEQ ID NO 29
<211> LENGTH: 2730
<212> TYPE: DNA
<213> ORGANISM: artificial sequence
<220> FEATURE:
<223> OTHER INFORMATION: DNA sequence of the CP VIP-C fusion

<400> SEQUENCE: 29
aaaaacatcc tgtacctgga tacccatctg aatccctggc gaacgaaacc ggaaaaagcg      60
tttcgtatca ccggcaacat ttgggttatt ccggatcgtt ttagccgtaa cagcaacccg     120
aatctgaata aaccgccgcg tgttaccagc ccgaaaagcg gttattacga tccgaactat     180
ctgagcaccg atagcgataa agatacccttc ctgaaagaaa tcatcaaact gttcaaacgc     240
atcaacagcc gtgaaattgg cgaagaactg atctatcgcc tgagcaccga tattccgttt     300
ccgggcaaca acaacacccc gatcaacacc tttgatttcg atgtggattt caacagcgtt     360
gatgttaaaa cccgccaggg taacaattgg gtgaaaaccg gcagcattaa cccgagcgtg     420
attattaccg gtccgcgcga aaacattatt gatccggaaa ccagcacctt taaactgacc     480
aacaacacct tgcggcgcag gaaggtttt ggcgcgctga gcattattag cattagcccg     540
cgctttatgc tgacctatag caacgcgacc aacgatgttg tgaaggccg tttcagcaaa     600 agcgaatttt gcatggaccc gatcctgatc ctgatgcatg aactgaacca tgcgatgcat     660
aacctgtatg gcatcgcgat tccgaacgat cagaccatta gcagcgtgac cagcaacatc     720
ttttacagcc agtacaacgt gaaactggaa tatgcggaaa tctatgcgtt tggcggtccg     780
```

| | | |
|---|---|---|
| accattgatc tgattccgaa aagcgcgcgc aaatacttcg aagaaaaagc gctggattac | 840 | |
| tatcgcagca ttgcgaaacg tctgaacagc attaccaccg cgaatccgag cagcttcaac | 900 | |
| aaatatatcg gcgaatataa acagaaactg atccgcaaat atcgctttgt ggtggaaagc | 960 | |
| agcggcgaag ttaccgttaa ccgcaataaa ttcgtggaac tgtacaacga actgacccag | 1020 | |
| atcttcaccg aatttaacta tgcgaaaatc tataacgtgc agaaccgtaa atctacctg | 1080 | |
| agcaacgtgt ataccccggt gaccgcgaat attctggatg ataacgtgta cgatatccag | 1140 | |
| aacggcttta acatcccgaa aagcaacctg aacgttctgt ttatgggcca gaacctgagc | 1200 | |
| cgtaatccgg cgctgcgtaa agtgaacccg gaaaacatgc tgtacctgtt caccaaattt | 1260 | |
| tgcgtcgacg cgattgatgg tcgtggtggt cgtggtgaca tgttcggtgc tgcgctagcg | 1320 | |
| ggcgtcgacg cgattgatgg tcgtcactct gacgctgttt tcaccgacaa ctacacccgt | 1380 | |
| ctgcgtaaac agatggctgt taaaaaatac ctgaactcta tcctgaacgc gctagcgggc | 1440 | |
| ggtggcggta gcggcggtgg cggtagcggc ggtggcggta gcgcactagt gctgcagaaa | 1500 | |
| accgatatct tcctgcgcaa agatatcaac gaagaaaccg aagtgatcta ctacccggat | 1560 | |
| aacgtgagcg ttgatcaggt gatcctgagc aaaaacacca gcgaacatgg tcagctggat | 1620 | |
| ctgctgtatc cgagcattga tagcgaaagc gaaattctgc cgggcgaaaa ccaggtgttt | 1680 | |
| tacgataacc gtacccagaa cgtggattac ctgaacagct attactacct ggaaagccag | 1740 | |
| aaactgagcg ataacgtgga agattttacc tttacccgca gcattgaaga agcgctggat | 1800 | |
| aacagcgcga agtttacac ctatttttccg accctggcga acaaagttaa tgcgggtgtt | 1860 | |
| cagggcggtc tgtttctgat gtgggcgaac gatgtggtgg aagatttcac caccaacatc | 1920 | |
| ctgcgtaaag ataccctgga taaaatcagc gatgttagcg cgattattcc gtatattggt | 1980 | |
| ccggcgctga acattagcaa tagcgtgcgt cgtggcaatt ttaccgaagc gtttgcggtt | 2040 | |
| accggtgtga ccattctgct ggaagcgttt ccggaattta ccattccggc gctgggtgcg | 2100 | |
| tttgtgatct atagcaaagt gcaggaacgc aacgaaatca tcaaaaccat cgataactgc | 2160 | |
| ctggaacagc gtattaaacg ctggaaagat agctatgaat ggatgatggg cacctggctg | 2220 | |
| agccgtatta tcacccagtt caacaacatc agctaccaga tgtacgatag cctgaactat | 2280 | |
| caggcgggtg cgattaaagc gaaaatcgat ctggaataca aaaaatacag cggcagcgat | 2340 | |
| aaagaaaaca tcaaaagcca ggttgaaaac ctgaaaaaca gcctggatgt gaaaattagc | 2400 | |
| gaagcgatga ataacatcaa caaattcatc cgcgaatgca gcgtgaccta cctgttcaaa | 2460 | |
| aacatgctgc cgaaagtgat cgatgaactg aacgaatttg atcgcaacac caaagcgaaa | 2520 | |
| ctgatcaacc tgatcgatag ccacaacatt attctggtgg cgaagtggga taaactgaaa | 2580 | |
| gcgaaagtta acaacagctt ccagaacacc atcccgttta acatcttcag ctataccaac | 2640 | |
| aacagcctgc tgaaagatat catcaacgaa tacttcaatc tagaagcact agcgagtggg | 2700 | |
| caccatcacc atcaccatta atgaaagctt | 2730 | |

<210> SEQ ID NO 30
<211> LENGTH: 908
<212> TYPE: PRT
<213> ORGANISM: artificial sequence
<220> FEATURE:
<223> OTHER INFORMATION: Protein sequence of the CP VIP-C fusion

<400> SEQUENCE: 30

Lys Asn Ile Leu Tyr Leu Asp Thr His Leu Asn Thr Leu Ala Asn Glu
1               5                   10                  15

Pro Glu Lys Ala Phe Arg Ile Thr Gly Asn Ile Trp Val Ile Pro Asp
            20                  25                  30

Arg Phe Ser Arg Asn Ser Asn Pro Asn Leu Asn Lys Pro Pro Arg Val
            35                  40                  45

Thr Ser Pro Lys Ser Gly Tyr Tyr Asp Pro Asn Tyr Leu Ser Thr Asp
            50                  55                  60

Ser Asp Lys Asp Thr Phe Leu Lys Glu Ile Ile Lys Leu Phe Lys Arg
 65                  70                  75                  80

Ile Asn Ser Arg Glu Ile Gly Glu Glu Leu Ile Tyr Arg Leu Ser Thr
                85                  90                  95

Asp Ile Pro Phe Pro Gly Asn Asn Thr Pro Ile Asn Thr Phe Asp
            100                 105                 110

Phe Asp Val Asp Phe Asn Ser Val Asp Val Lys Thr Arg Gln Gly Asn
            115                 120                 125

Asn Trp Val Lys Thr Gly Ser Ile Asn Pro Ser Val Ile Ile Thr Gly
            130                 135                 140

Pro Arg Glu Asn Ile Ile Asp Pro Glu Thr Ser Thr Phe Lys Leu Thr
145                 150                 155                 160

Asn Asn Thr Phe Ala Ala Gln Glu Gly Phe Gly Ala Leu Ser Ile Ile
            165                 170                 175

Ser Ile Ser Pro Arg Phe Met Leu Thr Tyr Ser Asn Ala Thr Asn Asp
            180                 185                 190

Val Gly Glu Gly Arg Phe Ser Lys Ser Glu Phe Cys Met Asp Pro Ile
            195                 200                 205

Leu Ile Leu Met His Glu Leu Asn His Ala Met His Asn Leu Tyr Gly
210                 215                 220

Ile Ala Ile Pro Asn Asp Gln Thr Ile Ser Ser Val Thr Ser Asn Ile
225                 230                 235                 240

Phe Tyr Ser Gln Tyr Asn Val Lys Leu Glu Tyr Ala Glu Ile Tyr Ala
            245                 250                 255

Phe Gly Gly Pro Thr Ile Asp Leu Ile Pro Lys Ser Ala Arg Lys Tyr
            260                 265                 270

Phe Glu Glu Lys Ala Leu Asp Tyr Tyr Arg Ser Ile Ala Lys Arg Leu
            275                 280                 285

Asn Ser Ile Thr Thr Ala Asn Pro Ser Ser Phe Asn Lys Tyr Ile Gly
290                 295                 300

Glu Tyr Lys Gln Lys Leu Ile Arg Lys Tyr Arg Phe Val Val Glu Ser
305                 310                 315                 320

Ser Gly Glu Val Thr Val Asn Arg Asn Lys Phe Val Glu Leu Tyr Asn
            325                 330                 335

Glu Leu Thr Gln Ile Phe Thr Glu Phe Asn Tyr Ala Lys Ile Tyr Asn
            340                 345                 350

Val Gln Asn Arg Lys Ile Tyr Leu Ser Asn Val Tyr Thr Pro Val Thr
            355                 360                 365

Ala Asn Ile Leu Asp Asp Asn Val Tyr Asp Ile Gln Asn Gly Phe Asn
            370                 375                 380

Ile Pro Lys Ser Asn Leu Asn Val Leu Phe Met Gly Gln Asn Leu Ser
385                 390                 395                 400

Arg Asn Pro Ala Leu Arg Lys Val Asn Pro Glu Asn Met Leu Tyr Leu
            405                 410                 415

Phe Thr Lys Phe Cys Val Asp Ala Ile Asp Gly Arg Gly Arg Gly
            420                 425                 430

Asp Met Phe Gly Ala Ala Leu Ala Gly Val Asp Ala Ile Asp Gly Arg

```
            435                 440                 445
His Ser Asp Ala Val Phe Thr Asp Asn Tyr Thr Arg Leu Arg Lys Gln
450                 455                 460

Met Ala Val Lys Lys Tyr Leu Asn Ser Ile Leu Asn Ala Leu Ala Gly
465                 470                 475                 480

Gly Gly Gly Ser Gly Gly Gly Ser Gly Gly Gly Ser Ala Leu
                485                 490                 495

Val Leu Gln Lys Thr Asp Ile Phe Leu Arg Lys Asp Ile Asn Glu Glu
                500                 505                 510

Thr Glu Val Ile Tyr Tyr Pro Asp Asn Val Ser Val Asp Gln Val Ile
            515                 520                 525

Leu Ser Lys Asn Thr Ser Glu His Gly Gln Leu Asp Leu Leu Tyr Pro
            530                 535                 540

Ser Ile Asp Ser Glu Ser Glu Ile Leu Pro Gly Glu Asn Gln Val Phe
545                 550                 555                 560

Tyr Asp Asn Arg Thr Gln Asn Val Asp Tyr Leu Asn Ser Tyr Tyr Tyr
                565                 570                 575

Leu Glu Ser Gln Lys Leu Ser Asp Asn Val Glu Asp Phe Thr Phe Thr
                580                 585                 590

Arg Ser Ile Glu Glu Ala Leu Asp Asn Ser Ala Lys Val Tyr Thr Tyr
                595                 600                 605

Phe Pro Thr Leu Ala Asn Lys Val Asn Ala Gly Val Gln Gly Gly Leu
610                 615                 620

Phe Leu Met Trp Ala Asn Asp Val Val Glu Asp Phe Thr Thr Asn Ile
625                 630                 635                 640

Leu Arg Lys Asp Thr Leu Asp Lys Ile Ser Asp Val Ser Ala Ile Ile
                645                 650                 655

Pro Tyr Ile Gly Pro Ala Leu Asn Ile Ser Asn Ser Val Arg Arg Gly
                660                 665                 670

Asn Phe Thr Glu Ala Phe Ala Val Thr Gly Val Thr Ile Leu Leu Glu
                675                 680                 685

Ala Phe Pro Glu Phe Thr Ile Pro Ala Leu Gly Ala Phe Val Ile Tyr
                690                 695                 700

Ser Lys Val Gln Glu Arg Asn Glu Ile Ile Lys Thr Ile Asp Asn Cys
705                 710                 715                 720

Leu Glu Gln Arg Ile Lys Arg Trp Lys Asp Ser Tyr Glu Trp Met Met
                725                 730                 735

Gly Thr Trp Leu Ser Arg Ile Ile Thr Gln Phe Asn Asn Ile Ser Tyr
                740                 745                 750

Gln Met Tyr Asp Ser Leu Asn Tyr Gln Ala Gly Ala Ile Lys Ala Lys
                755                 760                 765

Ile Asp Leu Glu Tyr Lys Lys Tyr Ser Gly Ser Asp Lys Glu Asn Ile
                770                 775                 780

Lys Ser Gln Val Glu Asn Leu Lys Asn Ser Leu Asp Val Lys Ile Ser
785                 790                 795                 800

Glu Ala Met Asn Asn Ile Asn Lys Phe Ile Arg Glu Cys Ser Val Thr
                805                 810                 815

Tyr Leu Phe Lys Asn Met Leu Pro Lys Val Ile Asp Glu Leu Asn Glu
                820                 825                 830

Phe Asp Arg Asn Thr Lys Ala Lys Leu Ile Asn Leu Ile Asp Ser His
                835                 840                 845

Asn Ile Ile Leu Val Gly Glu Val Asp Lys Leu Lys Ala Lys Val Asn
850                 855                 860
```

```
Asn Ser Phe Gln Asn Thr Ile Pro Phe Asn Ile Phe Ser Tyr Thr Asn
865                 870                 875                 880

Asn Ser Leu Leu Lys Asp Ile Ile Asn Glu Tyr Phe Asn Leu Glu Ala
            885                 890                 895

Leu Ala Ser Gly His His His His His Lys Leu
            900                 905
```

<210> SEQ ID NO 31
<211> LENGTH: 210
<212> TYPE: DNA
<213> ORGANISM: artificial sequence
<220> FEATURE:
<223> OTHER INFORMATION: DNA sequecne of the CP Gastrin releasing peptide -C linker

<400> SEQUENCE: 31

```
ggatccacgc acgtcgacgc gattgatggt cgtgttccgc tgccggctgg tggtggtacc      60
gttctgacca aaatgtaccc gcgtggtaac cactgggctg ttggtcacct gatggcgcta     120
gcgggcggtg gcggtagcgg cggtggcggt agcggcggtg gcggtagcgc actagtgctg     180
cagacgcacg gtctagaatg ataaaagctt                                       210
```

<210> SEQ ID NO 32
<211> LENGTH: 2787
<212> TYPE: DNA
<213> ORGANISM: artificial sequence
<220> FEATURE:
<223> OTHER INFORMATION: DNA sequence of the CP Gastrin releasing peptide -C fusion

<400> SEQUENCE: 32

```
ggatccgaat tcatgccgat caccatcaac aacttcaact acagcgatcc ggtggataac      60
aaaaacatcc tgtacctgga tacccatctg aatacccctgg cgaacgaacc ggaaaaagcg    120
tttcgtatca ccggcaacat tgggttatt ccggatcgtt ttagccgtaa cagcaacccg      180
aatctgaata accgccgcg tgttaccagc ccgaaaagcg gttattacga tccgaactat      240
ctgagcaccg atagcgataa agataccttc ctgaaagaaa tcatcaaact gttcaaacgc    300
atcaacagcc gtgaaattgg cgaagaactg atctatcgcc tgagcaccga tattccgttt    360
ccgggcaaca caacaccccc gatcaacacc tttgatttcg atgtggattt caacagcgtt    420
gatgttaaaa cccgccaggg taacaattgg gtgaaaaccg gcagcattaa cccgagcgtg    480
attattaccg gtccgcgcga aaacattatt gatccggaaa ccagcacctt taaactgacc    540
aacaacacct tgcggcgca ggaaggttttt ggcgcgctga gcattattag cattagcccg    600
cgctttatgc tgacctatag caacgcgacc aacgatgttg gtgaaggccg tttcagcaaa    660
agcgaatttt gcatggaccc gatcctgatc ctgatgcatg aactgaacca tgcgatgcat    720
aacctgtatg gcatcgcgat tccgaacgat cagaccatta gcagcgtgac cagcaacatc    780 tttttacagcc agtacaacgt gaaactggaa tatgcggaaa tctatgcgtt tggcggtccg    840
accattgatc tgattccgaa aagcgcgcgc aaatacttcg aagaaaaagc gctggattac    900
tatcgcagca ttgcgaaacg tctgaacagc attaccaccg cgaatccgag cagcttcaac    960
aaatatatcg gcgaatataa acagaaactg atccgcaaat atcgctttgt ggtggaaagc   1020
agcggcgaag ttaccgttaa ccgcaataaa ttcgtggaac tgtacaacga actgacccag   1080
atcttcaccg aatttaacta tgcgaaaatc tataacgtgc agaaccgtaa aatctacctg   1140
agcaacgtgt ataccccggt gaccgcgaat attctggatg ataacgtgta cgatatccag   1200
```

```
aacggcttta acatcccgaa aagcaacctg aacgttctgt ttatgggcca gaacctgagc    1260
cgtaatccgg cgctgcgtaa agtgaacccg gaaaacatgc tgtacctgtt caccaaattt    1320
tgcgtcgacg cgattgatgg tcgtgttccg ctgccggctg gtggtggtac cgttctgacc    1380
aaaatgtacc cgcgtggtaa ccactgggct gttggtcacc tgatggcgct agcgggcggt    1440
ggcggtagcg gcggtggcgg tagcggcggt ggcggtagcg cactagtgct gcagtgtcgt    1500
gaactgctgg tgaaaaacac cgatctgccg tttattggcg atatcagcga tgtgaaaacc    1560
gatatcttcc tgcgcaaaga tatcaacgaa gaaaccgaag tgatctacta cccggataac    1620
gtgagcgttg atcaggtgat cctgagcaaa acaccagcg aacatggtca gctggatctg    1680
ctgtatccga gcattgatag cgaaagcgaa attctgccgg gcgaaaacca ggtgttttac    1740
gataaccgta cccagaacgt ggattacctg aacagctatt actacctgga aagccagaaa    1800
ctgagcgata acgtggaaga tttaccttt acccgcagca ttgaagaagc gctggataac    1860
agcgcgaaag tttacaccta ttttccgacc ctggcgaaca agttaatgc gggtgttcag    1920 ggcggtctgt ttctgatgtg ggcgaacgat gtggtggaag atttcaccac caacatcctg    1980
cgtaaagata ccctggataa aatcagcgat gttagcgcga ttattccgta tattggtccg    2040
gcgctgaaca ttagcaatag cgtgcgtcgt ggcaattta ccgaagcgtt tgcggttacc    2100
ggtgtgacca ttctgctgga agcgtttccg gaatttacca ttccggcgct gggtgcgttt    2160
gtgatctata gcaaagtgca ggaacgcaac gaaatcatca aaccatcga taactgcctg    2220 gaacagcgta ttaaacgctg gaagatagc tatgaatgga tgatgggcac ctggctgagc    2280
cgtattatca cccagttcaa caacatcagc taccagatgt acgatagcct gaactatcag    2340
gcgggtgcga ttaaagcgaa aatcgatctg gaatacaaaa aatacagcgg cagcgataaa    2400
gaaaacatca aagccaggt tgaaacctg aaaaacagcc tggatgtgaa aattagcgaa    2460
gcgatgaata acatcaacaa attcatccgc gaatgcagcg tgacctacct gttcaaaaac    2520
atgctgccga aagtgatcga tgaactgaac gaatttgatc gcaacaccaa agcgaaactg    2580
atcaacctga tcgatagcca caacattatt ctggtgggcg aagtggataa actgaaagcg    2640
aaagttaaca acagcttcca gaacaccatc ccgtttaaca tcttcagcta taccaacaac    2700
agcctgctga agatatcat caacgaatac ttcaatctag aagcactagc gagtgggcac    2760
catcaccatc accattaatg aaagctt                                         2787
```

<210> SEQ ID NO 33
<211> LENGTH: 927
<212> TYPE: PRT
<213> ORGANISM: artificial sequence
<220> FEATURE:
<223> OTHER INFORMATION: Protein sequence of the CP Gastrin releasing
      peptide -C fusion

<400> SEQUENCE: 33

Gly Ser Glu Phe Met Pro Ile Thr Ile Asn Asn Phe Asn Tyr Ser Asp
1               5                   10                  15

Pro Val Asp Asn Lys Asn Ile Leu Tyr Leu Asp Thr His Leu Asn Thr
            20                  25                  30

Leu Ala Asn Glu Pro Glu Lys Ala Phe Arg Ile Thr Gly Asn Ile Trp
        35                  40                  45

Val Ile Pro Asp Arg Phe Ser Arg Asn Ser Asn Pro Asn Leu Asn Lys
    50                  55                  60

Pro Pro Arg Val Thr Ser Pro Lys Ser Gly Tyr Tyr Asp Pro Asn Tyr

```
            65                   70                  75                  80
Leu Ser Thr Asp Ser Asp Lys Asp Thr Phe Leu Lys Glu Ile Ile Lys
                         85                  90                  95
Leu Phe Lys Arg Ile Asn Ser Arg Glu Ile Gly Glu Glu Leu Ile Tyr
                100                 105                 110
Arg Leu Ser Thr Asp Ile Pro Phe Pro Gly Asn Asn Thr Pro Ile
            115                 120                 125
Asn Thr Phe Asp Phe Asp Val Asp Phe Asn Ser Val Asp Val Lys Thr
    130                 135                 140
Arg Gln Gly Asn Asn Trp Val Lys Thr Gly Ser Ile Asn Pro Ser Val
145                 150                 155                 160
Ile Ile Thr Gly Pro Arg Glu Asn Ile Ile Asp Pro Glu Thr Ser Thr
                        165                 170                 175
Phe Lys Leu Thr Asn Asn Thr Phe Ala Ala Gln Glu Gly Phe Gly Ala
                180                 185                 190
Leu Ser Ile Ile Ser Ile Ser Pro Arg Phe Met Leu Thr Tyr Ser Asn
            195                 200                 205
Ala Thr Asn Asp Val Gly Glu Gly Arg Phe Ser Lys Ser Glu Phe Cys
    210                 215                 220
Met Asp Pro Ile Leu Ile Leu Met His Glu Leu Asn His Ala Met His
225                 230                 235                 240
Asn Leu Tyr Gly Ile Ala Ile Pro Asn Asp Gln Thr Ile Ser Ser Val
                        245                 250                 255
Thr Ser Asn Ile Phe Tyr Ser Gln Tyr Asn Val Lys Leu Glu Tyr Ala
                260                 265                 270
Glu Ile Tyr Ala Phe Gly Gly Pro Thr Ile Asp Leu Ile Pro Lys Ser
            275                 280                 285
Ala Arg Lys Tyr Phe Glu Glu Lys Ala Leu Asp Tyr Tyr Arg Ser Ile
    290                 295                 300
Ala Lys Arg Leu Asn Ser Ile Thr Thr Ala Asn Pro Ser Ser Phe Asn
305                 310                 315                 320
Lys Tyr Ile Gly Glu Tyr Lys Gln Lys Leu Ile Arg Lys Tyr Arg Phe
                        325                 330                 335
Val Val Glu Ser Ser Gly Glu Val Thr Val Asn Arg Asn Lys Phe Val
                340                 345                 350
Glu Leu Tyr Asn Glu Leu Thr Gln Ile Phe Thr Glu Phe Asn Tyr Ala
            355                 360                 365
Lys Ile Tyr Asn Val Gln Asn Arg Lys Ile Tyr Leu Ser Asn Val Tyr
    370                 375                 380
Thr Pro Val Thr Ala Asn Ile Leu Asp Asp Asn Val Tyr Asp Ile Gln
385                 390                 395                 400
Asn Gly Phe Asn Ile Pro Lys Ser Asn Leu Asn Val Leu Phe Met Gly
                        405                 410                 415
Gln Asn Leu Ser Arg Asn Pro Ala Leu Arg Lys Val Asn Pro Glu Asn
                420                 425                 430
Met Leu Tyr Leu Phe Thr Lys Phe Cys Val Asp Ala Ile Asp Gly Arg
            435                 440                 445
Val Pro Leu Pro Ala Gly Gly Thr Val Leu Thr Lys Met Tyr Pro
    450                 455                 460
Arg Gly Asn His Trp Ala Val Gly His Leu Met Ala Leu Ala Gly Gly
465                 470                 475                 480
Gly Gly Ser Gly Gly Gly Ser Gly Gly Gly Ser Ala Leu Val
                        485                 490                 495
```

```
Leu Gln Cys Arg Glu Leu Leu Val Lys Asn Thr Asp Leu Pro Phe Ile
            500                 505                 510
Gly Asp Ile Ser Asp Val Lys Thr Asp Ile Phe Leu Arg Lys Asp Ile
        515                 520                 525
Asn Glu Glu Thr Glu Val Ile Tyr Tyr Pro Asn Val Ser Val Asp
    530                 535                 540
Gln Val Ile Leu Ser Lys Asn Thr Ser Glu His Gly Gln Leu Asp Leu
545                 550                 555                 560
Leu Tyr Pro Ser Ile Asp Ser Glu Ser Glu Ile Leu Pro Gly Glu Asn
                565                 570                 575
Gln Val Phe Tyr Asp Asn Arg Thr Gln Asn Val Asp Tyr Leu Asn Ser
            580                 585                 590
Tyr Tyr Tyr Leu Glu Ser Gln Lys Leu Ser Asp Asn Val Glu Asp Phe
        595                 600                 605
Thr Phe Thr Arg Ser Ile Glu Glu Ala Leu Asp Asn Ser Ala Lys Val
    610                 615                 620
Tyr Thr Tyr Phe Pro Thr Leu Ala Asn Lys Val Asn Ala Gly Val Gln
625                 630                 635                 640
Gly Gly Leu Phe Leu Met Trp Ala Asn Asp Val Val Glu Asp Phe Thr
                645                 650                 655
Thr Asn Ile Leu Arg Lys Asp Thr Leu Asp Lys Ile Ser Asp Val Ser
            660                 665                 670
Ala Ile Ile Pro Tyr Ile Gly Pro Ala Leu Asn Ile Ser Asn Ser Val
        675                 680                 685
Arg Arg Gly Asn Phe Thr Glu Ala Phe Ala Val Thr Gly Val Thr Ile
    690                 695                 700
Leu Leu Glu Ala Phe Pro Glu Phe Thr Ile Pro Ala Leu Gly Ala Phe
705                 710                 715                 720
Val Ile Tyr Ser Lys Val Gln Glu Arg Asn Glu Ile Ile Lys Thr Ile
                725                 730                 735
Asp Asn Cys Leu Glu Gln Arg Ile Lys Arg Trp Lys Asp Ser Tyr Glu
            740                 745                 750
Trp Met Met Gly Thr Trp Leu Ser Arg Ile Ile Thr Gln Phe Asn Asn
        755                 760                 765
Ile Ser Tyr Gln Met Tyr Asp Ser Leu Asn Tyr Gln Ala Gly Ala Ile
    770                 775                 780
Lys Ala Lys Ile Asp Leu Glu Tyr Lys Tyr Ser Gly Ser Asp Lys
785                 790                 795                 800
Glu Asn Ile Lys Ser Gln Val Glu Asn Leu Lys Asn Ser Leu Asp Val
                805                 810                 815
Lys Ile Ser Glu Ala Met Asn Asn Ile Asn Lys Phe Ile Arg Glu Cys
            820                 825                 830
Ser Val Thr Tyr Leu Phe Lys Asn Met Leu Pro Lys Val Ile Asp Glu
        835                 840                 845
Leu Asn Glu Phe Asp Arg Asn Thr Lys Ala Lys Leu Ile Asn Leu Ile
    850                 855                 860
Asp Ser His Asn Ile Ile Leu Val Gly Glu Val Asp Lys Leu Lys Ala
865                 870                 875                 880
Lys Val Asn Asn Ser Phe Gln Asn Thr Ile Pro Phe Asn Ile Phe Ser
                885                 890                 895
Tyr Thr Asn Asn Ser Leu Leu Lys Asp Ile Ile Asn Glu Tyr Phe Asn
            900                 905                 910
```

```
Leu Glu Ala Leu Ala Ser Gly His His His His His Lys Leu
        915                 920                 925
```

<210> SEQ ID NO 34
<211> LENGTH: 10
<212> TYPE: PRT
<213> ORGANISM: artificial sequence
<220> FEATURE:
<223> OTHER INFORMATION: synthetic peptide

<400> SEQUENCE: 34

```
Pro Leu Ala Glu Ile Asp Gly Ile Glu Leu
1               5                   10
```

<210> SEQ ID NO 35
<211> LENGTH: 12
<212> TYPE: PRT
<213> ORGANISM: artificial sequence
<220> FEATURE:
<223> OTHER INFORMATION: synthetic peptide

<400> SEQUENCE: 35

```
Cys Pro Leu Ala Glu Ile Asp Gly Ile Glu Leu Cys
1               5                   10
```

<210> SEQ ID NO 36
<211> LENGTH: 7
<212> TYPE: PRT
<213> ORGANISM: artificial sequence
<220> FEATURE:
<223> OTHER INFORMATION: synthetic peptide

<400> SEQUENCE: 36

```
Thr His Ala Leu Trp His Thr
1               5
```

<210> SEQ ID NO 37
<211> LENGTH: 15
<212> TYPE: PRT
<213> ORGANISM: artificial sequence
<220> FEATURE:
<223> OTHER INFORMATION: LEBP-1 peptide

<400> SEQUENCE: 37

```
Gln Pro Phe Met Gln Cys Leu Cys Leu Ile Tyr Asp Ala Ser Cys
1               5                   10                  15
```

<210> SEQ ID NO 38
<211> LENGTH: 15
<212> TYPE: PRT
<213> ORGANISM: artificial sequence
<220> FEATURE:
<223> OTHER INFORMATION: LEBP-2 peptide

<400> SEQUENCE: 38

```
Arg Asn Val Pro Pro Ile Phe Asn Asp Val Tyr Trp Ile Ala Phe
1               5                   10                  15
```

<210> SEQ ID NO 39
<211> LENGTH: 14
<212> TYPE: PRT
<213> ORGANISM: artificial sequence
<220> FEATURE:
<223> OTHER INFORMATION: LEBP-3 peptide

<400> SEQUENCE: 39

```
Val Phe Arg Val Arg Pro Trp Tyr Gln Ser Thr Ser Gln Ser
```

```
                1               5                    10
```

<210> SEQ ID NO 40
<211> LENGTH: 7
<212> TYPE: PRT
<213> ORGANISM: artificial sequence
<220> FEATURE:
<223> OTHER INFORMATION: sythetic peptide

<400> SEQUENCE: 40

Ser Glu Arg Ser Met Asn Phe
1               5

<210> SEQ ID NO 41
<211> LENGTH: 7
<212> TYPE: PRT
<213> ORGANISM: artificial sequence
<220> FEATURE:
<223> OTHER INFORMATION: synthetic peptide

<400> SEQUENCE: 41

Tyr Gly Leu Pro His Lys Phe
1               5

<210> SEQ ID NO 42
<211> LENGTH: 7
<212> TYPE: PRT
<213> ORGANISM: artificial sequence
<220> FEATURE:
<223> OTHER INFORMATION: synthetic peptide

<400> SEQUENCE: 42

Pro Ser Gly Ala Ala Arg Ala
1               5

<210> SEQ ID NO 43
<211> LENGTH: 7
<212> TYPE: PRT
<213> ORGANISM: artificial sequence
<220> FEATURE:
<223> OTHER INFORMATION: synthetic peptide

<400> SEQUENCE: 43

Leu Pro His Lys Ser Met Pro
1               5

<210> SEQ ID NO 44
<211> LENGTH: 7
<212> TYPE: PRT
<213> ORGANISM: artificial sequence
<220> FEATURE:
<223> OTHER INFORMATION: synthetic peptide

<400> SEQUENCE: 44

Leu Gln His Lys Ser Met Pro
1               5

<210> SEQ ID NO 45
<211> LENGTH: 7
<212> TYPE: PRT
<213> ORGANISM: artificial sequence
<220> FEATURE:
<223> OTHER INFORMATION: synthetic peptide

<400> SEQUENCE: 45

Phe Ser Leu Ser Lys Pro Pro
1               5

```
<210> SEQ ID NO 46
<211> LENGTH: 7
<212> TYPE: PRT
<213> ORGANISM: artificial sequence
<220> FEATURE:
<223> OTHER INFORMATION: synthetic peptide

<400> SEQUENCE: 46

His Ser Met Gln Leu Ser Thr
1               5

<210> SEQ ID NO 47
<211> LENGTH: 7
<212> TYPE: PRT
<213> ORGANISM: artificial sequence
<220> FEATURE:
<223> OTHER INFORMATION: synthetic peptide

<400> SEQUENCE: 47

Ser Thr Gln Ala Met Phe Gln
1               5

<210> SEQ ID NO 48
<211> LENGTH: 17
<212> TYPE: PRT
<213> ORGANISM: artificial sequence
<220> FEATURE:
<223> OTHER INFORMATION: synthetic peptide

<400> SEQUENCE: 48

Cys Asp Ser Ala Phe Val Thr Val Asp Trp Gly Arg Ser Met Ser Leu
1               5                   10                  15

Cys

<210> SEQ ID NO 49
<211> LENGTH: 5
<212> TYPE: PRT
<213> ORGANISM: artificial sequence
<220> FEATURE:
<223> OTHER INFORMATION: synthetic peptide

<400> SEQUENCE: 49

Asp Asp Asp Asp Lys
1               5

<210> SEQ ID NO 50
<211> LENGTH: 4
<212> TYPE: PRT
<213> ORGANISM: artificial sequence
<220> FEATURE:
<223> OTHER INFORMATION: synthetic peptide

<400> SEQUENCE: 50

Ile Glu Gly Arg
1

<210> SEQ ID NO 51
<211> LENGTH: 4
<212> TYPE: PRT
<213> ORGANISM: artificial sequence
<220> FEATURE:
<223> OTHER INFORMATION: synthetic peptide

<400> SEQUENCE: 51

Ile Asp Gly Arg
```

<210> SEQ ID NO 52
<211> LENGTH: 7
<212> TYPE: PRT
<213> ORGANISM: artificial sequence
<220> FEATURE:
<223> OTHER INFORMATION: synthetic peptide

<400> SEQUENCE: 52

Glu Asn Leu Tyr Phe Gln Gly
1               5

<210> SEQ ID NO 53
<211> LENGTH: 6
<212> TYPE: PRT
<213> ORGANISM: artificial sequence
<220> FEATURE:
<223> OTHER INFORMATION: synthetic peptide

<400> SEQUENCE: 53

Leu Val Pro Arg Gly Ser
1               5

<210> SEQ ID NO 54
<211> LENGTH: 8
<212> TYPE: PRT
<213> ORGANISM: artificial sequence
<220> FEATURE:
<223> OTHER INFORMATION: synthetic peptide

<400> SEQUENCE: 54

Leu Glu Val Leu Phe Gln Gly Pro
1               5

<210> SEQ ID NO 55
<211> LENGTH: 25
<212> TYPE: PRT
<213> ORGANISM: Clostridium Botulinum
<220> FEATURE:
<223> OTHER INFORMATION: Type A1

<400> SEQUENCE: 55

Cys Val Arg Gly Ile Ile Thr Ser Lys Thr Lys Ser Leu Asp Lys Gly
1               5                   10                  15

Tyr Asn Lys Ala Leu Asn Asp Leu Cys
            20                  25

<210> SEQ ID NO 56
<211> LENGTH: 25
<212> TYPE: PRT
<213> ORGANISM: Clostridium Botulinum
<220> FEATURE:
<223> OTHER INFORMATION: Type A2

<400> SEQUENCE: 56

Cys Val Arg Gly Ile Ile Pro Phe Lys Thr Lys Ser Leu Asp Glu Gly
1               5                   10                  15

Tyr Asn Lys Ala Leu Asn Asp Leu Cys
            20                  25

<210> SEQ ID NO 57
<211> LENGTH: 10
<212> TYPE: PRT
<213> ORGANISM: Clostridium Botulinum
<220> FEATURE:

```
<223> OTHER INFORMATION: Type B

<400> SEQUENCE: 57

Cys Lys Ser Val Lys Ala Pro Gly Ile Cys
1               5                   10

<210> SEQ ID NO 58
<211> LENGTH: 17
<212> TYPE: PRT
<213> ORGANISM: Clostridium Botulinum
<220> FEATURE:
<223> OTHER INFORMATION: Type C

<400> SEQUENCE: 58

Cys His Lys Ala Ile Asp Gly Arg Ser Leu Tyr Asn Lys Thr Leu Asp
1               5                   10                  15

Cys

<210> SEQ ID NO 59
<211> LENGTH: 14
<212> TYPE: PRT
<213> ORGANISM: Clostridium Botulinum
<220> FEATURE:
<223> OTHER INFORMATION: Type D

<400> SEQUENCE: 59

Cys Leu Arg Leu Thr Lys Asn Ser Arg Asp Asp Ser Thr Cys
1               5                   10

<210> SEQ ID NO 60
<211> LENGTH: 15
<212> TYPE: PRT
<213> ORGANISM: Clostridium Botulinum
<220> FEATURE:
<223> OTHER INFORMATION: Type E

<400> SEQUENCE: 60

Cys Lys Asn Ile Val Ser Val Lys Gly Ile Arg Lys Ser Ile Cys
1               5                   10                  15

<210> SEQ ID NO 61
<211> LENGTH: 17
<212> TYPE: PRT
<213> ORGANISM: Clostridium Botulinum
<220> FEATURE:
<223> OTHER INFORMATION: Type F

<400> SEQUENCE: 61

Cys Lys Ser Val Ile Pro Arg Lys Gly Thr Lys Ala Pro Pro Arg Leu
1               5                   10                  15

Cys

<210> SEQ ID NO 62
<211> LENGTH: 15
<212> TYPE: PRT
<213> ORGANISM: Clostridium Botulinum
<220> FEATURE:
<223> OTHER INFORMATION: Type G

<400> SEQUENCE: 62

Cys Lys Pro Val Met Tyr Lys Asn Thr Gly Lys Ser Glu Gln Cys
1               5                   10                  15

<210> SEQ ID NO 63
<211> LENGTH: 29
```

```
<212> TYPE: PRT
<213> ORGANISM: Clostridium Tetani
<220> FEATURE:

<400> SEQUENCE: 63

Cys Lys Lys Ile Ile Pro Pro Thr Asn Ile Arg Glu Asn Leu Tyr Asn
1               5                   10                  15

Arg Thr Ala Ser Leu Thr Asp Leu Gly Gly Glu Leu Cys
            20                  25

<210> SEQ ID NO 64
<211> LENGTH: 23
<212> TYPE: PRT
<213> ORGANISM: Influenza A Virus
<220> FEATURE:

<400> SEQUENCE: 64

Gly Leu Phe Gly Ala Ile Ala Gly Phe Ile Glu Asn Gly Trp Glu Gly
1               5                   10                  15

Met Ile Asp Gly Trp Tyr Gly
            20
```